United States Patent
van den Boom et al.

(10) Patent No.: US 7,820,378 B2
(45) Date of Patent: Oct. 26, 2010

(54) FRAGMENTATION-BASED METHODS AND SYSTEMS FOR SEQUENCE VARIATION DETECTION AND DISCOVERY

(75) Inventors: Dirk van den Boom, La Jolla, CA (US); Sebastian Boecker, Bielefeld (DE)

(73) Assignee: Sequenom, Inc., San Diego, CA (US)

( * ) Notice: Subject to any disclaimer, the term of this patent is extended or adjusted under 35 U.S.C. 154(b) by 0 days.

(21) Appl. No.: 10/723,365

(22) Filed: Nov. 26, 2003

(65) Prior Publication Data

US 2005/0112590 A1 May 26, 2005

Related U.S. Application Data

(60) Provisional application No. 60/429,895, filed on Nov. 27, 2002.

(51) Int. Cl.
*C12Q 1/68* (2006.01)
*C12P 19/34* (2006.01)
(52) U.S. Cl. .......................... 435/6; 435/91.2
(58) Field of Classification Search ............... None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,762,823 A | 8/1988 | Wantanabe et al. |
| 4,826,360 A | 5/1989 | Iwasawa et al. |
| 4,851,018 A | 7/1989 | Lazzari et al. |
| 5,003,059 A | 3/1991 | Brennan |
| 5,079,342 A | 1/1992 | Alizon et al. ............... 530/324 |
| 5,118,937 A | 6/1992 | Hillenkamp et al. ......... 250/282 |
| 5,173,418 A | 12/1992 | Molin et al. ............... 435/198 |
| 5,210,412 A | 5/1993 | Levis et al. |
| 5,252,478 A | 10/1993 | Margarit Y Ros et al. ... 435/222 |
| 5,264,563 A | 11/1993 | Huse |
| 5,387,518 A | 2/1995 | Sawayanagi et al. ........ 435/221 |
| 5,391,490 A | 2/1995 | Varshavsky et al. ......... 435/224 |
| 5,427,927 A | 6/1995 | Meyer et al. ............... 435/69.7 |
| 5,436,150 A | 7/1995 | Chandrasegaran |
| 5,440,119 A | 8/1995 | Labowsky |
| 5,453,247 A | 9/1995 | Beavis et al. |
| 5,453,613 A | 9/1995 | Gray et al. |
| 5,498,545 A | 3/1996 | Vestal |
| 5,503,980 A | 4/1996 | Cantor |
| 5,506,137 A | 4/1996 | Mathur |
| 5,536,649 A | 7/1996 | Fraiser et al. .............. 435/91.2 |
| 5,547,835 A | 8/1996 | Köster ........................... 435/6 |
| 5,578,443 A | 11/1996 | Santamaria et al. |
| 5,580,733 A | 12/1996 | Levis et al. |
| 5,604,098 A | 2/1997 | Mead et al. |
| 5,605,798 A | 2/1997 | Köster ........................... 435/6 |
| 5,622,824 A | 4/1997 | Köster ........................... 435/6 |
| 5,631,134 A | 5/1997 | Cantor et al. |
| 5,635,713 A | 6/1997 | Labowsky |
| 5,646,020 A | 7/1997 | Swiggen et al. .......... 435/91.31 |
| 5,686,656 A | 11/1997 | Amirav et al. |
| 5,691,141 A | 11/1997 | Köster ........................... 435/6 |
| 5,700,672 A | 12/1997 | Mathur et al. |
| 5,714,330 A | 2/1998 | Brenner et al. |
| 5,753,439 A | 5/1998 | Smith et al. |
| 5,777,324 A | 7/1998 | Hillenkamp |
| 5,786,146 A | 7/1998 | Herman et al. |
| 5,792,664 A | 8/1998 | Chait et al. |
| 5,795,714 A | 8/1998 | Cantor et al. |
| 5,807,522 A | 9/1998 | Brown et al. |
| 5,830,712 A | 11/1998 | Rampersad et al. |
| 5,837,832 A | 11/1998 | Chee et al. |
| 5,843,669 A | 12/1998 | Kaiser et al. ................... 435/6 |
| 5,849,542 A | 12/1998 | Reeve |
| 5,851,765 A | 12/1998 | Koster |
| 5,853,979 A | 12/1998 | Green et al. |
| 5,858,705 A | 1/1999 | Wei et al. |
| 5,861,242 A | 1/1999 | Chee et al. |
| 5,864,137 A | 1/1999 | Becker et al. |
| 5,869,240 A | 2/1999 | Patterson |
| 5,869,242 A | 2/1999 | Kamb ........................... 435/6 |
| 5,871,911 A | 2/1999 | Dahlberg et al. |
| 5,872,003 A | 2/1999 | Koster |
| 5,874,283 A | 2/1999 | Harrington et al. ........ 435/252.3 |
| 5,885,841 A | 3/1999 | Higgs, Jr. et al. |
| 5,888,795 A | 3/1999 | Hamilton ................... 435/200 |
| 5,900,481 A | 5/1999 | Lough et al. |
| 5,928,870 A | 7/1999 | Lapidus et al. |
| 5,928,906 A | 7/1999 | Koster et al. |
| 5,932,451 A | 8/1999 | Wang et al. |

(Continued)

FOREIGN PATENT DOCUMENTS

AU 758454 B2 3/2003

(Continued)

OTHER PUBLICATIONS

SpectroCHIP™ BioArray specification sheet, 1 page.*

(Continued)

*Primary Examiner*—Samuel Woolwine
(74) *Attorney, Agent, or Firm*—Grant Anderson, LLP

(57) ABSTRACT

Fragmentation-based methods and systems, particularly mass spectrometric methods and systems, for the analysis of sequence variations are provided.

62 Claims, 4 Drawing Sheets

U.S. PATENT DOCUMENTS

| | | | |
|---|---|---|---|
| 5,948,902 A | 9/1999 | Honkanen et al. | |
| 5,952,176 A | 9/1999 | McCarthy et al. | 435/6 |
| 5,965,363 A | 10/1999 | Monforte et al. | |
| 5,975,492 A | 11/1999 | Brenes | |
| 5,976,806 A | 11/1999 | Mahejan et al. | |
| 6,017,704 A | 1/2000 | Herman et al. | |
| 6,022,688 A | 2/2000 | Jurinke et al. | |
| 6,024,925 A | 2/2000 | Little et al. | 422/100 |
| 6,043,031 A | 3/2000 | Köster et al. | 435/6 |
| 6,051,378 A | 4/2000 | Monforte et al. | |
| 6,054,276 A | 4/2000 | Macavicz | |
| 6,059,724 A | 5/2000 | Campell et al. | |
| 6,074,823 A | 6/2000 | Koster et al. | |
| 6,090,549 A | 7/2000 | Mirzabekov et al. | |
| 6,090,558 A | 7/2000 | Butler et al. | |
| 6,090,606 A | 7/2000 | Kaiser et al. | 435/199 |
| 6,099,553 A | 8/2000 | Hart et al. | 606/232 |
| 6,104,028 A | 8/2000 | Hunter et al. | |
| 6,107,039 A | 8/2000 | Hanna | |
| 6,110,426 A | 8/2000 | Shalon et al. | |
| 6,111,251 A | 8/2000 | Hillenkamp | |
| 6,112,161 A | 8/2000 | Dryden et al. | |
| 6,113,436 A | 9/2000 | Kuwahara et al. | |
| 6,133,436 A | 10/2000 | Koster et al. | |
| 6,140,053 A | 10/2000 | Koster et al. | |
| 6,146,854 A | 11/2000 | Koster et al. | |
| 6,188,064 B1 | 2/2001 | Koster | |
| 6,190,865 B1 | 2/2001 | Jendrisak et al. | 435/6 |
| 6,194,144 B1 | 2/2001 | Köster | 435/6 |
| 6,194,180 B1 | 2/2001 | Joyce | 435/91.31 |
| 6,197,498 B1 | 3/2001 | Koster | |
| 6,200,756 B1 | 3/2001 | Herman et al. | |
| 6,207,370 B1 | 3/2001 | Little et al. | |
| 6,214,556 B1 | 4/2001 | Olek et al. | |
| 6,221,605 B1 | 4/2001 | Koster | |
| 6,225,450 B1 | 5/2001 | Köster | 536/22.1 |
| 6,235,478 B1 | 5/2001 | Köster | 435/6 |
| 6,238,871 B1 | 5/2001 | Köster | 435/6 |
| 6,258,538 B1 | 7/2001 | Köster et al. | 435/6 |
| 6,265,167 B1 | 7/2001 | Carmichael et al. | 435/6 |
| 6,265,171 B1 | 7/2001 | Herman et al. | |
| 6,265,716 B1 | 7/2001 | Hunter et al. | |
| 6,268,131 B1 | 7/2001 | Kang et al. | |
| 6,270,835 B1 | 8/2001 | Hunt et al. | |
| 6,271,037 B1 * | 8/2001 | Chait et al. | 436/89 |
| 6,277,573 B1 | 8/2001 | Koster et al. | |
| 6,297,006 B1 | 10/2001 | Drmanac et al. | |
| 6,300,076 B1 | 10/2001 | Koster | |
| 6,309,833 B1 | 10/2001 | Edman et al. | |
| 6,322,970 B1 | 11/2001 | Little et al. | |
| 6,326,174 B1 | 12/2001 | Joyce et al. | 435/91.31 |
| 6,331,427 B1 | 12/2001 | Robison | 435/226 |
| 6,383,775 B1 | 5/2002 | Duff et al. | 435/69.1 |
| 6,423,966 B2 | 7/2002 | Hillenkamp et al. | |
| 6,428,955 B1 | 8/2002 | Koster et al. | |
| 6,436,635 B1 | 8/2002 | Fu et al. | |
| 6,440,705 B1 | 8/2002 | Stanton, Jr. et al. | 435/91.2 |
| 6,475,736 B1 | 11/2002 | Stanton, Jr. | |
| 6,475,807 B1 | 11/2002 | Geysen et al. | |
| 6,500,621 B2 | 12/2002 | Koster | |
| 6,522,477 B2 | 2/2003 | Anhalt | |
| 6,537,746 B2 | 3/2003 | Arnold et al. | |
| 6,558,902 B1 | 5/2003 | Hillenkamp | |
| 6,566,055 B1 | 5/2003 | Monforte et al. | |
| 6,569,385 B1 | 5/2003 | Little et al. | |
| 6,589,485 B2 | 7/2003 | Koster | |
| 6,602,662 B1 | 8/2003 | Koster et al. | |
| 6,884,586 B2 | 4/2005 | Van Ness | |
| 6,994,960 B1 | 2/2006 | Foote et al. | |
| 6,994,969 B1 | 2/2006 | Zabeau et al. | |
| 2001/0008615 A1 | 7/2001 | Little et al. | |
| 2002/0009394 A1 | 1/2002 | Koster et al. | |
| 2002/0042112 A1 | 4/2002 | Koster et al. | |
| 2002/0120127 A1 | 8/2002 | Church et al. | |
| 2002/0155587 A1 | 10/2002 | Opalsky et al. | |
| 2003/0013099 A1 | 1/2003 | Lasek et al. | |
| 2003/0017483 A1 | 1/2003 | Ecker et al. | |
| 2003/0027169 A1 | 2/2003 | Zhang et al. | |
| 2003/0082600 A1 | 5/2003 | Olek et al. | |
| 2003/0087235 A1 | 5/2003 | Darikee et al. | |
| 2003/0129589 A1 | 7/2003 | Koster et al. | |
| 2003/0180748 A1 | 9/2003 | Braun et al. | |
| 2003/0180749 A1 | 9/2003 | Koster et al. | |
| 2003/0180779 A1 | 9/2003 | Lofton-Day et al. | |
| 2003/0190644 A1 | 10/2003 | Braun et al. | |
| 2004/0014101 A1 | 1/2004 | Liu et al. | |
| 2004/0029258 A1 | 2/2004 | Heaney et al. | |
| 2004/0253141 A1 | 12/2004 | Schembri et al. | |
| 2005/0009053 A1 | 1/2005 | Boecker et al. | |
| 2005/0009059 A1 | 1/2005 | Shapero | |
| 2005/0019762 A1 | 1/2005 | Olek | |
| 2005/0026183 A1 | 2/2005 | Fan et al. | |
| 2005/0064406 A1 | 3/2005 | Zabarovsky | |
| 2005/0064428 A1 | 3/2005 | Berlin | |
| 2005/0069879 A1 | 3/2005 | Berlin | |
| 2005/0089904 A1 | 4/2005 | Beaulieu et al. | |
| 2005/0112590 A1 | 5/2005 | van den Boom et al. | |
| 2005/0153316 A1 | 7/2005 | Jeddeloh | |
| 2005/0153347 A1 | 7/2005 | Shapero | |
| 2005/0164246 A1 | 7/2005 | Fan et al. | |
| 2005/0272070 A1 | 12/2005 | Ehrich et al. | |
| 2006/0073501 A1 | 4/2006 | van den Boom et al. | |
| 2006/0210992 A1 | 9/2006 | van den Boom et al. | |
| 2006/0252061 A1 | 11/2006 | Zabeau et al. | |

FOREIGN PATENT DOCUMENTS

| | | |
|---|---|---|
| EP | 0 269 520 A2 | 1/1988 |
| EP | 0296781 | 6/1988 |
| EP | 0299652 | 7/1988 |
| EP | 0332435 | 9/1989 |
| EP | 0395481 | 4/1990 |
| EP | 0596205 | 5/1994 |
| EP | 1197567 | 4/2002 |
| EP | 1179589 | 12/2002 |
| FR | 2749662 | 12/1997 |
| GB | 2329475 | 8/1998 |
| JP | 2003-245087 | 9/2003 |
| WO | 92/13969 A1 | 8/1992 |
| WO | WO 93/15407 | 8/1993 |
| WO | WO 93/21592 | 10/1993 |
| WO | 94/00562 A1 | 1/1994 |
| WO | WO 94/15219 | 7/1994 |
| WO | WO 94/16101 | 7/1994 |
| WO | 94/21663 A1 | 9/1994 |
| WO | WO 94/21822 | 9/1994 |
| WO | WO 95/25281 | 9/1995 |
| WO | 96/29431 A2 | 9/1996 |
| WO | 96/29431 A3 | 9/1996 |
| WO | WO 96/32504 | 10/1996 |
| WO | WO 96/36732 | 11/1996 |
| WO | WO 96/36986 | 11/1996 |
| WO | 97/03210 A1 | 1/1997 |
| WO | WO 97/03210 * | 1/1997 |
| WO | WO 97/08306 | 3/1997 |
| WO | WO 97/08308 | 3/1997 |
| WO | 97/33000 A1 | 9/1997 |
| WO | 97/37041 A2 | 10/1997 |
| WO | 97/37041 A3 | 10/1997 |
| WO | WO 97/40462 | 10/1997 |
| WO | WO 97/42348 | 11/1997 |
| WO | WO 97/43617 | 11/1997 |
| WO | 98/12355 A1 | 3/1998 |
| WO | WO 98/12734 | 3/1998 |

| | | | |
|---|---|---|---|
| WO | 98/20020 A2 | 5/1998 |
| WO | 98/20020 A3 | 5/1998 |
| WO | 98/20166 A2 | 5/1998 |
| WO | 98/20166 A3 | 5/1998 |
| WO | WO 98/20019 | 5/1998 |
| WO | WO 98/20453 | 5/1998 |
| WO | WO 98/24935 | 6/1998 |
| WO | WO 98/33808 | 8/1998 |
| WO | WO 98/35609 | 8/1998 |
| WO | 98/54571 A1 | 12/1998 |
| WO | 99/54751 A1 | 12/1998 |
| WO | WO 99/05323 | 2/1999 |
| WO | WO 99/12040 | 3/1999 |
| WO | WO 99/31278 | 6/1999 |
| WO | 99/54501 A1 | 10/1999 |
| WO | WO 99/50447 | 10/1999 |
| WO | 99/57318 A2 | 11/1999 |
| WO | 99/57318 A3 | 11/1999 |
| WO | 00/18967 A1 | 4/2000 |
| WO | WO 00/22130 | 4/2000 |
| WO | WO 00/31300 | 6/2000 |
| WO | WO 00/51053 | 8/2000 |
| WO | WO 00/56446 | 9/2000 |
| WO | WO 00/66771 | * | 9/2000 |
| WO | 00/60361 A2 | 10/2000 |
| WO | 00/60361 A3 | 10/2000 |
| WO | WO 00/06771 | 11/2000 |
| WO | WO 01/27857 | 4/2001 |
| WO | WO 01/55455 | 8/2001 |
| WO | WO 02/13122 | 2/2002 |
| WO | WO 02/25567 | 3/2002 |
| WO | WO 02/086163 | 10/2002 |
| WO | WO 02/086794 | 10/2002 |
| WO | WO 02/101353 | 12/2002 |
| WO | WO 03/000926 | 1/2003 |
| WO | WO 03/002760 | 1/2003 |
| WO | WO 03/031649 | 4/2003 |
| WO | WO 03/038121 | 5/2003 |
| WO | WO 03/057909 | 7/2003 |
| WO | WO 03/080863 | 10/2003 |
| WO | WO 2004/013284 | 2/2004 |
| WO | WO 2004/050839 | 6/2004 |
| WO | WO 2004/097369 | 11/2004 |
| WO | WO 2005/040399 | 5/2005 |
| WO | WO 2005/093095 | 10/2005 |

OTHER PUBLICATIONS

Muller et al. 2000. Retention of imprinting of the human apoptosis-related gene TSSC3 in human brain tumors. Human Molecular Genetics, vol. 9, No. 5, pp. 757-763.*

Anderson, S., "Shotgun DNA sequencing using cloned DNase I-generated fragments" *Nucleic Acids Res.*, 9(13): 3015-3027 (1981).

Anker, R. et al., "Tetranucleotide repeat polymorphism at the human thyroid peroxidase (hTPO) locus", *Hum. Mol. Genet.*, 1(2): 137 (1992).

Banerjee, A. et al., "inhA, a gene encoding a target for isoniazid and ethionamide in *Mycobacterium tuberculosis*", *Science*, 263(5144): 227-230 (1994).

Barlow, D.P. and H. Lehrach, "Genetics by gel electrophoresis: the impact of pulsed field gel electrophoresis on mammalian genetics", *Trends Genet.*, 3: 167-171 (1987).

Beckmann, J.S. and J.L. Weber, "Survey of human and rat microsatellites", *Genomics*, 12: 627-631 (1992).

Berkenkamp, S. et al., "Ice as a Matrix for IR-Matrix-Assisted Laser Desorption/Ionization: Mass Spectra from a Protein Single Crystal", *Proc. Natl. Acad. Sci. U.S.A.*, 93(14): 7003-7007 (1996).

Bessho, T., "Nucleotide excision repair 3' endonuclease XPG stimulates the activity of base excision repair enzyme thymine glycol DNA glycosylase", *Nucleic Acids Res.*, 27(4): 979-983 (1999).

Biemann, K., "Sequencing of Peptides by Tandem Mass Spectrometry and High-Energy Collision-Induced Dissociation", *Methods in Enzymol.*, 193: 455-479 (1990).

Bird, A., "DNA methylation patterns and epigenetic memory", *Genes and Development*, 16(1): 6-21 (2002).

Bjelland, S. and E. Seeberg, "Purification and characterization of 3-methyladenine DNA glycosylase I from *Escherichia coli*", *Nucleic Acids Res.*, 15(7): 2787-2801 (1987).

Bocker, S., "SNP and mutation discovery using base-specific cleavage and MALDI-TOF mass spectrometry", *Bioinformatics*, 19: i44-i53 (2003).

Boguski, M.S. et al., "Identification of a Cytidine-specific Ribonuclease from Chicken Liver", *J. Biol. Chem.*, 255(5): 2160-2163 (1980).

Braun, A. et al., "Improved Analysis of Microsatellites Using Mass Spectrometry", *Genomics*, 46(1):18-23 (1997).

Browne, K. A., "Metal ion-catalyzed nucleic Acid alkylation and fragmentation", *J. Am. Chem. Soc.*, 124(27): 7950-7962 (2002).

Cannistraro, V.J. and D. Kennell, "Purification and characterization of ribonuclease M and Mrna degradation in *Escherichia coli*", *Eur. J. Biochem.*, 181(2): 363-370 (1989 ).

Caskey, C. T. et al., "Triplet Repeat Mutations in Human Disease", *Science* 256(5058): 784-789 (1992).

Chait, B.T. and S.B.H. Kent, "Weighing Naked Proteins: Practical, High-Accuracy Mass Measurement of Peptides and Proteins", *Science*, 257(5078): 1885-1894 (1992).

Chakrabarti, L. et al., "Sequence of simian immunodeficiency virus from macaque and its relationship to other human and simian retroviruses", *Nature*, 328(6130): 543-547 (1987).

Chung, M.H. et al., "An endonuclease activity of *Escherichia coli* that specifically removes 8-hydroxyguanine residues from DNA", *Mutat. Res.*, 254(1): 1-12, (1991).

Cleveland, D.W. et al., "Peptide Mapping by Limited Proteolysis in Sodium Dodecyl Sulfate and Analysis by Gel Electrophoresis", *J. Biol. Chem.*, 252(3): 1102-1106 (1977).

Dausset, J. et al., "Centre d'Etude du Polymorphisme Humain (CEPH): Collaborative Genetic Mapping of the Human Genome", *Genomics*, 6(3): 575-577 (1990).

Donis-Keller, H. et al., : Mapping adenines, guanines, and pyrimidines in RNA, *Nucleic Acids Res.*, 4(8): 2527-2537 (1977).

Donis-Keller, H., "Phy M.: an RNase activity specific for U and A residues useful in RNA sequence analysis", *Nucleic Acids Res.*, 8(14): 3133-3142 (1980).

Dunham, I. et al., "The DNA sequence of human chromosome 22", *Nature*, 402(6761): 489-495 (1999).

Edwards, M.C. et al., "Pentanucleotide repeat length plymorphism at the human CD4 locus", *Nucleic Acids Res.*, 19(17): 4791 (1991).

Eftedal, I. et al., "Consensus sequences for good and poor removal of uracil from double stranded DNA by uracil-DNA glycosylase", *Nucleic Acids Res.*, 21(9): 2095-2101 (1993).

Ehrlich, S.D. et al., "Studies on acid deoxyribonuclease. IX. 5'-hydroxy-terminal and penultimate nucleotides of oligonucleotides obtained from calf thumus deoxyribonucleic acid", *Biochemistry*, 10(11): 2000-2009 (1971).

German, J. and E. Passarge, "Bloom's Syndrome. XII. Report from the Registry for 1987", *Clin. Genet.*, 35: 57-69 (1989).

Germino, J. and D. Bastis, "Rapid purification of a cloned gene product by genetic fusion and site-specific proteolysis", *Proc. Natl. Acad. Sci. U.S.A.*, 81(15):4692-(1984).

Gogos, J.A. et al., "Detection of single base mismatches of thymine and cytosine residues by potassium permanganate and hydroxylamine in the presence of tetralky'lammonium salts.", *Nucleic Acids Res.*, 18(23): 6807-6817 (1990).

Gupta, R.C. and K. Randerath, "Use of specific endonuclease cleavage in RNA sequencing", *Nucleic Acids Res.*, 4(6):1957-1978 (1977).

Gust, I.D. et al., "Taxomonic classifcation of Hepatitis A virus", *Intervirology*, 20: 1-7 (1983).

Gut, I. G. and S. Beck, "A procedure for selective DNA alkylation and detection by mass spectrometry", *Nucleic Acids Res.*, 23(8): 1367-1373 (1995).

Guyader, M. et al., "Genome organization and transactivation of the human immunodeficiency virus type 2", *Nature*, 326(6114): 662-669 (1987).

Haff, L. and I.P. Smirnov, "Single-Nucleotide Polymorphism Identification Assays Using a Thermostable DNA Polymerase and Delayed Extraction MALDI-TOF Mass Spectrometry", *Genome Res.*, 7: 378-388, (1997).

Haffey, M. L. et al., "Site-specific cleavage of a fusion protein by renin", *DNA*, 6(6): 565-571 (1987).

Hahner, S. et al., "Matrix-assisted laser desorption/ionization mass spectrometry (MALDI) of endonuclease digests of RNA", *Nucleic Acids Res.*, 25(10): 1957-1964 (1997).

Hanish, J. and M. McClelland, "Activity of DNA modification and restriction enzymes in KGB, a potassium glutamate buffer Gene", *Gene. Anal. Tech.*, 5: 105-107 (1988).

Harrington, J.J. and M.R. Lieber, "Functional domains within FEN-1 and RAD2 define a family of structure- specific endonucleases: implications for nucleotide excision repair", *Genes and Develop.*, 8(11): 1344-1355 (1994).

Hartmer, R. et al., "RNase T1 mediated base-specific cleavage and MALDI-TOF for high-throughput comparative sequence analysis", *Nucleic Acids Res.*, 31(9): e47 pp. 1-10 (2003).

Heym, B. et al., "Implications of multidrug resistance for the future of short-course chemotherapy of tuberculosis: a molecular study", *Lancet*, 344(8918): 293-298 (1994).

Hillenkamp, F. and M. Karas, "Matrix-assisted laser desorption/ionization mass spectrometry of biopolymers", *Anal. Chem.*, 63(24): 1193A-1202A (1991).

Hsu, I-C. et al., "Detection of DNA point mutations with DNA mismatch repair enzymes", *Carcinogenesis*, 15(8): 1657-1662 (1994).

Huang, Z.-H. et al., "Protein Sequencing by Matrix-Assisted Laser Desorption Ionization—Postsource Decay—Mass Spectrometry Analysis of the N-Tris(2,4,6-trimethoxyphenyl)phosphine-Acetylated Tryptic Digests", *Anal. Biochem.*, 268(2): 305-317 (1999).

Jahnen et al., "Internal amino acid sequencing of proteins by in situ cyanogen bromide cleavage in polyacrylamide gels", *Biochem. Biophys. Res. Commun.*, 166(1): 139-145 (1990).

Jeffreys et al., "Hypervariable 'minisatellite' regions in human DNA", *Nature*, 314: 67-73 (1985).

Johnson, R. S. et al., "Collision-induced fragmentation of (M + H)+ ions of peptides. Side chain specific sequence ions", *Intl. J. Mass Spectrom. Ion Processes*, 86: 137-154 (1988).

Jurinke, C. et al., "The use of MassARRAY technology for high throughput genotyping" *Adv. Biochem. Eng. Biotechnol.*, 77: 57-74 (2002).

Jurinke, C. et al., "Automated genotyping using the DNA MassArray technology", *Methods Mol. Biol.*, 187: 179-192 (2002).

Köster, H. et al., "A strategy for rapid and efficient DNA sequencing by mass spectrometry", *Nat. Biotechnol.*, 14(9): 1123-1128 (1996).

Kruglyak, L. and D.A. Nickerson, "Variation is the spice of life", *Nat. Genet.*, 27(3): 234-236 (2001).

Kuchino, Y. and S. Nishimura, "Enzymatic RNA Sequencing", *Methods Enzymol.*, 180: 154-163 (1989).

Kwok et al., "Effects of primer-template mismatches on the polymerase chain reaction: human immunodeficiency virus type 1 model studies", *Nucl. Acids Res.*, 18(4): 999-1005 (1990).

Lai, E. et al., "A 4-Mb High-Density Single Nucleotide Polymorphism-Based Map around Human APOE", *Genomics*, 54(1): 31-38 (1998).

Litt, M. and J.A. Luty, "Dinucleotide repeat polymorphism at the D6S89 locus", *Nucleic Acids Res.*, 18(14): 4301 (1990).

Litt, M. et al., "Dinucleotide repeat polymorphism at the D11S35 locus", *Nucleic Acids Res.*, 18(19): 5921 (1990).

Little, D. P. et al., "Mass spectrometry from miniaturized arrays for full comparative DNA analysis", *Nat. Med.*, 3(12): 1413-1416 (1997).

Lu, A.-L. and I.-C. Hsu, "Detection of Single DNA Base Mutations with Mismatch Repair Enzymes", *Genomics*, 14(1): 249-255 (1992).

Luty, J.A. et al., "Five Polymorphic Microsatellite VNTRs on the Human X Chromosome", *Am. J. Hum. Genet.*, 46: 776-783 (1990).

Luty, J.A. and M. Litt, "Dinucleotide repeat polymorphism at the D14S45 locus", *Nucleic Acids Res.*, 19(15): 4308 (1991).

Marotta, C.A. et al., "Preferred sites of digestion of a ribonuclease from Enterobacter species in the sequence analysis of *Bacillus stearothermophilus* 5S ribonucleic acid", *Biochemistry*, 12(15): 2901-2904 (1973).

Maxam, A.M. and W. Gilbert, "A new method for sequencing DNA", *Proc. Natl. Acad. Sci. U.S.A.*, 74(2): 560-564 (1977).

McClelland, M. et al., "A single buffer for all restriction endonucleases", *Nucleic Acid Res.*, 16(1): 364 (1988).

McKinnon, P.J., "Ataxia-telangiectasia: an inherited disorder of ionizing-radiation sensitivity in man. Progress in the elucidation of the underlying biochemical defect", *Hum. Genet.*, 75(3): 197-208 (1987).

McLafferty, F.W., "High-resolution tandem FT mass spectrometry above 10 kDa", *Acc. Ch, em. Res.*, 27(11): 379-386 (1994).

Morris et al., "Molecular Mechanisms of Multiple Drug Resistance in Clinical Isolates of *Mycobacterium tuberculosis*", *J. Infect. Dis.*, 171: 954-960 (1995).

Murante, R. S. et al., "The Calf 5'-to 3'-Exonuclease is Also an Endonuclease with Both Activities Dependent on Primers Annealed Upstream of the Point of Cleavage", *J. Biol. Chem.*, 269(2): 1191-1196 (1994).

Nagai, K. and H. C.Thogersen, "Generation of beta-globin by sequence-specific proteolysis of a hybrid protein produced in *Escherichia coli*", *Nature*, 309: 810-812 (1984).

Nakamura, Y. et al., "Variable Number of Tandem Repeat (VNTR) Markers for Human Gene Mapping", *Science*, 235: 1616-1622 (1987).

Nikodem, V. and J.R. Fresco, "Protein Fingerprinting by SDS-Gel Electrophoresis after Partial Fragmentation with CNBr", *Anal. Biochem.*, 97(2): 382-386 (1979).

Nishimura, D.Y. and J.C. Murray, "A tetranucleotide repeat for the F13B locus", *Nucleic Acids Res.*, 20(5): 1167 (1992).

Nordhoff, E. et al., "Ion stability of nucleic acids in infrared matrix-assisted laser desorption/ionization mass spectrometry", *Nucleic Acids Res.*, 21(15): 3347-3357 (1993).

Perlman, P.S. and R.A. Butow, "Mobile Introns and Intron-Encoded Proteins", *Science*, 246(4934): 1106-1109 (1989).

Ploos et al., "Tetranucleotide repeat polymorphism in the vWF gene", *Nucleic Acids Res.*, 18(16): 4957 (1990).

Polymeropoulos, M.H. et al., , *Nucl. Acids Res.*, 18(24): 7468 (1990).

Polymeropoulos et al., "Tetranucleotide repeat polymorphism at the human aromatase cytochrome P-450 gene (CYP19)", *Nucl. Acids Res.*, 19(1): 195 (1991).

Polymeropoulos, M.H. et al., "Tetranucleotide repeat polymorphism at the human c-fes/fps proto-oncogene (FES)", *Nucleic Acids Res.*, 19(14): 4018 (1991).

Polymeropoulos, M.H. et al., *Nucl. Acids Res.*, 19(15): 4306 (1991).

Ratner, L. et al., "Complete nucleotide sequence of the AIDS virus, HTLV-III", *Nature*, 313: 227-284 (1985).

Reymer, P.W.A. et al., "A lipoprotein lipase mutation (Asn291Ser) is associated with reduced HDL cholesterol levels in premature atherosclerosis", *Nature Gen.*, 10: 28-34 (1995).

Rodi, C.P. et al., "A strategy for the rapid discovery of disease markers using the MassARRAY system", *BioTechniques*, 32: S62-S69 (2002).

Rojo, M.A. et al., "Cusativin, a new cytidine-specific ribonuclease accumulated in seeds of *Cucumis sativus* L"; *Planta*, 194: 328-338 (1994).

Ross, P. et al., "High level multiplex genotyping by MALDI-TOF mass spectrometry", *Nat. Biotechnol.*, 16(13): 1347-1351 (1998).

Santoro, S. W. and G. F. Joyce, "A general purpose RNA-cleaving DNA enzyme", *Proc. Natl. Acad. Sci. U.S.A.*, 94(9): 4262-4266 (1997).

Saparbaev, M. et al., "*Escherichia coli, Saccharomyces cerevisiae*, rat and human 3-methyladenine DNA glycosylases repair 1,N6-ethenoadenine when present in DNA", *Nucleic Acids Res.*, 23(18): 3750-3755 (1995).

Sargent, T.D. et al., "Isolation of Differentially Expressed Genes", *Methods Enzymol.*, 152: 423-432 (1987).

Saris, C.J.M. et al., "Hydroxylamine Cleavage of Proteins in Polyacrylamide Gels", *Anal. Biochem.*, 132(1): 54-67 (1983).

Schachter, F. et al., "Genetic associations with human longevity at the APOE and ACE loci", *Nat. Gen.*, 6: 29-32 (1994).

Seela, F. and A. Kehne, "Palindromic octa- and dodecanucleotides containing 2'-deoxytubercidin: synthesis, hairpin formation, and recognition by the endodeoxyribonuclease EcoRI", *Biochemistry*, 26(8): 2232-2238 (1987).

Sequenom, Application Notes from company website: "SNP Discovery Using theMassARRAY System", http://www.sequenom.com/Assets/pdfs/appnotes/SNP_Discovery_Application_Note.pdf (accessed on Jun. 29, 2004).

Shchepinov et al., "Matrix-induced fragmentation of P3'-N5'-phosphoroamidate-containing DNA: high-throughput MALDI-TOF analysis of genomic sequence polymorphisms", *Nucleic Acids Res.*, 29(18): 3864-3872 (2001).

Simoncsits et al., "New rapid gel sequencing method for RNA", *Nature*, 269: 833-836 (1977).

Siuzdak, G., "The emergence of mass spectrometry in biochemical research", *Proc. Natl. Acad. Sci*, U.S.A., 91(24): 11290-11297 (1994).

Smith, D. B. and K. S. Johnson, "Single-step purification of polypeptides expressed in *Escherichia coli* as fusions with glutathione S-transferase", *Gene*, 67: 31-40 (1988).

Springer, B. et al., "Two-laboratory collaborative study on identification of mycobacteria: molecular versus phenotypic methods", *J. Clin. Microbiol.*, 34(2): 296-303 (1996).

Stevens, A., "Pyrimidine-specific cleavage by an endoribonuclease of *Saccharomyces cerevisiae*", *J. Bacteriol.*, 164(1): 57-62 (1985).

Stults, J. T. et al., "Simplification of high-energy collision spectra of peptides by amino-terminal derivatization", *Anal. Chem.*, 65(13): 1703-1708 (1993).

The International SNP Map Working Group, "A Map of human genome sequence variation containing 1.42 million single nucleotide polymorphisms", *Nature*, 409(6822): 928-933 (2001).

Tang, K. et al., "Chip-based genotyping by mass spectrometry", *Proc. Natl. Acad. Sci. U.S.A.*, 96(18): 10016-10020 (1999).

Tautz, D., "Hypervariability of simple sequences as a general source for polymorphic DNA markers . . . ", *Nucleic Acids Res.*, 17(16): 6463-6471 (1989).

Vanfleteren, J.R. et al., "Peptide Mapping and Microsequencing of Proteins Separated by SDS-PAGE After Limited In Situ Acid Hydrolysis", *BioTechniques*, 12(4): 550-557 (1992).

Vath, J. E. et al., "Method for the derivatization of organic compounds at the sub-nanomole level with reagent vapor", *Fresenius' Zeitschrift für analytische Chemie*, 331: 248-252 (1988).

von Wintzingerode, F. et al., "Base-specific fragmentation of amplified 16S rRNA genes analyzed by mass spectrometry: A tool for rapid bacterial identification", *Proc. Natl. Acad. Sci. U.S.A.*, 99(10): 7039-7044 (2002).

von Wintzingerode, F. et al., "Phylogenetic Analysis of an Anaerobic, Trichlorobenzene-Transforming Microbial Consortium", *Appl. Environ. Mcrobiol.*, 65(1): 283-286 (1999).

Wagner, D. S. et al., "Derivatization of Peptides to Enhance Ionization Effiency and Control Fragmentation During Analysis by Fast Atom Bombardment Tandem Mass Spectrometry", *Biol. Mass Spectrom.*, 20(7): 419-425 (1991).

Wain-Hobson, S. et al., "Nucleotide sequence of the AIDS virus, LAV", *Cell*, 40: 9-17 (1985).

Wang, D.G. et al., "Large-scale identification, mapping, and genotyping of single-nucleotide polymorphisms in the human genome", *Science*, 280: 1077-1082 (1998).

Weber, J.L and P.E. May, "Abundant class of human DNA polymorphisms which can be typed using the polymerase chain reaction", *Am. J. Hum. Genet.*, 44: 388-396 (1989).

Weissenbach, J. et al. , "A second-generation linkage map of the human genome", *Nature*, 359(6398): 794-801 (1992).

Yule, A., "Amplification-Based Diagnosis Target TB", *Bio/Technology*, 12: 1335-1337 (1994).

Zaia, J. and K. Biemann, "Comparison of Charged Derivatives for High Energy Collision-Induced Dissociation Tandem Mass Spectrometry", *J. Am. Soc. Mass Spectrom.*, 6(5): 428-436 (1995).

Zaia, J., in: *Protein and Peptide Analysis by Mass Spectrometry*, J. R. Chapman (ed.), pp. 29-41, Humana Press, Totowa, N. J., (1996).

Zuliani, G. and H.H. Hobbs, "Tetranucleotide repeat polymorphism in the LPL gene", *Nucleic Acids Res.*, 18(16): 4958 (1990).

Red Tape; It's in You to Give: Ottawa Citizen Saturday Final Edition Oct. 5, 2002.

Risch and Ten., Genome Research,(1998), 8:1273-1288.

Robertson et al., Nature Rev. Genet. 1:11-19 (2000).

Ross et al., Analytical Chemistry 69:4197-4202 (1997).

Ross et al., Analytical Chemistry 69:3966-3972 (1997).

Ross, et al., BioTechniques, (2000) 29(3):620-629.

Ruppert et al.,Anal. Biochem., 230:130-134 (1995).

Samson et al., Nature, 382:722-725 (1996).

Sarkar et al. , Moire Inst. Oswaldo Cruz, 93(51:693-694 (1998).

Sarkar et al., Analytical Biochemistry 186:64-68 (1990).

Sarkar et al., Biotechniques 10(4):436-440 (1991).

Sasaki, et al., Am. J. Hum, Genet. (2001) 68:214-218.

Scott et al., J. Biol. Chem., 265(35):21561-21566 (1990).

Scott, J., 50:123-145(1991).

Senko et al., J. Am. Soc. Mass Spectrom., 6:52-56 (1995).

Senter et al., Photochem. Photobiol., 42:231-237 (1985).

Shriner et al., Am. J. Hum. Genet., 60:957-964 (1997).

Siegert et al., Anal. Biochem., 24 :55-65 (1996).

Smith, L.M., Nature Biotechnology, 14:1084-1085 (1996).

Sommer et al., Biotechniques, 12(1):82-87 (1992).

SpectroCHIP BioArray , Sequenom Product Advertisement.

Srinivasan et al. , Rapid Communications in Mass Spectrometry, 11:1144-1150 (1997).

Stanssens et al., Genomic Res., 14:126-133 (2004).

Sugisaki et al., Gene, 16:73-78 (1981).

Szybalski et al., Gene, 100:13-26 (1991).

Takio et al., Proc. Natl. Acad. Sci. USA, 79:2644-8(1982).

Tammen et al.,, J. Cromatogr. A. 852:285-295.

Tang et al., Nucl. Acids Res., 23(16):3126-3131 (1995).

Tang et al., Int. J. Mass. Spectrometry, 226(1):37-54 (2003).

Taranenko et al, Genetic Analysis: Biomolecular Engineering. 13:87-94 (1996).

Thompson, Laboratory Automation and Information Management, 31:173-193 (1996).

Tost et al., Nucl. Acid Res., 31:C50 (2003).

van den Boom et al., Anal. .Biochem., 256:127-129 (1998).

Tang et al., "Matrix-assisted Laser Desorption/Ionization of Restriction Enzyme-digested DNA," Rapid Communication in Mass Spectrometry, v. 8, pp. 183-186, 1994.

Aurup et al., Biochemistry, 31: 9636-9641 (1992).

Bachem et al., The Plant Journal, 9: 745-753 (1996).

Bonnin et al., J. Mol. Biol., 290: 241-251 (1999).

Bullinger, L., "Gene Expression Profiling in Acute Myloid Leukemia," J. Clinical Oncology. Sep. 10, 2005, vol. 23, No. 26, pp. 6296-6305.

Clayton et al., Curr. Opin. Microbiol., 1: 562-566 (1998).

Conrad et al., Nucleic Acids Res., 23: 1845-1853 (1995).

Contreras et al., FEBS Lett., 16: 281-283 (1971).

Crain et al., Curr. Opin. in Biotechnol., 9: 25-34 (1998).

Eckstein, Ann. Rev. Biochem., 54: 367-402 (1985).

Eng et al., Nature Biotechnol., 15: 422-426 (1997).

Fleischmann et al., Science, 269: 496-512 (1995).

Frommer et al., "A Genomic Sequencing Protocol that Yields a Positive Display of 5-Methylcytosine Residues in Individual DNA Strands," PNAS, vol. 89, Mar. 1, 1992 p. 1827-1831.

Gao et al., Proc. Natl. Acad. Sci. USA, 94: 407-411 (1997).

Gish et al., Nucleic Acids Symp. Ser., pp. 253-256 (1987).

Gish et al., Science, 240: 1520-1522 (1988).

Hertogs et al., Animicrob. Agents Chemother., 42: 269-276 (1998).

International Search Report and Written Opinion received in PCT/US2006/30256 mailed on: Aug. 14, 2008.

Isola et al., Anal. Chem., 71: 2266-2269 (1999).

Ivanova et al., Nucleic Acids Res., 23: 2954-2958 (1995).

Kato, Nucleic Res., 23: 3685-3690 (1995).

Lander et al., Science, 265: 2037-2048 (1994).

Lee et al.; Proc. Natl. Acad. Sci. USA, 92: 8303-8307 (1995).

Liang et al., Science, 257: 967-971 (1992).

Limbach, Mass Spectrom. Rev., 15: 297-336 (1996).

Lipshutz et al., Curr. Opin. in Struct. Biol., 4: 376-380 (1994).

Little et al., J. Am. Chem. Soc., 116: 4893-4897 (1994).

Loverix et al., Nature Struct. Biol., 5: 365-368 (1998).

Meador et al., Eur. J. Biochem., 187: 549-553 (1990).

Milligan et al., Nucleic Acids Res., 15: 8783-8798 (1987).
Murray, J. Mass Spectrom, 31: 1203-1215 (1996).
New England BioLabs Catalog, T4 DNA polymerase, T7 RNA polymerase, pp. 74-75, 1996/1997.
Nickerson et al., Nature Genet., 19: 233-240 (1998).
Nordhoff et al., J. Mass Spectrom., 30: 99-112 (1995).
Office Action mailed: Jan. 15, 2008 in U.S. Appl. No. 11/089,805, filed Mar. 24, 2005 Published as: US-2005-0272070 on Dec. 8, 2005.
Office Action mailed: Jan. 19, 2007 in U.S. Appl. No. 11/222,991, filed Sep. 8, 2005, Published as: US-2006-0073501A on Apr. 6, 2006.
Office Action mailed: Jan. 23, 2007 in U.S. Appl. No. 10/830,943, filed Apr. 22, 2004 Published as: US-2005-0009053A1 on Jan. 13, 2005.
Office Action mailed: Jan. 24, 2003 in U.S. Appl. No. 10/018,453, filed Oct. 30, 2001, Now U.S. Patent 6,994,969 Issued on: Feb. 7, 2006.
Office Action mailed: Jan. 27, 2006 in U.S. Appl. No. 10/272,665, filed Nov. 15, 2002 Published as: US-2003-0180748A1 on Sep. 25, 2003, now U.S. Patent 7,332,275 issued on Feb. 19, 2008.
Office Action mailed: Jan. 27, 2009 in U.S. Appl. No. 10/888,359, filed Jul. 9, 2004 Published as: US-2006-0210992A1 on Sep. 21, 2006.
Office Action mailed: Jan. 30, 2009 in U.S. Appl. No. 11/348,683, filed Feb. 7, 2006 Published as: US-2006-0252061A1 on Nov. 9, 2006.
Office Action mailed: Oct. 26, 2004 in U.S. Appl. No. 10/272,665, filed Nov. 15, 2002 Published as: US-2003-0180748A1 on Sep. 25, 2003, now U.S. Patent 7,332,275 issued on Feb. 19, 2008.
Office Action mailed: Oct. 9, 2007 in U.S. Appl. No. 10/830,943, filed Apr. 22, 2004 Published as: US-2005-0009053A1 on Jan. 13, 2005.
Office Action mailed: Dec. 12, 2005 in U.S. Appl. No. 10/723,365, filed Nov. 26, 2003 Published as: US-2005-0112590A1 on May 26, 2005.
Office Action mailed: Dec. 16, 2008 in U.S. Appl. No. 11/222,991, filed Sep. 8, 2005, Published as: US-2006-0073501A on Apr. 6, 2006.
Office Action mailed: Dec. 2, 2005 in U.S. Appl. No. 10/933,611, filed Sep. 2, 2004 Published as: US-2005-0089904A1 on Apr. 28, 2005.
Office Action mailed: Dec. 27, 2006 in U.S. Appl. No. 10/933,611, filed Sep. 2, 2004 Published as: US-2005-0089904A1 on Apr. 28, 2005.
Office Action mailed: Dec. 5, 2006 in U.S. Appl. No. 10/723,365, filed Nov. 26, 2003 Published as: US-2005-0112590A1 on May 26, 2005.
Office Action mailed: Dec. 8, 2008 in U.S. Appl. No. 10/723,365, filed Nov. 26, 2003 Published as: US-2005-0112590A1 on May 26, 2005.
Office Action mailed: Feb. 17, 2009 in U.S. Appl. No. 10/933,611, filed Sep. 2, 2004 Published as: US-2005-0089904A1 on Apr. 28, 2005.
Office Action mailed: Feb. 2, 2009 in U.S. Appl. No. 11/089,805, filed Mar. 24, 2005 Published as: US-2005-0272070 on Dec. 8, 2005.
Office Action mailed: Feb. 29, 2008 in U.S. Appl. No. 10/723,365, filed Nov. 26, 2003 Published as: US-2005-0112590A1 on May 26, 2005.
Office Action mailed: Feb. 6, 2009 in U.S. Appl. No. 10/830,943, filed Apr. 22, 2004 Published as: US-2005-0009053A1 on Jan. 13, 2005.
Office Action mailed: Mar. 31, 2008 in U.S. Appl. No. 11/348,683, filed Feb. 7, 2006 Published as: US-2006-0252061A1 on Nov. 9, 2006.
Office Action mailed: Mar. 8, 2006 in U.S. Appl. No. 10/723,365, filed Nov. 26, 2003 Published as: US-2005-0112590A1 on May 26, 2005.
Office Action mailed: Apr. 17, 2008 in U.S. Appl. No. 10/933,611, filed Sep. 2, 2004 Published as: US-2005-0089904A1 on Apr. 28, 2005.
Office Action mailed: Apr. 19, 2005 in U.S. Appl. No. 10/018,453, filed Oct. 30, 2001, Now U.S. Patent 6,994,969 Issued on: Feb. 7, 2006.
Office Action mailed: Apr. 2, 2008 in U.S. Appl. No. 11/222,991, filed Sep. 8, 2005, Published as: US-2006-0073501A on Apr. 6, 2006.
Office Action mailed: May 16, 2007 in U.S. Appl. No. 11/222,991, filed Sep. 8, 2005, Published as: US-2006-0073501A on Apr. 6, 2006.
Office Action mailed: May 2, 2007 in U.S. Appl. No. 11/089,805, filed Mar. 24, 2005 Published as: US-2005-0272070 on Dec. 8, 2005.
Office Action mailed: May 20, 2008 in U.S. Appl. No. 10/888,359, filed Jul. 9, 2004 Published as: US-2006-0210992A1 on Sep. 21, 2006.
Office Action mailed: Jun. 1, 2004 in U.S. Appl. No. 10/018,453, filed Oct. 30, 2001, Now U.S. Patent 6,994,969 Issued on: Feb. 7, 2006.
Office Action mailed: Jul. 11, 2007 in U.S. Appl. No. 11/089,805, filed Mar. 24, 2005 Published as: US-2005-0272070 on Dec. 8, 2005.
Office Action mailed: Jul. 17, 2008 in U.S. Appl. No. 10/830,943, filed Apr. 22, 2004 Published as: US-2005-0009053A1 on Jan. 13, 2005.
Office Action mailed: Jul. 3, 2007 in U.S. Appl. No. 10/888,359, filed Jul. 9, 2004 Published as: US-2006-0210992A1 on Sep. 21, 2006.
Office Action mailed: Jul. 6, 2005 in U.S. Appl. No. 10/272,665, filed Nov. 15, 2002 Published as: US-2003-0180748A1 on Sep. 25, 2003, now U.S. Patent 7,332,275 issued on Feb. 19, 2008.
Office Action mailed: Aug. 28, 2007 in U.S. Appl. No. 10/888,359, filed Jul. 9, 2004 Published as: US-2006-0210992A1 on Sep. 21, 2006.
Office Action mailed: Aug. 28, 2006 in U.S. Appl. No. 10/272,665, filed Nov. 15, 2002 Published as: US-2003-0180748A1 on Sep. 25, 2003, now U.S. Patent 7,332,275 issued on Feb. 19, 2008.
Office Action mailed: Sep. 2, 2008 in U.S. Appl. No. 10/830,943, filed Apr. 22, 2004 Published as: US-2005-0009053A1 on Jan. 13, 2005.
Office Action mailed: Sep. 20, 2007 in U.S. Appl. No. 10/272,665, filed Nov. 15, 2002 Published as: US-2003-0180748A1 on Sep. 25, 2003, now U.S. Patent 7,332,275 issued on Feb. 19, 2008.
Office Action mailed: Sep. 29, 2003 in U.S. Appl. No. 10/018,453, filed Oct. 30, 2001, Now U.S. Patent 6,994,969 Issued on: Feb. 7, 2006.
Parsons et al., Environmental and Molecular Mutagenisis, 1998, vol. 32, p. 200-2111.
Parsons et al., Mutagenesis, 1998, vol. 13, No. 6, p. 581-588.
Pieles et al., Nucleic Acids Res., 21: 3191-3196 (1993).
Prashar et al., Proc. Natl. Acad. Sci. USA, 93: 659-663 (1996).
Richterich et al., Nucleic Acids Res., 23: 4922-4923 (1995).
Risch et al., Science, 273: 1516-1517 (1996.
Sanger et al., Proc. Natl. Acad. Sci. USA, 74: 5463-5467 (1977).
Schena et al., Science, 270: 467-470 (1995).
Schinazi et al., Int. Antivir. News, 4: 95-107 (1996).
Sousa et al., Embol J. 14: 4609-4621 (1995).
Stevens, J. Bacteriol., 164: 57-62 (1985).
Steyaert, Eur. J. Biochem., 274: 1-11 (1997).
Stratagene Catalog (1998), p. 39. Published by Stratagene, 11011 North Torrey Pines Road, La Jolla, CA 92037, USA.
Supplemental European Search Report received in PCT/US2005/009929 mailed on Jan. 30, 2009.
Supplemental European Search Report received in PCT/US2005/032441 mailed on Nov. 28, 2008.
Tang et al., "Matrix-Assisted Laser Desorption/Ionization of Restriction Enzyme-digested DNA," Rapid Communications in Mass Spectrometry, vol. 8, pp. 183-186, 1994.
Tost et al., "Genotyping Single Nucleotide Polymorphisms by Mass Spectrometry," Mass Spectrometry Reviews, John Wiley and Sons, New York, vol. 21, No. 6, Nov. 1, 2002, p. 388-418.
Vos et al., Nucleic Acids Res., 23: 4407-4414 (1995).
Wodicka et al., Nature Biotechnol., 15: 1359-1367 (1997).
Chan et al., Oncogene, 2003, vol. 22, pp. 924-934.
Deng et al., Cancer Research, 1999, vol. 59, pp. 2029-2033.
Office Action mailed: Jun. 24, 2009 in U.S. Appl. No. 11/089,805, filed Mar. 24, 2005 Published as: US-2005-0272070 on Dec. 8, 2005.
Rand et al., Methods, 2002, vol. 22 (27), pp. 114-120.
Sakai et al., "Allele-Specific Hypermethylation of the Retinoblastoma Tumor-Supressor Gene," American Journal of Human Genetics, vol. 48, No. 5, 1991 pp. 880-888.
Stanssens et al., "High-throughput MALDI-TOF discovery of genomic sequence polymprphisms," Genome Research, vol. 14, No. 1, Jan. 2004, pp. 126-133.

Vaughn et al., Genetic Analysis: Biomolecular Engineering (1999) vol. 14, pp. 169-175.
Michalatos-Beloin et al., Nucleic Acids Research, 1996, 24(23):4841-4843.
Office Action mailed: Jan. 25, 2010 in U.S. Appl. No. 11/089,805, filed Mar. 24, 2005 Published as: US-2005-0272070 on Dec. 8, 2005.
Office Action mailed. Oct. 1, 2009 in U.S. Appl. No. 10/933,611, filed Sep. 2, 2004 Published as: US-2005-0089904A1 on Apr. 28, 2005.
Aebersold and Mann, Nature, 422:198-207 (2003).
Amir et al., Nature Genet. 23:185-188 (1999).
Arnheim et al., Proc. Natl. Acad. Sci. USA, 82:6970-6974 (1985).
Arrand et al., J. Biol. Chem., 261.(20):9079-9082 (1986).
Bader and Hogue, BMC Bioinformatics. Jan. 13, 2003;4:2, Epub Jan. 13, 2003. http://www.biomedcentral.com/1471-2105/4/2.
Badger et al., Proteins: Structure, Function, and Genetics, 35(11):25-33 (1999).
Bains and Smith, J. Theoret. Biol., 135:303-307 (1988).
Beaulieu et al., Am. J. Hum. Genet., 73(5):441- (2003).
Beck et al., Nucl. Acids Res., 17(13):5115-5123 (1989).
Bertina et al., Nature, 369:647 (1994).
Bleczinski et al., Rapid Communications in Mass Spectrometry, 12:1737-1743(1998).
Boecker, Lect. Notes Comp. Sci. 2818:476-487 (2003) (http://gi.cebitec.uni-bielefeld.de/people/boecker/download/Preprint_2003-04_Sequencing_SBoecker.pdf).
Boecker, Technical Report (http://gi.cebitec.uni-bielefeld.de/people/boecker/download/Preprint_2003-07_WeightedSC_SBoecker.pdf), (2003).
Braun et al., Clinical Chemistry, 43(7):1151-1158 (1997).
Breen, G., et al., BioTechniques, 28(3):464-470, (2000).
Bregman et al, J. Biol.Chem.. 266(11):7207-7213 (1991).
Buetow, et al., Proc. Natl. Acad. Sci. USA, (2001), 581-584, 98(2).
Burton et al., Proc. Natl. Acad. Sci. USA, 94:11067-11072 (1997).
Cai and Harrington., J. Chem. Inf. Comput. Sci 38: 1181-1170 (1998).
Caldwell and Joyce, PCR Methods and Applications 2:28-33 (1992).
Carr et al., J. Biol. Chem., 287(19):13376-13382 (1992).
Carr et al., J. Biol.Chem., 266(22):14188-14192 (1991).
Cavalli-Sforza, L.l.,Trends in Genetics 14(2): 60-65 (1998).
Chechetkin et al., Biomol. Struct. Dyn., 18(1):83-101 (2000).
Chiu et al, Clin. Chem., 45:1578 (1999).
Chiu et al., Nucl. Acids. Res., 28(8}:e31 (2000).
Clausen et al., J. Clinical Investigation, 98(5):1195-1209 (1996).
Clegg or al., Proc. Natl. Acad. Sci. USA, 85:3703-3707(1988).
Coghlan et al., Science, 267:108-111 (1995).
Cohen et al., Advanced Chromatography, 36:127-162 (1996).
Colledge et al., Trends in Cell Biology, 8:216-221(1999).
Collins et al., Genome Research, 8:1229-1231 (1998).
Corder et al., Science, 261:921-923 (1993).
Costello et al., Nature Genet., 24:132-138 (2000).
Database WPI, Derwent publication #007515331, (1988).
Database WPI, Derwent publication # 011635345, (1998).
Delagrave et al., Protein Engineering, 6:327-331 (1993).
Ding and Cantor, Proc. Natl. Acad. Sci. USA, 100(13):7449-7453 (2003).
Dittmar, M., Anthropol Anz. 53(4): 289-315 (1995).
Dodgson et al., Poultry Science 76: 1108-1114 (1997).
Downes, Kate, et al., BioTechniques, (2004), 840-845, 36(5).
Eggertsen et al., Clinical Chemistry 30(10):2125-2129 (1993).
Eitan et al., Nucleic Acids Res. 30(12):E62.1-E62.8 (2002).
Elso et al., Genome Res. 12(9):1428-1433 (2002).
Faux et al., Trends Biochem., 21:312-315 (1996).
Fei and Smith., Rapid Commun. Mass. Spectrom., 14(11):950-959 (2000).
Foster et al., Genome Research, 8:755-757 (1998).
Fu et al., Genetic Analysis:Biomolecular Engineering, 12:137-142 (1996).
Fu et al., Nature Biotechnol., 16:381-384 (1998).
Fu et al., Proc. Natl. Acad. Sci. USA, 92:10162-10166 (1995).
Fu et al., Nucl. Acids Res. 25(3):677-679 (1997).
Gabbita et al., J Neurochemistry, 73(4):1660-1666 (1999).
Gardiner-Gordon et al., J. Mol. Biol. 196:261-281 (1987).
Germer et al, Genome Research, 10:258-266 (2000).
Glantz et al., J. Biol. Chem., 2681171:12796-12804 (1993).
Goldmacher et al, Bioconj. Chem., 3:104-107 (1992).
Goldman and Youvan, Biotechnology 10:1557-1561 (1992).
Graber et al., Genetic Analysis: Biomolecular Engineering, 14:215-219 (1999).
Griffin et al., Nature Biotechnology, 15:1368-1372 (1997).
Grunau et al., Nucl. Acid Res., 29:C65 (2001).
Guatelli et al, Proc. Natl. Acad. Sci. USA, 87:1874-1878 (1990).
Hausken et al., J. Biol. Chem., 271(46):29016-29022 (1996).
Hazum et al., in Pept., Proc. Eur. Pept. Symp., 16th, Brunfeldt, K., (Ed.), pp. 105-110 (1981).
Herman et al., Proc. Natl. Acad. Sci. 93:9821-26 (1996).
Hey, J., Trends in Genetics 14(8): 303-305 (1998) (with reply by L. Cavalli-Wom).
Higgins et al., BioTechniques, 23(4):710-714 (1997).
Higgins et al., Methods in Enzymology, 68:50-71(1979).
Higley et al., Mutation Research, DNA Repair, 294;109-116 (1993).
Hinton et al., Laboratory Automation & Information Management, vol. 21 No. 2103, pp. 223-227, Dec. 1, 1993.
Hoogendoorn, et al., Hum Genet. (2000) 107:488-493.
Huang et al., Journal of Biological Chemistry, 272(12):8057-8064 (1997).
Huang et al., Proc. Natl. Acad. Sci. USA, 94:11104-11189 (1997).
Hubbard et al., Trends Biochem. Sci., 18:172-177 (1993).
Ikemoto, S., Nippon Hoigaku Zasshi 49(6): 419-431 (1995).
Jahnsen et al, J.Biol. Chem., 261(26):12352-12361 (1986).
Jiang-Baucom et al., Analytical Chemistry, 61:4894-4898 (1997}.
Ju, L.-Y., et al., Electrophoresis 12(4):270-273 (1991).
Jurinke et al., Genetic Analysis: Biomolecular Engineering. 13:67-71(1996).
Jurinke et al, Genetic Analysis: Biomolecular Engineering, 14:97-102 (1998).
Jurinke et al., Anal. Biochem., 237:174-181 (1996).
Jurinke et al., Anal. Chem., 69:904-910 (1997).
Kario et al., Thromb. Haemost., 73:617-22 (1995).
Klauck et al., Science, 271:1589-1592 (1998).
Koster et al., Nucl. Acids Res., Symposium Series No. 24 (1991) 318-321.
Krebs et al., Nucleic Acids Res., 31(7):E37.1-E37.8 (2003).
Kwoh et al., Proc. Natl. Acad. Sci. USA,:86:1173-1177 (1989).
Laken et al., Nature Biotechnology, 16:1352-1356 (1998).
Laken et al., Nature Genetics, 17:79-83 (1995).
Lam et al., Diabetologia, 41:760-766 (1998).
Landegren et al., Genome Res., 8:769-776 (1998).
Lasko et al, Mutation Research, 236:277-287 (1990).
Le hellard, et al., Nucleic Acids Research, (2002) 1-10, 30(15).
Lee et al., Proc. Natl. Acad. Sci. USA, 80:3608-3612 (1983).
Lehman, I.R.,Science, 186:790-797(1974).
Li et al., Anal. Chem., 68(13):2090-2096 (1996).
Li et al., Cell, 69:915-926 (1992).
Li et al., Nucl. Acids Res., 22(4):632-636 (1994).
Li, J., Abstract—Eleventh IEEE Symposium on Computer-Based Medical Systems, pp. 252-255 (1998).
Lindahi et al, Annu. Rev. Biochem., 61:251-281 (1992).
Little et al., International Journal of Mass Spectrometry and ion Processes,169-170:323-330 (1997).
Little et al., Anal. Chem., 69:4540-4546 (1997).
Little et al., Eur. J. Clin. Chem. Clin. Biochem.,35(7),:545-548 (1997).
Little et al., J. Mol. Med., 75:745-750 (1997).
Little et al., Nature Medicine, 3:1413-1416 (1997).
Lizardi et al., BioTechnology, 6:1197-1202 (1988).
McKinzie et al., Mutation Research, 517(1-2):209-220 (2002).
Miki and Eddy., J. Biol. Chem., 273(51):34384-34390, (1998).
Miki et al., J. Biol. Chem.274(41):29057-29062 (1999).
Minshull and Stemmer Curr. Opin. Chem. Biol., 3(3):284-290 (1999).
Mochly-Rosen, D.,Science, 268:247-251 (1995).
Moskovitz et al., Proc. Natl. Acad. Sci. USA, 95:14071-14075 (1998).
Muller et al., Human Molecular Genetics, 9(5):757-763, 2000.
Nagamura et al, Plant Molecular Biology 35: 79-87 (1997).
Nelson et al., Journal of Magnetic Resonance 84:95-109 (1989).

Nikodem, V. and J.R. Fresco, "Protein Fingerprinting by SDS-Gel Electrophoresisafter Partial Fragmentation with CNBr", Anal. Biochem., 97(2): 382-386 (1979).
Nilges et al., J. Mol. Biol., 269:408-422 (1997).
Nucleases 2nd ed., Linn, S.M. et al., (Eds.), Cold Spring Harbor Laboratory Press (1993).
Okano et al., Cell, 99: 247-257 (1999).
Olek et al., Nucl. Acid Res., 24:5064-5066 (1996).
Paterson, A.H., Genome Research 5(4): 321-333 (1995).
Pena et al., J. Mol. Med. 73: 555-564 (1995).
Pevzner, J. Biomol. Struct. Dyn., 7:63-73 (1989).
Pevzner, PNAS USA, 98(17):9748-9753 (2001).
Podhajska et al., Gene, 40:175-182 (1985).
Polettini et al., Journal of Chromatography B 713; 265-279 (1998).
Tammen et al.,, J. Cromatogr. A. 852:285-295, (1999).
van den Boom et al., Int. J. Mass Spectrom., 238(2):173-188 (2004).
van den Boom et al., J. Biochem. Biophys. Methods, 35:69-79 (1997).
Vaughan et al., Genetic Analysis: Biomolecular Engineering, 14:169-175 (1999).
Wada, J. Mass Spectrometry, 33:187-192 (1998).
Waga et al., J. Biol. Chem., 269(14)10923-10934 (1994).
Wang et al, J. Mol. Spectrosc., 194(20):256-268 (1999).
Weiler et al., Nucleic Acids Res., 25:2792-2799 (1997).
Wilson et al., Annu. Rev. Genet., 25:585-627(1991).
Yasuda et al. , Japanese Journal of Legal Medicine 51: 407-416 (1997).
Yates, J. Mass Spec., 33:1-19 (1998).
Yen et al, Makromol. Chem., 190:69-82 (1989).
Zhou, et al., Nucl. Acids Res., (2001) , 29(19 e93):1-11.
U.S. Appl. No. 11/997,402, filed Jan. 30, 2008, van den Boom.
Aoki E. et al., "Methylation status of the pl5INK4B gene in hematopoietic progenitors and peripheral blood cells in myelodysplastic syndromes", Leukemia 14(4):586-593 (2000).
Asimakopoulos FA et al., "ABL 1 methylation is a distinct molecular event associated with clonal evolution of chronic myeloid leukemia" Blood 94(7):2452-2460 (1999).
Bair and Tibshirani, PloS Biol 2:E108 (2004).
Bullinger L. et al. N Engl J Med 350:1605-16 (2004).
Chan et al., Oncogene 22:924-934 (2003).
Chen et al., Analytical Biochemistry, 1996, vol. 239, p. 61-69.
Colella et al. Biotechniques. Jul. 2003;35(1):146-50.
Costello et al., Nature Gent, 24:132-138 (2000).
Dohner et al. J Clin Oncol 20:3254-61 (2002).
Dupont JM, Tost J, Jammes H, and Gut IG. Anal Biochem, Oct. 2004; 333(1): 119-27.
Fajkusova L. et al., "Detailed Mapping of Methylcytosine Positions at the CpG Island Surrounding the Pa Promoter at the bcr-abl Locus in CML Patients and in Two Cell Lines, K562 and BV173" Blood Cells Mol. Dis. 26(3):193-204 (2000).
Feinberg, AP Nat Genet 27:9-10 (2001).
Frigola et al. Nat Genet. May 2006;38(5):540-9.
Frohling et al. Blood 100:4372-80 (2002).
Gebhard et al. Cancer Res. Jun. 15, 2006;66(12):6118-28.
Genebank Accession No. NM_153620, Jun. 15, 2008.
Genebank Accession No. AB025106, Jan. 7, 2000.
Genebank Accession No. AB040880, Feb. 22, 2001.
Genebank Accession No. BC013998, Sep. 11, 2007.
Genebank Accession No. NM_001031680, Jun. 15, 2008.
Genebank Accession No. NM_001394, Jun. 1, 2008.
Genebank Accession No. NM_001614, Feb. 10, 2008.
Genebank Accession No. NM_003998, May 25, 2008.
Genebank Accession No. NM_004350, Jun. 15, 2008.
Genebank Accession No. NM_004360, Jun. 15, 2008.
Genebank Accession No. NM_005522, Jun. 15, 2008.
Genebank Accession No. NM_005766, Feb. 11, 2008.
Genebank Accession No. NM_033317, Apr. 29, 2008.
Issa JP, Nat Rev Cancer 4:988-93 (2004).
Kaneko et al., Gut 52:641-646 (2003).
Laird, P.W. Nature Reviews Cancer 3, 253-266 (2003).
Litz C. E. et al., "Methylation status of the major breakpoint cluster region in Philadelphia chromosome negative leukemias" Leukemia 6(1):35-41 (1992).
Nosaka, K. et al., "Increasing methylation of the CDKN2A gene is associated with the progression of adult T-cell leukemia", Cancer Res. 60(4):1043-1048 (2000).
Puskas et al. Genome Research, 1995, vol. 5, p. 309-311.
Schuette et al. Journal of Parmaceutical and Biomedical Analysis, 1995, vol. 13, p. 1195-1203.
Strathdee, et al., Am. J. Pathol. 158:1121-1127 (2001).
Tooke N and Pettersson M. IVDT. Nov. 2004; 41.
Toyota, M. et al., Blood 97:2823-9 (2001).
Uhlmann, K. et al. Electrophoresis 23:4072-4079 (2002).
Valk PJ et al. N Engl J Med 350:1617-28 (2004).
Akiyama, Y. et al., "Cell-Type-Specific Repression of the Maspin Gene is Disrupted Frequently by Demethylation at the . . . " Amer. J. of Pathology, 2003, 1911-1919,163, Japan.
Badger et al., "New features and enhancements in the X-PLOR computer program", Proteins: Structure, Function, and Genetics, 35(1):25-33, (1999).
Baylin and Bestor, "Altered methylation pattersn in cancer cell genomes: cause or consequence?" Cancer Cell. May 2002;1(4):299-305.
Blazewicz et al., "On some properties on DNA graphics," Discrete Applied Mathematics, vol. 98, 1999, pp. 1-19.
Blazewicz et al., "On the recognition of de Bruijn graphs and their induced subgraphs," Discrete Applied Mathematics, vol. 245, 81-92 Feb. 28, 2002.
Buck et al., "Design Strategies and Performance of Custom DNA Sequencing Primers" BioTechniques. Sep. 1999. 27:528-536.
Caskey, C. T. et al., Science 256(5058): 784-789 (1992).
Chen et al., "Detectionin fecal DNA or colon cancer specific methylation of the nonexpressed vimentin gene," J Natl Cancer Inst., Aug. 3, 2005;97(15):1124-1132.
Chung, M.H. et al., Mutat. Res., 254(1): 1-12, (1991).
Costello, J. et al., "Methylation matters: a new spin on maspin" Nature Genetics, 2002, 123-124,31 USA.
Dahl, et al., "DNA methylation analysis techniques," Biogerontology, 2003, vol. 4 pp. 233-250; especially pp. 242-245.
De Noronha et al., (1992) PCR Methods and Applications, 2(2), p. 131-136.
Egland, K. et al., "Characterization of Overlapping XAGE-1 Transcripts Encoding a Cancer Testis Antigen Expressed in . . . " Molecular Cancer Therapeutics, 2002,441-450, USA.
Futscher, B. et al., "Aberrant Methylation of the Maspin Promoter is an Early Event in Human Breast Cancer" Neoplasia, 2004,380-389, 6, USA.
Futscher, B., et al., "Role for DNA methylation in the control of cell type-specific maspin expression", Nature Genetics, 2002, 175-179, 31, USA.
Genbank Accession AC005730, Oct. 22, 1998.
Genbank Accession AF021833, Sep. 29, 1999.
Genbank Accession AF096289, Mar. 22, 1999.
Genbank Accession AJ242973, Oct. 26, 1999.
Genbank Accession AW195104, Nov. 29, 1999.
Genbank Accession AW874187, May 22, 2000.
Genbank Accession NM007202, Jan. 17, 2003.
Genbank Accession No. AF037439, Chatterjee et al. Dec. 1997.
Genbank Accession X86173, Mar. 8, 1996.
Germer, Saren, et al, High-throughput SNP Allele-Frequency Determination in Pooled DNA Samples by Kinetic PCR, Methods, Genome Research, (2000). 258-266, 10, Cold Spring Harbor Laboratory Press.
Gunderson et al., "Mutation detection by ligation to complete n-mer DNA Arrays," Genome Res. Nov. 1998;8(11):1142-1153.
Heighway, J. et al., "Expression profiling of primary non-small cell lung cancer for target identification", Oncogene, 2002, 7749-7763,21, UK.
Hurtubise, A. et al., "Evaluation of antineoplastic action of 5-aza-2rdeoxycytidine, (Dacogen) and docetaxel (Taxotere) on . . . " Anti-Cancer Drugs, 2004. 161-1 67, 15, Canada.
Instrumentation; "Genesis 200/8" (200 cm with including an 8-tip arm) liquid handling systems; Tecan AG of Switzerland ("Tecan"), TECAN Products for Diagnostics and Life Science, located at http://www.tecan.ch/index.htm, Sep. 8, 1999.

Instrumentation; "Model CRS A 255" robot"Digital Servo Gripper""Plate Cube" system."lid parking station""shaker"Robocon Labor-und Industrieroboter Ges.m.b.H of Austria ("Robocon") Sep. 8, 1999.

Instrumentation; "Multimek 96" automated pipettor; Beckman Coulter, Inc. located at http://www.coultercom, Sep. 8, 1999.

Instrumentation; "Nano-Plotter" from GeSiM, Germany, located at http:/www.gesim.de/np-intro.htm, Sep. 8, 1999.

Instrumentation; Bar code systems, including one and two dimensional bar codes, readable and readable/writable codes and systems; Datalogic S.p.A. of Italy ("Datalogic") located at http://www.datalogic.com, Sep. 16, 1999.

Instrumentation; DYNABEADS, streptavidin-coated magnetic beads; from Dynal, Inc. Great Neck, NY and Oslo Norway, 1998-99.

Instrumentation;"MJ Microseal" plate sealer; Thermal Cycler Accessories: Sealing Options, Sealing Products, MJ Research, located at http://www.mjresearch.com/html/consumables/ealing/sealing_products.html, Aug. 26, 1999.

International Search Report for International Application No. PCT/US00/08111, Date of Mailing Nov. 13, 2000.

International Search Report for International Application No. PCT/US005/32441 Oct. 2, 2006.

Jurinke et al., "Detection of RET proto-oncogene codon 634 mutations using mass spectrometry", J. Mol. Med., 75:745-750, (1997).

Jurinke et al., (1998) Rapid Comm in Mass Spec., vol. 12, p. 50-52.

Kim, S. et al., "Maspin Expression is Transactivated by P63 and is Critical for the Modulation of Lung Cancer Progression" Cancer Research, 2004, 6900-6905, 64, Korea.

Kirk, et al., "Single Mucleotide polymorphism seeking long term association with complex disease," Nucleic Acids Res. 2002, vol. 30, No. 5, pp. 3295-3311.

Lindahl et al., Annu. Rev Biochem., 61:251-281 (1992).

Ling, X. et al., "Proteomics-Based Identification of Maspin Differential Expression in Bronchial Epithelia Immortalized . . . " Chinese J. of Cancer, 2003, 463-466, 22, China.

Liu, X. et al., "XAGE-1, A New Gene That Is Frequently Expressed in Eqing's Sarcoma" Cancer Research, 2000, 4752-4755, 60, USA.

Maass, N. et al., "Decline in the expression of the serine proteinase inhibitor maspin is associated with tumour progression . . . " J. of Pathology, 2001, 321-326,195, Germany.

Maass, N., et al., "Hyipernmethylation and histone deacetylation lead to silencing of the maspin gene in human breast cancer . . . " BBRC, 2002, 125-128,297, USA.

Moon, C. et al. "Aquaporin Expression in Human Lymphocytes and Dentritic Cells" American Journal of Hematotogy, 2004 128,-133, 75, USA.

Moon, C. et al., "Involvement of aquaporins in colorectal carcinogenesis" Oncogene, 2003,6699-6703,22, USA.

Murakami, J. et al., "Effects of dernethylating agent 5aza-2'deoxycytidine and histone deacetylase inhibitor FR901228 on rnaspin . . . " Oral Oncology 2004,597-603,40, Japan.

NCBI GenBank Accession No. NM_002639, Mar. 19, 1999.

Ogasawara, S. et al., "Disruption of cell-type-specific methylation at the Maspin gene promoter is frequently involved in . . . " Oncogene, 2004, 11 17-1 124, 23, Japan.

Oshio, K. et al., "Aquaporin-1 expression in human glial tumors suggests a potential novel therapeutic target for tumor-associated . . . " Acta Neurochir, 2003,494-502, 86, USA.

Risch, Neil. et al., The Relative Power of Family-Based and Case Control Design for Linkage Disequilibrium Studies of Complex Human Diseases I. DNA Pooling. Genome Research, (1998), 1278-1288, 8, Cold Spring Harbor Laboratory Press.

Saadoun, S. et al., "Increased aquaporin 1 water channel expression in human brain tumours", British J. of Cancer, 2002, 621-623,87, UK.

Sakai et al., American Journal of Human Genetic, 1991 vol. 48, pp. 880-888.

Sato, N. et al. "Identification of maspin and S100P as novel hypomethylation targets in pancreatic cancer using global gene expression profiling", 2004, 1531-1538,23, USA.

Sequenom Advances the Industrial Genomics Revolution with the Launch of Its DNA MassArray Automated Process Line, Press Release: Sep. 28, 1998, http://www.sequenom.com/pressrelease.htm.

Sequenom and Gemini Identify Genes Linked to Cardiovascular Disease, Press Release: Nov. 28, 2000, http://www/sequenom.com/ir/ir_prs.asp.

Sequenom Announces Publication of Results From Large-Scale SNP Study With the National Cancer Institute, Press Release: Jan. 16, 2001, http://www/sequenom.com/ir/ir_prs.asp.

Sequenom Completes Design of More Than 400,000 SNP Assays; Mass EXTENDTM Assay Portfolio Covers Majority of SNPs in the Public Domain, Press Release; Oct. 10, 2000, http://www/sequenom.com/ir/ir_prs.asp.

Sequenom: Technologies and Tools, located at http://www.sequenom-san.com/tech/tools.html, dated Aug. 29, 1999.

Sheng et al., "Tagged probe interval graphs," Journal of Combinatorial Optimization. 2001 vol. 5, pp. 133-142.

Sigaloiti, L. et al., "Cancer testis antigens expression in mesothelioma:role of NA methylation . . . " British J. of Cancer, 2002, 979-982, 86, UK.

Smith, S. et al., "Maspin-the most commonly-expressed gene of the 18q21.3 serpin cluster in lung cancer . . . " Oncogene, 2003, 8677-8687,22, UK.

Stomakhin et al., "DNA sequence analysis by hybridization with oligonucleotides microchips;MALDI mass spectrometry identificaiton of 5mers contiguously stacked to microchip oligonucleotides," Nucleic Acids Res. Mar. 1, 2000;28(5):1193-1198.

Takenawa, J.et al., "Transcript Levels of Aquaporin 1 and Carbonic Anhydrase IV as Predictive indicators for Prognosis of Renel Cell . . . " Int. J. Cancer, 1998, 1-7, 79, Japan.

Uracil-DNA Glycosylase (UDG), product description. New England Biolabs. http://circuit.neb.com/neb/products/mod_enzymes/280.html, (Dec. 21, 2000).

Uracil-DNA Glycosylase, product description. Roche Molecular Biochemicals Catalog Version 3, Nov. 1999 http:/biochem.roche.com/pack-insert/1269062a.pdf, (Dec. 21, 2000).

Vacca, A. et al., "Microvessel overexprssion of aquaporin 1 parallels bone marrow angiogenesis in patients with active . . . " British J. of Haematology, 2001,415-421,113, Italy.

Wada et al., "Detection of Single-nucleotide Mutations Including Substitutions and Deletions by Matrix-assisted Laser Desorption/Ionization Time-of-flight Mass Spectrometry," Rapid Communications in Mass Spectrometry, 11:1657-1660, (1997).

Wada, K. et al., "Aberrant Expression of the Maspin Gene Associated,with Epigenetic Modification," J. Invest Dermatol, 2004, 805-811, 122, Japan.

Xiong et al., "COBRA: a sensitive and quantitative DNA methylation assay," Nucleic Acids Res. Jun. 15, 1997;25(12):2532-2534.

Yatabe, Y. et al., "Maspin expression in normal lung and non-small-cell lung cancers: cellular property . . . " Oncogene, 2004,4041-4049, 23, Japan.

Zendman, A. et al., "The XAGE Family of Cancer/Testis-Associated Genes: Alignment and Expression Profile in Normal Tissues . . . " Int. J. Cancer, 2002,361-369,99 Netherlands.

Zhu et a., "Use of DNA Methylation for cancer detection and molecular classification," J Biochem Mol Biol. Mar. 31, 2007;40(2)135-141.

Zou et al., "Maspin, a serpin with tumor-suppressing activity in human mammary epithelial cells," Science, Jan. 28, 1994;263(5146):526-529.

Supplemental European Search Report mailed on: May 7, 2010 in European Application No. 03796490.5 filed on: Nov. 26, 2003 and published as: EP 1513723 on: Jan. 11, 2006.

Office Action mailed: May 12, 2010 in U.S. Appl. No. 10/933,611 filed on Sep. 2, 2004 Published as: US-2005-0089904A1 on Apr. 28, 2005.

* cited by examiner

FRAGMENTATION-BASED METHODS AND SYSTEMS FOR SEQUENCE VARIATION DETECTION AND DISCOVERY

RELATED APPLICATIONS

Benefit of priority under §119(e) is claimed to U.S. Provisional Application Ser. No. 60/429,895, filed Nov. 27, 2002, entitled "Fragmentation-based Methods and Systems for Sequence Variation Detection and Discovery", the subject matter of which is incorporated herein in its entirety.

The subject matter of each of the following applications also is incorporated herein by reference in its entirety: U.S. Provisional Application Ser. No. 60/466,006, filed Apr. 25, 2003, entitled "Fragmentation-based Methods and Systems for de novo Sequencing", and International PCT Application entitled "Fragmentation-based Methods and Systems for Sequence Variation Detection and Discovery", filed Nov. 26, 2003.

BACKGROUND

The genetic information of all living organisms (e.g., animals, plants and microorganisms) is encoded in deoxyribonucleic acid (DNA). In humans, the complete genome contains of about 100,000 genes located on 24 chromosomes (The Human Genome, T. Strachan, BIOS Scientific Publishers, 1992). Each gene codes for a specific protein, which after its expression via transcription and translation, fulfills a specific biochemical function within a living cell.

A change or variation in the genetic code can result in a change in the sequence or level of expression of mRNA and potentially in the protein encoded by the mRNA. These changes, known as polymorphisms or mutations, can have significant adverse effects on the biological activity of the mRNA or protein resulting in disease. Mutations include nucleotide deletions, insertions, substitutions or other alterations (i.e., point mutations).

Many diseases caused by genetic polymorphisms are known and include hemophilia, thalassemia, Duchenne Muscular Dystrophy (DMD), Huntington's Disease (HD), Alzheimer's Disease and Cystic Fibrosis (CF) (Human Genome Mutations, D. N. Cooper and M. Krawczak, BIOS Publishers, 1993). Genetic diseases such as these can result from a single addition, substitution, or deletion of a single nucleotide in the deoxynucleic acid (DNA) forming the particular gene. In addition to mutated genes, which result in genetic disease, certain birth defects are the result of chromosomal abnormalities such as Trisomy 21 (Down's Syndrome), Trisomy 13 (Patau Syndrome), Trisomy 18 (Edward's Syndrome), Monosomy X (Turner's Syndrome) and other sex chromosome aneuploidies such as Klinefelter's Syndrome (XXY). Further, there is growing evidence that certain DNA sequences can predispose an individual to any of a number of diseases such as diabetes, arteriosclerosis, obesity, various autoimmune diseases and cancer (e.g., colorectal, breast, ovarian, lung).

A change in a single nucleotide between genomes of more than one individual of the same species (e.g., human beings), that accounts for heritable variation among the individuals, is referred to as a "single nucleotide polymorphism" or "SNP." Not all SNPs result in disease. The effect of an SNP, dependent on its position and frequency of occurrence, can range from harmless to fatal. Certain polymorphisms are thought to predispose some individuals to disease or are related to morbidity levels of certain diseases. Atherosclerosis, obesity, diabetes, autoimmune disorders, and cancer are a few of such diseases thought to have a correlation with polymorphisms. In addition to a correlation with disease, polymorphisms are also thought to play a role in a patient's response to therapeutic agents given to treat disease. For example, polymorphisms are believed to play a role in a patient's ability to respond to drugs, radiation therapy, and other forms of treatment.

Identifying polymorphisms can lead to better understanding of particular diseases and potentially more effective therapies for such diseases. Indeed, personalized therapy regiments based on a patient's identified polymorphisms can result in life saving medical interventions. Novel drugs or compounds can be discovered that interact with products of specific polymorphisms, once the polymorphism is identified and isolated. The identification of infectious organisms including viruses, bacteria, prions, and fungi, can also be achieved based on polymorphisms, and an appropriate therapeutic response can be administered to an infected host.

Since the sequence of about 16 nucleotides is specific on statistical grounds even for the size of the human genome, relatively short nucleic acid sequences can be used to detect normal and defective genes in higher organisms and to detect infectious microorganisms (e.g., bacteria, fungi, protists and yeast) and viruses. DNA sequences can even serve as a fingerprint for detection of different individuals within the same species (see, Thompson, J. S. and M. W. Thompson, eds., *Genetics in Medicine*, W.B. Saunders Co., Philadelphia, Pa. (1991)).

Several methods for detecting DNA are used. For example, nucleic acid sequences are identified by comparing the mobility of an amplified nucleic acid molecule with a known standard by gel electrophoresis, or by hybridization with a probe, which is complementary to the sequence to be identified. Identification, however, can only be accomplished if the nucleic acid molecule is labeled with a sensitive reporter function (e.g., radioactive ($^{32}$P, $^{35}$S), fluorescent or chemiluminescent). Radioactive labels can be hazardous and the signals they produce decay over time. Non-isotopic labels (e.g., fluorescent) suffer from a lack of sensitivity and fading of the signal when high intensity lasers are being used. Additionally, performing labeling, electrophoresis and subsequent detection are laborious, time-consuming and error-prone procedures. Electrophoresis is particularly error-prone, since the size or the molecular weight of the nucleic acid cannot be directly correlated to the mobility in the gel matrix. It is known that sequence specific effects, secondary structure and interactions with the gel matrix cause artefacts. Moreover, the molecular weight information obtained by gel electrophoresis is a result of indirect measurement of a related parameter, such as mobility in the gel matrix.

Applications of mass spectrometry in the biosciences have been reported (see *Meth. Enzymol.*, Vol. 193, *Mass Spectrometry* (McCloskey, ed.; Academic Press, NY 1990); McLaffery et al., *Acc. Chem. Res.* 27:297-386 (1994); Chait and Kent, *Science* 257:1885-1894 (1992); Siuzdak, *Proc. Natl. Acad. Sci., USA* 91:11290-11297 (1994)), including methods for mass spectrometric analysis of biopolymers (see Hillenkamp et al. (1991) *Anal. Chem.* 63:1193A-1202A) and for producing and analyzing biopolymer ladders (see, International Publ. WO 96/36732; U.S. Pat. No. 5,792,664).

MALDI-MS requires incorporation of the macromolecule to be analyzed in a matrix, and has been performed on polypeptides and on nucleic acids mixed in a solid (i.e., crystalline) matrix. In these methods, a laser is used to strike the biopolymer/matrix mixture, which is crystallized on a probe tip, thereby effecting desorption and ionization of the biopolymer. In addition, MALDI-MS has been performed on polypeptides using the water of hydration (i.e., ice) or glycerol as a matrix. When the water of hydration was used as a matrix, it was necessary to first lyophilize or air dry the protein prior to performing MALDI-MS (Berkenkamp et al. (1996) *Proc. Natl. Acad. Sci. USA* 93:7003-7007). The upper mass limit for this method was reported to be 30 kDa with limited sensitivity (i.e., at least 10 pmol of protein was required).

MALDI-TOF mass spectrometry has been employed in conjunction with conventional Sanger sequencing or similar primer-extension based methods to obtain sequence information, including the detection of SNPs (see, e.g., U.S. Pat. Nos. 5,547,835; 6,194,144; 6,225,450; 5,691,141 and 6,238,871; H. Köster et al., *Nature Biotechnol.*, 14:1123-1128, 1996; WO 96/29431; WO 98/20166; WO 98/12355; U.S. Pat. No. 5,869,242; WO 97/33000; WO 98/54571; A. Braun et al., *Genomics*, 46:18, 1997; D. P. Little et al., *Nat. Med.*, 3:1413, 1997; L. Haff et al., *Genome Res.*, 7:378, 1997; P. Ross et al., *Nat. Biotechnol.*, 16:1347, 1998; K. Tang et al., *Proc. Natl. Acad. Sci. USA*, 96:10016, 1999). Since each of the four naturally occurring nucleotide bases dC, dT, dA and dG, also referred to herein as C, T, A and G, in DNA has a different molecular weight: $M_C$=289.2; $M_T$=304.2; $M_A$=313.2; $M_G$=329.2; where $M_C$, $M_T$, $M_A$, $M_G$ are average molecular weights (under the natural isotopic distribution) in daltons of the nucleotide bases deoxycytidine, thymidine, deoxyadenosine, and deoxyguanosine, respectively, it is possible to read an entire sequence in a single mass spectrum. If a single spectrum is used to analyze the products of a conventional Sanger sequencing reaction, where chain termination is achieved at every base position by the incorporation of dideoxynucleotides, a base sequence can be determined by calculation of the mass differences between adjacent peaks. For the detection of SNPs, alleles or other sequence variations (e.g., insertions, deletions), variant-specific primer extension is carried out immediately adjacent to the polymorphic SNP or sequence variation site in the target nucleic acid molecule. The mass of the extension product and the difference in mass between the extended and unextended product is indicative of the type of allele, SNP or other sequence variation.

U.S. Pat. No. 5,622,824, describes methods for DNA sequencing based on mass spectrometric detection. To achieve this, the DNA is by means of protection, specificity of enzymatic activity, or immobilization, unilaterally degraded in a stepwise manner via exonuclease digestion and the nucleotides or derivatives detected by mass spectrometry. Prior to the enzymatic degradation, sets of ordered deletions that span a cloned DNA sequence can be created. In this manner, mass-modified nucleotides can be incorporated using a combination of exonuclease and DNA/RNA polymerase. This permits either multiplex mass spectrometric detection, or modulation of the activity of the exonuclease so as to synchronize the degradative process.

U.S. Pat. Nos. 5,605,798 and 5,547,835 provide methods for detecting a particular nucleic acid sequence in a biological sample. Depending on the sequence to be detected, the processes can be used, for example, in methods of diagnosis.

Technologies have been developed to apply MALDI-TOF mass spectrometry to the analysis of genetic variations such as microsatellites, insertion and/or deletion mutations and single nucleotide polymorphisms (SNPs) on an industrial scale. These technologies can be applied to large numbers of either individual samples, or pooled samples to study allelic frequencies or the frequency of SNPs in populations of individuals, or in heterogeneous tumor samples. The analyses can be performed on chip-based formats in which the target nucleic acids or primers are linked to a solid support, such as a silicon or silicon-coated substrate, preferably in the form of an array (see, e.g., K. Tang et al., *Proc. Natl. Acad. Sci. USA*, 96:10016, 1999). Generally, when analyses are performed using mass spectrometry, particularly MALDI, small nano-liter volumes of sample are loaded onto a substrate such that the resulting spot is about, or smaller than, the size of the laser spot. It has been found that when this is achieved, the results from the mass spectrometric analysis are quantitative. The area under the signals in the resulting mass spectra are proportional to concentration (when normalized and corrected for background). Methods for preparing and using such chips are described in U.S. Pat. No. 6,024,925, co-pending U.S. application Ser. Nos. 08/786,988, 09/364,774, 09/371,150 and 09/297,575; see, also, U.S. application Ser. No. PCT/US97/20195, which published as WO 98/20020. Chips and kits for performing these analyses are commercially available from SEQUENOM, INC. under the trademark MassARRAY™. MassARRAY™ relies on mass spectral analysis combined with the miniaturized array and MALDI-TOF (Matrix-Assisted Laser Desorption Ionization-Time of Flight) mass spectrometry to deliver results rapidly. It accurately distinguishes single base changes in the size of DNA fragments associated with genetic variants without tags.

Although the use of MALDI for obtaining nucleic acid sequence information, especially from DNA fragments as described above, offers the advantages of high throughput due to high-speed signal acquisition and automated analysis off solid surfaces, there are limitations in its application. When the SNP or mutation or other sequence variation is unknown, the variant mass spectrum or other indicator of mass, such as mobility in the case of gel electrophoresis, must be simulated for every possible sequence change of a reference sequence that does not contain the sequence variation. Each simulated variant spectrum corresponding to a particular sequence variation or set of sequence variations must then be matched against the actual variant mass spectrum to determine the most likely sequence change or changes that resulted in the variant spectrum. Such a purely simulation-based approach is time consuming. For example, given a reference sequence of 1000 bases, there exist approximately 9000 potential single base sequence variations. For every such potential sequence variation, one would have to simulate the expected spectra and to match them against the experimentally measured spectra. The problem is further compounded when multiple base variations or multiple sequence variations rather than only single base or sequence variations are present.

Therefore, there is a need to improve the accuracy of SNP, mutation and other sequence variation detection and discovery. Thus, among the objects herein, is an object to improve the accuracy of SNP, mutation and other sequence variation detection and discovery. Also among the objects herein, is an increase in the speed of SNP, mutation and sequence variation detection and discovery.

SUMMARY

Provided herein are methods and systems for highly accurate SNP, mutation and other sequence variation detection and discovery. The methods and systems herein permit rapid and accurate SNP, mutation and sequence variation detection and discovery.

Provided herein are methods and systems for detecting or discovering sequence variations, including nucleic acid polymorphisms and mutations, using techniques, such as mass spectrometry and gel electrophoresis, that are based upon molecular mass. The methods and systems provide a variety of information based on nucleic acid sequence variations. For example, such information includes, but is not limited to, identifying a genetic disease or chromosome abnormality; identifying a predisposition to a disease or condition including, but not limited to, obesity, atherosclerosis, or cancer; identifying an infection by an infectious agent; providing information relating to identity, heredity, or histocompatibility; identifying pathogens (e.g., bacteria, viruses and fungi); providing antibiotic or other drug-resistance profiling; determining haplotypes; analyzing microsatellite sequences and STR (short tandem repeat) loci; determining allelic variation and/or frequency; analyzing cellular methylation patterns; epidemiological analysis of genotype variations; and genetic variation in evolution.

Provided herein are methods for the detection or discovery of nucleic acid sequence variations in the diagnosis of genetic diseases, predispositions to certain diseases, cancers, and infections.

Methods for detecting known mutations, SNPs, or other kinds of sequence variations (e.g., insertions, deletions, errors in sequence determination) or for discovering new mutations SNPs or sequence variations by specific cleavage are provided. In these methods, fragments that are cleaved at a specific position in a target biomolecule sequence based on (i) the sequence specificity of the cleaving reagent (e.g., for nucleic acids, the base specificity such as single bases A, G, C, T or U, or the recognition of modified single bases or nucleotides, or the recognition of short, between about two to about twenty base, non-degenerate as well as degenerate oligonucleotide sequences); or (ii) the structure of the target biomolecule; or (iii) physical processes, such as ionization by collision-induced dissociation during mass spectrometry; or (iv) a combination thereof, are generated from the target biomolecule. The analysis of fragments rather than the full length biomolecule shifts the mass of the ions to be determined into a lower mass range, which is generally more amenable to mass spectometric detection. For example, the shift to smaller masses increases mass resolution, mass accuracy and, in particular, the sensitivity for detection. The actual molecular weights of the fragments of the target biomolecule as determined by mass spectrometry provide sequence information (e.g., the presence and/or identity of a mutation). The methods provided herein can be used to detect a plurality of sequence variations in a target biomolecule.

The fragment molecular weight pattern, i.e., mass signals of fragments that are generated from the target biomolecule is compared to the actual or simulated pattern of fragments generated under the same cleavage conditions for a reference sequence. The reference sequence usually corresponds to the target sequence, with the exception that the sequence variations (mutations, polymorphisms) to be identified in the target sequence, are not present in the reference sequence. For example, if the biomolecule is a nucleic acid, the reference nucleic acid sequence can be derived from a wild-type allele, whereas the target nucleic acid sequence can be derived from a mutant allele. As another example, the reference nucleic acid sequence can be a sequence from the human genome, whereas the target nucleic acid sequence can be a sequence from an infectious organism, such as a pathogen. The differences in mass signals between the target sequence and the reference sequence are then analyzed to determine the sequence variations that are most likely to be present in the target biomolecule sequence. The difference in mass signals between the target sequence and the reference sequence can be absolute (i.e., a mass signal that is present in the fragmentation spectrum of one sequence but not the other), or it can be relative, such as, but not limited to, differences in peak intensities (height, area, signal-to-noise or combinations thereof) of the signals.

The methods provided herein can be used to screen nucleic acid sequences of up to and greater than 2000 bases for the presence of sequence variations relative to a reference sequence. Further, the sequence variations are detected with greater accuracy due to the reduced occurrence of base-calling errors, which proves especially useful for the detection of "true" SNPs, such as SNPs in the coding region of a gene that results in an amino acid change, which usually have allele frequencies of less than 5% (see, e.g., L. Kruglyak et al., *Nat. Genet.*, 27:234, 2001).

In the methods provided herein, the differences in mass signals between the fragments that are obtained by specific cleavage of the target nucleic acid sequence and those obtained by actual or simulated specific cleavage of the reference nucleic acid sequence under the same conditions are identified ("additional" or "missing" mass signals in the target nucleic acid fragment spectrum), and the masses of the fragments corresponding to these differences are determined. The set of differences can include, in addition to "missing" or "additional" signals in the target fragmentation pattern, signals of differing intensities or signal to noise ratios between the target and reference sequences. Once the masses of the fragments corresponding to differences between the target sequence and the reference sequence are determined ("different" fragments), one or more nucleic acid base compositions (compomers) are identified whose masses differ from the actual measured mass of each different fragment by a value that is less than or equal to a sufficiently small mass difference. These compomers are called witness compomers. The value of this sufficiently small mass difference is determined by parameters such as, but not limited to, the mass of the different fragment, the peak separation between fragments whose masses differ by a single nucleotide in type or length, and the absolute resolution of the mass spectrometer. Cleavage reactions specific for one or more of the four nucleic acid bases (A, G, C, T or U for RNA, or modifications thereof) can be used to generate data sets comprising the possible witness compomers for each specifically cleaved fragment that nears or equal the measured mass of each different fragment by a value that is less than or equal to the sufficiently small mass difference.

The generated witness compomers for each different fragment can then be used to determine the presence of SNPs or other sequence variations (e.g., insertions, deletions, substitutions) in the target nucleic acid sequence.

The possible witness compomers corresponding to the different fragments can be manually analyzed to obtain sequence variations corresponding to the compomers. In another aspect, mathematical algorithms are provided to reconstruct the target sequence variations from possible witness compomers of the different fragments. In a first step, all possible compomers whose masses differ by a value that is less than or equal to a sufficiently small mass difference from the actual mass of each different fragment generated in either the target nucleic acid or the reference nucleic acid cleavage reaction relative to the other under the same cleavage conditions, are identified. These compomers are the 'compomer witnesses'. The algorithm then determines all sequence variations that would lead to the identified compomer witnesses. The algorithm constructs those sequence variations of the target sequence relative to a reference sequence that contain at most k mutations, polymorphisms, or other sequence variations, including, but not limited to, sequence variations between organisms, insertions, deletions and substitutions.

The value of k, the sequence variation order, is dependent on a number of parameters including, but not limited to, the expected type and number of sequence variations between a reference sequence and the target sequence, e.g., whether the sequence variation is a single base or multiple bases, or whether sequence variations are present at one location or at more than one location on the target sequence relative to the reference sequence. For example, for the detection of SNPs, the value of k is usually, although not necessarily, 1 or 2. For the detection of mutations and in resequencing, the value of k is usually, although not necessarily, 3 or higher. The sequences representing possible sequence variations contained in the target sequence relative to the reference sequence are called sequence variation candidates. The possible sequence variations that are detected in the target sequence are usually the sum of all sequence variations for which specific cleavage generates a witness compomer corresponding to each sequence variation.

A second algorithm is used to generate a simulated spectrum for each computed output sequence variation candidate. The simulated spectrum for each sequence variation candidate is scored, using a third (scoring) algorithm, against the actual spectrum for the target nucleic acid sequence. The value of the scores (the higher the score, the better the match, with the highest score usually being the sequence variation that is most likely to be present) can then be used to determine the sequence variation candidate that corresponds to the actual target nucleic acid sequence. The output of sequence variation candidates will include all sequence variations of the target sequence relative to the reference sequence that generate a different fragment in a specific cleavage reaction. For sequence variations in the target sequence that do not interact with each other, i.e., the separation (distance) between sequence variations along the target sequence is sufficient for each sequence variation to generate a distinct different fragment (of the target sequence relative to the reference sequence) in a specific cleavage reaction, the differences in the fragmentation pattern of the target sequence relative to the reference sequence represents the sum of all sequence variations in the target sequence relative to the reference sequence.

When a plurality of target sequences are analyzed against the same reference sequence, the algorithm can combine the scores of those target sequences that correspond to the same sequence variation candidate. Thus, an overall score for the sequence variation candidate representing the actual sequence variation can be determined. This embodiment is particularly useful, for example, in SNP discovery.

The sequence variation candidate output can be further used in an iterative process to detect additional sequence variations in the target sequence. For example, in the iterative process of detecting more than one sequence variation in a target sequence, the sequence variation with the highest score is accepted as an actual sequence variation, and the signal or peak corresponding to this sequence variation is added to the reference fragment spectrum to generate an updated reference fragment spectrum. All remaining sequence variation candidates are then scored against this updated reference fragment spectrum to output the sequence variation candidate with the next highest score. This second sequence variation candidate can also represent a second actual sequence variation in the target sequence. Therefore, the peak corresponding to the second sequence variation can be added to the reference fragment spectrum to generate a second updated reference spectrum against which a third sequence variation can be detected according to its score. This process of iteration can be repeated until no more sequence variation candidates representing actual sequence variations in the target sequence are identified.

In one embodiment, provided herein is a method for determining allelic frequency in a sample by cleaving a mixture of target nucleic acid molecules in the sample containing a mixture of wild-type and mutant alleles into fragments using one or more specific cleavage reagents; cleaving or simulating cleavage of a nucleic acid molecule containing a wild-type allele into fragments using the same one or more cleavage reagents; determining the masses of the fragments; identifying differences in fragments between the target nucleic acid molecule and the wild-type nucleic acid molecule that are representative of sequence variations in the mixture of target nucleic acid molecules relative to the wild-type nucleic acid molecule; determining the different fragments that are compomer witnesses; determining the set of bounded compomers of sequence variation order k corresponding to each compomer witness; determining the allelic variants that are candidate alleles for each bounded compomer; scoring the candidate alleles; and determining the allelic frequency of the mutant alleles in the sample.

In other embodiments, the methods provided herein can be used for detecting sequence variations in a target nucleic acid in a mixture of nucleic acids in a biological sample. Biological samples include but are not limited to DNA from a pool of individuals, or a homogeneous tumor sample derived from a single tissue or cell type, or a heterogeneous tumor sample containing more than one tissue type or cell type, or a cell line derived from a primary tumor. Also contemplated are methods, such as haplotyping methods, in which two mutations in the same gene are detected.

In other embodiments, a plurality of target nucleic acids can be multiplexed in a single reaction measurement by fragmenting each target nucleic acid and one or more reference nucleic acids in the same cleavage reactions using one or more cleavage reagent. These methods are particularly useful when differences in fragmentation patterns between one or more target nucleic acids relative to one or more reference nucleic acids using one or more specific cleavage reagents are simultaneously analyzed.

In one embodiment, the fragments generated according to the methods provided herein are analyzed for the presence of sequence variations relative to a reference sequence, and the analyzed fragment sequences are ordered to provide the sequence of the larger target nucleic acid. The fragments can be generated by partial or total cleavage, using a single specific cleavage reaction or complementary specific cleavage reactions such that alternative fragments of the same target biomolecule sequence are obtained. The cleavage means can be enzymatic, chemical, physical or a combination thereof, as long as the site of cleavage can be identified.

The target nucleic acids can be selected from among single stranded DNA, double stranded DNA, cDNA, single stranded RNA, double stranded RNA, DNA/RNA hybrid, PNA (peptide nucleic acid) and a DNA/RNA mosaic nucleic acid. The target nucleic acids can be directly isolated from a biological sample, or can be derived by amplification or cloning of nucleic acid sequences from a biological sample. The amplification can be achieved by polymerase chain reaction (PCR), reverse transcription followed by the polymerase chain reaction (RT-PCR), strand displacement amplification (SDA), rolling circle amplification and transcription based processes.

The target biomolecules, such as nucleic acids, proteins and peptides, can be treated prior to fragmentation so that the cleavage specificity is altered.

In one embodiment, the target nucleic acids are amplified using modified nucleoside triphosphates. The modifications either confer or alter cleavage specificity of the target nucleic acid sequence by cleavage reagents, and improve resolution of the fragmentation spectrum by increasing mass signal separation. The modified nucleoside triphosphates can be selected from among isotope enriched ($^{13}C/^{15}N$, e.g.) or isotope depleted nucleotides, mass modified deoxynucleoside triphosphates, mass modified dideoxynucleoside triphosphates, and mass modified ribonucleoside triphosphates. The mass modified triphosphates can be modified on the base, the sugar, and/or the phosphate moiety, and are introduced through an enzymatic step, chemically, or a combination of both. In one aspect, the modification can include 2' substituents other than a hydroxyl group. In another aspect, the internucleoside linkages can be modified e.g., phosphorothioate linkages or phosphorothioate linkages further reacted with an alkylating agent. In yet another aspect, the modified nucleoside triphosphate can be modified with a methyl group, e.g., 5-methyl cytosine or 5-methyl uridine.

In another embodiment, the target nucleic acids are amplified using nucleoside triphosphates that are naturally occurring, but that are not normal precursors of the target nucleic acid. For example, uridine triphosphate, which is not normally present in DNA, can be incorporated into an amplified DNA molecule by amplifying the DNA in the presence of normal DNA precursor nucleotides (e.g. dCTP, dATP, and dGTP) and dUTP. When the amplified product is treated with uracil-DNA glycolsylase (UDG), uracil residues are cleaved. Subsequent chemical or enzymatic treatment of the products from the UDG reaction results in the cleavage of the phosphate backbone and the generation of nucleobase specific fragments. Moreover, the separation of the complementary strands of the amplified product prior to glycosylase treatment allows complementary patterns of fragmentation to be generated. Thus, the use of dUTP and Uracil DNA glycosylase allows the generation of T specific fragments for the complementary strands, providing information on the T as well as the A positions within a given sequence. Similarly, a C-specific reaction on both (complementary) strands (i.e. with a C-specific glycosylase) would yield information on C as well as G positions within a given sequence if the fragmentation patterns of both amplification strands are analyzed separately. With the glycosylase method and mass spectrometry, a full series of A, C, G and T specific fragmentation patterns can be analyzed. Several methods exist where treatment of DNA with specific chemicals modifies existing bases so that they are recognized by specific DNA glycosylases. For example, treatment of DNA with alkylating agents such as methylnitrosourea generates several alkylated bases including N3-methyladenine and N3-methylguanine which are recognized and cleaved by alkyl purine DNA-glycosylase. Treatment of DNA with sodium bisulfite causes deamination of cytosine residues in DNA to form uracil residues in the DNA, which can be cleaved by uracil N-glycosylase (also known as uracil DNA-glycosylase). Chemical reagents can also convert guanine to its oxidized form, 8-hydroxyguanine, which can be cleaved by formamidopyrimidine DNA N-glycosylase (FPG protein) (Chung et al., "An endonuclease activity of *Escherichia coli* that specifically removes 8-hydroxyguanine residues from DNA," Mutation Research 254: 1-12 (1991)).

In another embodiment, bisulfite treatment of genomic DNA can be utilized to analyze positions of methylated cytosine residues within the DNA. Treating nucleic acids with bisulfite deaminates cytosine residues to uracil residues, while methylated cytosine remains unmodified. Thus, by comparing the cleavage pattern of a sequence of a target nucleic acid that is not treated with bisulfite with the cleavage pattern of the sequence of the target nucleic acid that is treated with bisulfite in the methods provided herein, the degree of methylation in a nucleic acid as well as the positions where cytosine is methylated can be deduced.

The methods provided herein are adaptable to any sequencing method or detection method that relies upon or includes fragmentation of nucleic acids. As discussed further below, fragmentation of polynucleotides is known in the art and can be achieved in many ways. For example, polynucleotides composed of DNA, RNA, analogs of DNA and RNA or combinations thereof, can be fragmented physically, chemically, or enzymatically. Fragments can vary in size, and suitable nucleic acid fragments are typically less that about 2000 nucleotides. Suitable nucleic acid fragments can fall within several ranges of sizes including but not limited to: less than about 1000 bases, between about 100 to about 500 bases, or from about 25 to about 200 bases. In some aspects, fragments of about one nucleotide may be present in the set of fragments obtained by specific cleavage.

Fragmentation of nucleic acids can also be combined with sequencing methods that rely on chain extension in the presence of chain-terminating nucleotides. These methods include, but are not limited to, sequencing methods based upon Sanger sequencing, and detection methods, such as primer oligo base extension (see, e.g., U.S. Pat. No. 6,043, 031; allowed U.S. Pat. Nos. 6,258,538; and 6,235,478), that rely on and include a step of chain extension.

One method of generating base specifically terminated fragments from a nucleic acid is effected by contacting an appropriate amount of a target nucleic acid with an appropriate amount of a specific endonuclease, thereby resulting in partial or complete digestion of the target nucleic acid. Endonucleases will typically degrade a sequence into pieces of no more than about 50-70 nucleotides, even if the reaction is run to completion. In one embodiment, the nucleic acid is a ribonucleic acid and the endonuclease is a ribonuclease (RNase) selected from among: the G-specific RNase $T_1$, the A-specific RNase $U_2$, the A/U specific RNase PhyM, U/C specific RNase A, C specific chicken liver RNase (RNase CL3) or cusavitin. In other embodiments, the nucleic acid is deoxyribonucleic acid (DNA) and the cleavage reagent is a DNAse or a glycosylase. In another embodiment, the endonuclease is a restriction enzyme that cleaves at least one site contained within the target nucleic acid. Another method for generating base specifically terminated fragments includes performing a combined amplification and base-specific termination reaction, for example, using an appropriate amount of a first DNA polymerase, which has a relatively low affinity towards the chain-terminating nucleotides resulting in an exponential amplification of the target; and a polymerase with a relatively high affinity for the chain terminating nucleotide, resulting in base-specific termination of the polymerization.

The masses of the cleaved and uncleaved target sequence fragments can be determined using methods known in the art including but not limited to mass spectroscopy and gel electrophoresis, preferably MALDI/TOF. Chips and kits for performing high-throughput mass spectrometric analyses are commercially available from SEQUENOM, INC. under the trademark MassARRAY™. The MassARRAY™ system can be used to analyze with high speed and accuracy SNPs and other mutations that are discovered and localized by base-specific fragmentation.

The methods provided herein combine the improved accuracy and clarity of identification of fragment signals produced by base-specific fragmentation rather than primer extension of target nucleic acids, with the increase in speed of analysis of these signals by using algorithms that screen the signals to select only those that are likely to represent true sequence variations within the target nucleic acid.

The methods provided herein can additionally be adapted to analyze sequence variations in samples containing mixtures of nucleic acids from multiple genomes (species), or multiple individuals, or biological samples such as tumor samples that are derived from mixtures of tissues or cells. Such "sample mixtures" usually contain the sequence variation or mutation or polymorphism containing target nucleic acid at very low frequency, with a high excess of wildtype sequence. For example, in tumors, the tumor-causing mutation is usually present in less than 5-10% of the nucleic acid present in the tumor sample, which is a heterogeneous mixture of more than one tissue type or cell type. Similarly, in a population of individuals, most polymorphisms with functional consequences that are determinative of, e.g., a disease state or predisposition to disease, occur at low allele frequencies of less than 5%. The methods provided herein can be adapted to detect low frequency mutations, sequence variations, alleles or polymorphisms that are present in the range of less than about 5-10%.

The methods provided herein can also be adapted to detect sequencing errors. For example, if the actual sequence of the reference nucleic acid(s) used in the methods provided herein is different from the reported sequence (e.g., in a published database), the methods provided herein will detect errors in the reported sequence by detecting sequence variations in the reported sequence.

The methods herein permit sequencing of oligonucleotides of any size, particularly in the range of less than about 4000 nt, more typically in the range of about 100 to about 1000 nt.

Kits containing the components for mutation (insertions, deletions, substitutions) and polymorphism detection or discovery in a target nucleic acid are also provided. The kits contain the reagents as described herein and optionally any other reagents required to perform the reactions. Such reagents and compositions are packaged in standard packaging known to those of skill in the art. Additional vials, containers, pipets, syringes and other products for sequencing can also be included. Instructions for performing the reactions can be included.

The methods provided herein can be adapted for determining sequence variations in a target protein or peptide sequence relative to a reference protein or peptide sequence. Proteins can be fragmented by specific cleavage using several techniques including chemical cleavage, enzymatic cleavage and fragmentation by ionization. The differences in fragmentation corresponding to missing or additional signals in the fragmentation spectrum of the target protein or peptide relative to the reference protein or peptide are then identified. Once the masses of the different fragments are determined, one or more amino acid compositions (compomers) are identified whose masses differ from the actual measured mass of each different fragment by a value that is less than or equal to a sufficiently small mass difference as described herein. These compomers would be the witness compomers for the target protein or peptide. Cleavage reactions specific for one or more of the twenty amino acids or of structural features characteristic of a sequence motif can be used to generate data sets comprising the possible witness compomers for each specifically cleaved fragment that nears or equals the measured mass of each different fragment by a value that is less than or equal to the sufficiently small mass difference.

The possible witness compomers for each different fragment of the target protein or peptide sequence relative to a reference sequence can then be used to determine the presence of SNPs or other sequence variations (e.g., insertions, deletions, substitutions) in the target protein or peptide sequence.

Other features and advantages will be apparent from the following detailed description and claims.

DETAILED DESCRIPTION

Figure 1:
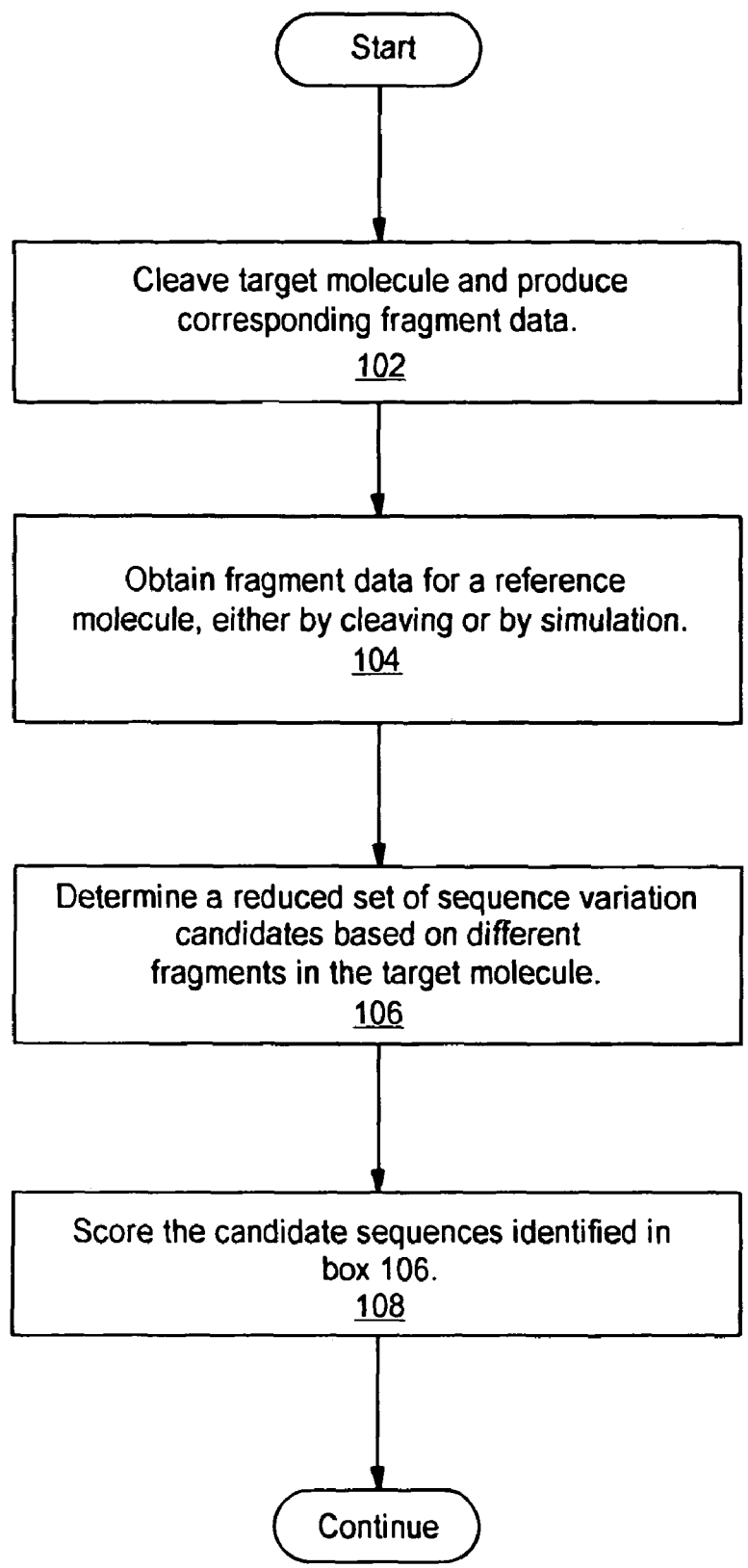
FIG. 1 is a flow diagram that illustrates operations executed by a computer system that performs data analysis by the methods and processes as described herein.

A. Definitions
B. Methods of Generating Fragments
C. Techniques for Polymorphism, Mutation and Sequence Variation Discovery
D. Applications
E. System and Software Method
F. Examples

A. DEFINITIONS

Unless defined otherwise, all technical and scientific terms used herein have the same meaning as is commonly understood by one of skill in the art to which the invention(s) belong. All patents, patent applications, published applications and publications, Genbank sequences, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

As used herein, a molecule refers to any molecular entity and includes, but is not limited to, biopolymers, biomolecules, macromolecules or components or precursors thereof, such as peptides, proteins, organic compounds, oligonucleotides or monomeric units of the peptides, organics, nucleic acids and other macromolecules. A monomeric unit refers to one of the constituents from which the resulting compound is built. Thus, monomeric units include, nucleotides, amino acids, and pharmacophores from which small organic molecules are synthesized.

As used herein, a biomolecule is any molecule that occurs in nature, or derivatives thereof. Biomolecules include biopolymers and macromolecules and all molecules that can be isolated from living organisms and viruses, including, but are not limited to, cells, tissues, prions, animals, plants, viruses, bacteria, prions and other organsims. Biomolecules also include, but are not limited to oligonucleotides, oligonucleosides, proteins, peptides, amino acids, lipids, steroids, peptide nucleic acids (PNAs), oligosaccharides and monosaccharides, organic molecules, such as enzyme cofactors, metal complexes, such as heme, iron sulfur clusters, porphyrins and metal complexes thereof, metals, such as copper, molybedenum, zinc and others.

As used herein, macromolecule refers to any molecule having a molecular weight from the hundreds up to the millions. Macromolecules include, but are not limited to, peptides, proteins, nucleotides, nucleic acids, carbohydrates, and other such molecules that are generally synthesized by biological organisms, but can be prepared synthetically or using recombinant molecular biology methods.

As used herein, biopolymer refers to biomolecules, including macromolecules, composed of two or more monomeric subunits, or derivatives thereof, which are linked by a bond or a macromolecule. A biopolymer can be, for example, a polynucleotide, a polypeptide, a carbohydrate, or a lipid, or derivatives or combinations thereof, for example, a nucleic acid molecule containing a peptide nucleic acid portion or a glycoprotein.

As used herein "nucleic acid" refers to polynucleotides such as deoxyribonucleic acid (DNA) and ribonucleic acid (RNA). The term should also be understood to include, as equivalents, derivatives, variants and analogs of either RNA or DNA made from nucleotide analogs, single (sense or antisense) and double-stranded polynucleotides. Deoxyribonucleotides include deoxyadenosine, deoxycytidine, deoxyguanosine and deoxythymidine. For RNA, the uracil base is uridine.

Reference to a nucleic acid as a "polynucleotide" is used in its broadest sense to mean two or more nucleotides or nucleotide analogs linked by a covalent bond, including single stranded or double stranded molecules. The term "oligonucleotide" also is used herein to mean two or more nucleotides or nucleotide analogs linked by a covalent bond, although those in the art will recognize that oligonucleotides such as PCR primers generally are less than about fifty to one hundred nucleotides in length. The term "amplifying," when used in reference to a nucleic acid, means the repeated copying of a DNA sequence or an RNA sequence, through the use of specific or non-specific means, resulting in an increase in the amount of the specific DNA or RNA sequences intended to be copied.

As used herein, "nucleotides" include, but are not limited to, the naturally occurring nucleoside mono-, di-, and triphosphates: deoxyadenosine mono-, di- and triphosphate; deoxyguanosine mono-, di- and triphosphate; deoxythymidine mono-, di- and triphosphate; and deoxycytidine mono-, di- and triphosphate (referred to herein as dA, dG, dT and dC or A, G, T and C, respectively). Nucleotides also include, but are not limited to, modified nucleotides and nucleotide analogs such as deazapurine nucleotides, e.g., 7-deaza-deoxyguanosine (7-deaza-dG) and 7-deaza-deoxyadenosine (7-deaza-dA) mono-, di- and triphosphates, deutero-deoxythymidine (deutero-dT) mon-, di- and triphosphates, methylated nucleotides e.g., 5-methyldeoxycytidine triphosphate, $^{13}C/^{15}N$ labelled nucleotides and deoxyinosine mono-, di- and triphosphate. For those skilled in the art, it will be clear that modified nucleotides, isotopically enriched, depleted or tagged nucleotides and nucleotide analogs can be obtained using a variety of combinations of functionality and attachment positions.

As used herein, the phrase "chain-elongating nucleotides" is used in accordance with its art recognized meaning. For example, for DNA, chain-elongating nucleotides include 2'deoxyribonucleotides (e.g., dATP, dCTP, dGTP and dTTP) and chain-terminating nucleotides include 2',3'-dideoxyribonucleotides (e.g., ddATP, ddCTP, ddGTP, ddTTP). For RNA, chain-elongating nucleotides include ribonucleotides (e.g., ATP, CTP, GTP and UTP) and chain-terminating nucleotides include 3'-deoxyribonucleotides (e.g., 3'dA, 3'dC, 3'dG and 3'dU) and 2',3'-dideoxyribonucleotides (e.g., ddATP, ddCTP, ddGTP, ddTTP). A complete set of chain elongating nucleotides refers to dATP, dCTP, dGTP and dTTP for DNA, or ATP, CTP, GTP and UTP for RNA. The term "nucleotide" is also well known in the art.

As used herein, the term "nucleotide terminator" or "chain terminating nucleotide" refers to a nucleotide analog that terminates nucleic acid polymer (chain) extension during procedures wherein a DNA or RNA template is being sequenced or replicated. The standard chain terminating nucleotides, i.e., nucleotide terminators include 2',3'-dideoxynucleotides (ddATP, ddGTP, ddCTP and ddTTP, also referred to herein as dideoxynucleotide terminators). As used herein, dideoxynucleotide terminators also include analogs of the standard dideoxynucleotide terminators, e.g., 5-bromo-dideoxyuridine, 5-methyl-dideoxycytidine and dideoxyinosine are analogs of ddTTP, ddCTP and ddGTP, respectively.

The term "polypeptide," as used herein, means at least two amino acids, or amino acid derivatives, including mass modified amino acids, that are linked by a peptide bond, which can be a modified peptide bond. A polypeptide can be translated from a nucleotide sequence that is at least a portion of a coding sequence, or from a nucleotide sequence that is not naturally translated due, for example, to its being in a reading frame other than the coding frame or to its being an intron sequence, a 3' or 5' untranslated sequence, or a regulatory sequence such as a promoter. A polypeptide also can be chemically synthesized and can be modified by chemical or enzymatic methods following translation or chemical synthesis. The terms "protein," "polypeptide" and "peptide" are used interchangeably herein when referring to a translated nucleic acid, for example, a gene product.

As used herein, a fragment of biomolecule, such as biopolymer, into smaller portions than the whole. Fragments can contain from one constituent up to less than all. Typically when cleaving, the fragments will be of a plurality of different sizes such that most will contain more than two constituents, such as a constituent monomer.

As used herein, the term "fragments of a target nucleic acid" refers to cleavage fragments produced by specific physical, chemical or enzymatic cleavage of the target nucleic acid. As used herein, fragments obtained by specific cleavage refers to fragments that are cleaved at a specific position in a target nucleic acid sequence based on the base/sequence specificity of the cleaving reagent (e.g., A, G, C, T or U, or the recognition of modified bases or nucleotides); or the structure of the target nucleic acid; or physical processes, such as ionization by collision-induced dissociation during mass spectrometry; or a combination thereof. Fragments can contain from one up to less than all of the constituent nucleotides of the target nucleic acid molecule. The collection of fragments from such cleavage contains a variety of different size oligonucleotides and nucleotides. Fragments can vary in size, and suitable nucleic acid fragments are typically less that about 2000 nucleotides. Suitable nucleic acid fragments can fall within several ranges of sizes including but not limited to: less than about 1000 bases, between about 100 to about 500 bases, or from about 25 to about 200 bases. In some aspects, fragments of about one nucleotide may be present in the set of fragments obtained by specific cleavage.

As used herein, a target nucleic acid refers to any nucleic acid of interest in a sample. It can contain one or more nucleotides. A target nucleotide sequence refers to a particular sequence of nucleotides in a target nucleic acid molecule.

Detection or identification of such sequence results in detection of the target and can indicate the presence or absence of a particular mutation, sequence variation, or polymorphism. Similarly, a target polypeptide as used herein refers to any polypeptide of interest whose mass is analyzed, for example, by using mass spectrometry to determine the amino acid sequence of at least a portion of the polypeptide, or to determine the pattern of peptide fragments of the target polypeptide produced, for example, by treatment of the polypeptide with one or more endopeptidases. The term "target polypeptide" refers to any polypeptide of interest that is subjected to mass spectrometry for the purposes disclosed herein, for example, for identifying the presence of a polymorphism or a mutation. A target polypeptide contains at least 2 amino acids, generally at least 3 or 4 amino acids, and particularly at least 5 amino acids. A target polypeptide can be encoded by a nucleotide sequence encoding a protein, which can be associated with a specific disease or condition, or a portion of a protein. A target polypeptide also can be encoded by a nucleotide sequence that normally does not encode a translated polypeptide. A target polypeptide can be encoded, for example, from a sequence of dinucleotide repeats or trinucleotide repeats or the like, which can be present in chromosomal nucleic acid, for example, a coding or a non-coding region of a gene, for example, in the telomeric region of a chromosome. The phrase "target sequence" as used herein refers to either a target nucleic acid sequence or a target polypeptide or protein sequence.

A process as disclosed herein also provides a means to identify a target polypeptide by mass spectrometric analysis of peptide fragments of the target polypeptide. As used herein, the term "peptide fragments of a target polypeptide" refers to cleavage fragments produced by specific chemical or enzymatic degradation of the polypeptide. The production of such peptide fragments of a target polypeptide is defined by the primary amino acid sequence of the polypeptide, since chemical and enzymatic cleavage occurs in a sequence specific manner. Peptide fragments of a target polypeptide can be produced, for example, by contacting the polypeptide, which can be immobilized to a solid support, with a chemical agent such as cyanogen bromide, which cleaves a polypeptide at methionine residues, or hydroxylamine at high pH, which can cleave an Asp-Gly peptide bond; or with an endopeptidase such as trypsin, which cleaves a polypeptide at Lys or Arg residues.

The identity of a target polypeptide can be determined by comparison of the molecular mass or sequence with that of a reference or known polypeptide. For example, the mass spectra of the target and known polypeptides can be compared.

As used herein, the term "corresponding or known polypeptide or nucleic acid" is a known polypeptide or nucleic acid generally used as a control to determine, for example, whether a target polypeptide or nucleic acid is an allelic variant of the corresponding known polypeptide or nucleic acid. It should be recognized that a corresponding known protein or nucleic acid can have substantially the same amino acid or base sequence as the target polypeptide, or can be substantially different. For example, where a target polypeptide is an allelic variant that differs from a corresponding known protein by a single amino acid difference, the amino acid sequences of the polypeptides will be the same except for the single amino acid difference. Where a mutation in a nucleic acid encoding the target polypeptide changes, for example, the reading frame of the encoding nucleic acid or introduces or deletes a STOP codon, the sequence of the target polypeptide can be substantially different from that of the corresponding known polypeptide.

As used herein, a reference biomolecule refers to a biomolecule, which is generally, although not necessarily, to which a target biomolecule is compared. Thus, for example, a reference nucleic acid is a nucleic acid to which the target nucleic acid is compared in order to identify potential or actual sequence variations in the target nucleic acid relative to the reference nucleic acid. Reference nucleic acids typically are of known sequence or of a sequence that can be determined.

As used herein, a reference polypeptide is a polypeptide to which the target polypeptide is compared in order to identify the polypeptide in methods that do not involve sequencing the polypeptide. Reference polypeptides typically are known polypeptides. Reference sequence, as used herein, refers to a reference nucleic acid or a reference polypeptide or protein sequence.

As used herein, transcription-based processes include "in vitro transcription system", which refers to a cell-free system containing an RNA polymerase and other factors and reagents necessary for transcription of a DNA molecule operably linked to a promoter that specifically binds an RNA polymerase. An in vitro transcription system can be a cell extract, for example, a eukaryotic cell extract. The term "transcription," as used herein, generally means the process by which the production of RNA molecules is initiated, elongated and terminated based on a DNA template. In addition, the process of "reverse transcription," which is well known in the art, is considered as encompassed within the meaning of the term "transcription" as used herein. Transcription is a polymerization reaction that is catalyzed by DNA-dependent or RNA-dependent RNA polymerases. Examples of RNA polymerases include the bacterial RNA polymerases, SP6 RNA polymerase, T3 RNA polymerase, T3 RNA polymerase, and T7 RNA polymerase.

As used herein, the term "translation" describes the process by which the production of a polypeptide is initiated, elongated and terminated based on an RNA template. For a polypeptide to be produced from DNA, the DNA must be transcribed into RNA, then the RNA is translated due to the interaction of various cellular components into the polypeptide. In prokaryotic cells, transcription and translation are "coupled", meaning that RNA is translated into a polypeptide during the time that it is being transcribed from the DNA. In eukaryotic cells, including plant and animal cells, DNA is transcribed into RNA in the cell nucleus, then the RNA is processed into mRNA, which is transported to the cytoplasm, where it is translated into a polypeptide.

The term "isolated" as used herein with respect to a nucleic acid, including DNA and RNA, refers to nucleic acid molecules that are substantially separated from other macromolecules normally associated with the nucleic acid in its natural state. An isolated nucleic acid molecule is substantially separated from the cellular material normally associated with it in a cell or, as relevant, can be substantially separated from bacterial or viral material; or from culture medium when produced by recombinant DNA techniques; or from chemical precursors or other chemicals when the nucleic acid is chemically synthesized. In general, an isolated nucleic acid molecule is at least about 50% enriched with respect to its natural state, and generally is about 70% to about 80% enriched, particularly about 90% or 95% or more. Preferably, an isolated nucleic acid constitutes at least about 50% of a sample containing the nucleic acid, and can be at least about 70% or 80% of the material in a sample, particularly at least about 90% to 95% or greater of the sample. An isolated nucleic acid can be a nucleic acid molecule that does not occur in nature and, therefore, is not found in a natural state.

The term "isolated" also is used herein to refer to polypeptides that are substantially separated from other macromolecules normally associated with the polypeptide in its natural state. An isolated polypeptide can be identified based on its being enriched with respect to materials it naturally is associated with or its constituting a fraction of a sample containing the polypeptide to the same degree as defined above for an "isolated" nucleic acid, i.e., enriched at least about 50% with respect to its natural state or constituting at least about 50% of a sample containing the polypeptide. An isolated polypeptide, for example, can be purified from a cell that normally expresses the polypeptide or can produced using recombinant DNA methodology.

As used herein, "structure" of the nucleic acid includes but is not limited to secondary structures due to non-Watson-Crick base pairing (see, e.g., Seela, F. and A. Kehne (1987) *Biochemistry*, 26, 2232-2238.) and structures, such as hairpins, loops and bubbles, formed by a combination of base-paired and non base-paired or mis-matched bases in a nucleic acid.

As used herein, epigenetic changes refer to variations in a target sequence relative to a reference sequence (e.g., a mutant sequence relative to the wild-type sequence) that are not dependent on changes in the identity of the natural bases (A, G, C, T/U) or the twenty natural amino acids. Such variations include, but are not limited to, e.g., differences in the presence of modified bases or methylated bases between a target nucleic acid sequence and a reference nucleic acid sequence. Epigenetic changes refer to mitotically and/or meiotically heritable changes in gene function or changes in higher order nucleic acid structure that cannot be explained by changes in nucleic acid sequence. Examples of systems that are subject to epigenetic variation or change include, but are not limited to, DNA methylation patterns in animals, histone modification and the Polycomb-trithorax group (Pc-G/tx) protein complexes. Epigenetic changes usually, although not necessarily, lead to changes in gene expression that are usually, although not necessarily, inheritable.

As used herein, a "primer" refers to an oligonucleotide that is suitable for hybridizing, chain extension, amplification and sequencing. Similarly, a probe is a primer used for hybridization. The primer refers to a nucleic acid that is of low enough mass, typically about between about 5 and 200 nucleotides, generally about 70 nucleotides or less than 70, and of sufficient size to be conveniently used in the methods of amplification and methods of detection and sequencing provided herein. These primers include, but are not limited to, primers for detection and sequencing of nucleic acids, which require a sufficient number nucleotides to form a stable duplex, typically about 6-30 nucleotides, about 10-25 nucleotides and/or about 12-20 nucleotides. Thus, for purposes herein, a primer is a sequence of nucleotides contains of any suitable length, typically containing about 6-70 nucleotides, 12-70 nucleotides or greater than about 14 to an upper limit of about 70 nucleotides, depending upon sequence and application of the primer.

As used herein, reference to mass spectrometry encompasses any suitable mass spectrometric format known to those of skill in the art. Such formats include, but are not limited to, Matrix-Assisted Laser Desorption/Ionization, Time-of-Flight (MALDI-TOF), Electrospray (ES), IR-MALDI (see, e.g., published International PCT application No. 99/57318 and U.S. Pat. No. 5,118,937), Ion Cyclotron Resonance (ICR), Fourier Transform and combinations thereof. MALDI, particular UV and IR, are among the preferred formats.

As used herein, mass spectrum refers to the presentation of data obtained from analyzing a biopolymer or fragment thereof by mass spectrometry either graphically or encoded numerically.

As used herein, pattern or fragmentation pattern or fragmentation spectrum with reference to a mass spectrum or mass spectrometric analyses, refers to a characteristic distribution and number of signals (such as peaks or digital representations thereof). In general, a fragmentation pattern as used herein refers to a set of fragments that are generated by specific cleavage of a biomolecule such as, but not limited to, nucleic acids and proteins.

As used herein, signal, mass signal or output signal in the context of a mass spectrum or any other method that measures mass and analysis thereof refers to the output data, which is the number or relative number of molecules having a particular mass. Signals include "peaks" and digital representations thereof.

As used herein, the term "peaks" refers to prominent upward projections from a baseline signal of a mass spectrometer spectrum ("mass spectrum") which corresponds to the mass and intensity of a fragment. Peaks can be extracted from a mass spectrum by a manual or automated "peak finding" procedure.

As used herein, the mass of a peak in a mass spectrum refers to the mass computed by the "peak finding" procedure.

As used herein, the intensity of a peak in a mass spectrum refers to the intensity computed by the "peak finding" procedure that is dependent on parameters including, but not limited to, the height of the peak in the mass spectrum and its signal-to-noise ratio.

As used herein, "analysis" refers to the determination of certain properties of a single oligonucleotide or polypeptide, or of mixtures of oligonucleotides or polypeptides. These properties include, but are not limited to, the nucleotide or amino acid composition and complete sequence, the existence of single nucleotide polymorphisms and other mutations or sequence variations between more than one oligonucleotide or polypeptide, the masses and the lengths of oligonucleotides or polypeptides and the presence of a molecule or sequence within a molecule in a sample.

As used herein, "multiplexing" refers to the simultaneous determination of more than one oligonucleotide or polypeptide molecule, or the simultaneous analysis of more than one oligonucleotide or oligopeptide, in a single mass spectrometric or other mass measurement, i.e., a single mass spectrum or other method of reading sequence.

As used herein, amplifying refers to means for increasing the amount of a biopolymer, especially nucleic acids. Based on the 5' and 3' primers that are chosen, amplification also serves to restrict and define the region of the genome which is subject to analysis. Amplification can be by any means known to those skilled in the art, including use of the polymerase chain reaction (PCR), etc. Amplification, e.g., PCR must be done quantitatively when the frequency of polymorphism is required to be determined.

As used herein, "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles. A polymorphic region can also be several nucleotides in length. Thus, a polymorphism, e.g. genetic variation, refers to a variation in the sequence of a gene in the genome amongst a population, such as allelic variations and other variations that arise or are observed. Thus, a polymorphism refers to the occurrence of two or more genetically determined alternative sequences or alleles in a population. These differences can occur in coding and non-coding portions of the genome, and can be manifested or detected as differences in nucleic acid sequences, gene expression, including, for example transcription, processing, translation, transport, protein processing, trafficking, DNA synthesis, expressed proteins, other gene products or products of biochemical pathways or in post-translational modifications and any other differences manifested amongst members of a population. A single nucleotide polymorphism (SNP) refers to a polymorphism that arises as the result of a single base change, such as an insertion, deletion or change (substitution) in a base.

A polymorphic marker or site is the locus at which divergence occurs. Such site can be as small as one base pair (an SNP). Polymorphic markers include, but are not limited to, restriction fragment length polymorphisms, variable number of tandem repeats (VNTR's), hypervariable regions, minisatellites, dinucleotide repeats, trinucleotide repeats, tetranucleotide repeats and other repeating patterns, simple sequence repeats and insertional elements, such as Alu. Polymorphic forms also are manifested as different mendelian alleles for a gene. Polymorphisms can be observed by differences in proteins, protein modifications, RNA expression modification, DNA and RNA methylation, regulatory factors that alter gene expression and DNA replication, and any other manifestation of alterations in genomic nucleic acid or organelle nucleic acids.

As used herein, "polymorphic gene" refers to a gene having at least one polymorphic region.

As used herein, "allele", which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has at least two different alleles of a gene, the subject is said to be heterozygous for the gene. Alleles of a specific gene can differ from each other in a single nucleotide, or several nucleotides, and can include substitutions, deletions, and insertions of nucleotides. An allele of a gene can also be a form of a gene containing a mutation.

As used herein, "predominant allele" refers to an allele that is represented in the greatest frequency for a given population. The allele or alleles that are present in lesser frequency are referred to as allelic variants.

As used herein, changes in a nucleic acid sequence known as mutations can result in proteins with altered or in some cases even lost biochemical activities; this in turn can cause genetic disease. Mutations include nucleotide deletions, insertions or alterations/substitutions (i.e. point mutations). Point mutations can be either "missense", resulting in a change in the amino acid sequence of a protein or "nonsense" coding for a stop codon and thereby leading to a truncated protein.

As used herein, a sequence variation contains one or more nucleotides or amino acids that are different in a target nucleic acid or protein sequence when compared to a reference nucleic acid or protein sequence. The sequence variation can include, but is not limited to, a mutation, a polymorphism, or sequence differences between a target sequence and a reference sequence that belong to different organisms. A sequence variation will in general, although not always, contain a subset of the complete set of nucleotide, amino acid, or other biopolymer monomeric unit differences between the target sequence and the reference sequence.

As used herein, additional or missing peaks or signals are peaks or signals corresponding to fragments of a target sequence that are either present or absent, respectively, relative to fragments obtained by actual or simulated cleavage of a reference sequence, under the same cleavage reaction conditions. Besides missing or additional signals, differences between target fragments and reference fragments can be manifested as other differences including, but not limited to, differences in peak intensities (height, area, signal-to-noise or combinations thereof) of the signals.

As used herein, different fragments are fragments of a target sequence that are different relative to fragments obtained by actual or simulated cleavage of a reference sequence, under the same cleavage reaction conditions. Different fragments can be fragments that are missing in the target fragment pattern relative to a reference fragment pattern, or are additionally present in the target fragmentation pattern relative to the reference fragmentation pattern. Besides missing or additional fragments, different fragments can also be differences between the target fragmentation pattern and the reference fragmentation pattern that are qualitative including, but not limited to, differences that lead to differences in peak intensities (height, area, signal-to-noise or combinations thereof) of the signals corresponding to the different fragments.

As used herein, the term "compomer" refers to the composition of a sequence fragment in terms of its monomeric component units. For nucleic acids, compomer refers to the base composition of the fragment with the monomeric units being bases; the number of each type of base can be denoted by $B_n$ (ie: $A_a C_c G_g T_t$, with $A_0 C_0 G_0 T_0$ representing an "empty" compomer or a compomer containing no bases). A natural compomer is a compomer for which all component monomeric units (e.g., bases for nucleic acids and amino acids for proteins) are greater than or equal to zero. For purposes of comparing sequences to determine sequence variations, however, in the methods provided herein, "unnatural" compomers containing negative numbers of monomeric units may be generated by the algorithm. For polypeptides, a compomer refers to the amino acid composition of a polypeptide fragment, with the number of each type of amino acid similarly denoted. A compomer corresponds to a sequence if the number and type of bases in the sequence can be added to obtain the composition of the compomer. For example, the compomer $A_2 G_3$ corresponds to the sequence AGGAG. In general, there is a unique compomer corresponding to a sequence, but more than one sequence can correspond to the same compomer. For example, the sequences AGGAG, AAGGG, GGAGA, etc. all correspond to the same compomer $A_2 G_3$, but for each of these sequences, the corresponding compomer is unique, i.e., $A_2 G_3$.

As used herein, witness compomers or compomer witnesses refer to all possible compomers whose masses differ by a value that is less than or equal to a sufficiently small mass difference from the actual mass of each different fragment generated in the target cleavage reaction relative to the same reference cleavage reaction. A sufficiently small mass difference can be determined empirically, if needed, and is generally the resolution of the mass measurement. For example, for mass spectrometry measurements, the value of the sufficiently small mass difference is a function of parameters including, but not limited to, the mass of the different fragment (as measured by its signal) corresponding to a witness compomer, peak separation between fragments whose masses differ by a single nucleotide in type or length, and the absolute resolution of the mass spectrometer. Cleavage reactions specific for one or more of the four nucleic acid bases (A, G, C, T or U for RNA, or modifications thereof) or of the twenty amino acids or modifications thereof, can be used to generate data sets containing the possible witness compomers for each different fragment such that the masses of the possible witness compomers near or equal the actual measured mass of each different fragment by a value that is less than or equal to a sufficiently small mass difference.

As used herein, two or more sequence variations of a target sequence relative to a reference sequence are said to interact with each other if the differences between the fragmentation pattern of the target sequence and the reference sequence for a specific cleavage reaction are not a simple sum of the differences representing each sequence variation in the target sequence. For sequence variations in the target sequence that do not interact with each other, the separation (distance) between sequence variations along the target sequence is sufficient for each sequence variation to generate a distinct different fragment (of the target sequence relative to the reference sequence) in a specific cleavage reaction, the differences in the fragmentation pattern of the target sequence relative to the reference sequence represents the sum of all sequence variations in the target sequence relative to the reference sequence.

As used herein, a sufficiently small mass difference is the maximum mass difference between the measured mass of an identified different fragment and the mass of a compomer such that the compomer can be considered as a witness compomer for the identified different fragment. A sufficiently small mass difference can be determined empirically, if needed, and is generally the resolution of the mass measurement. For example, for mass spectrometry measurements, the value of the sufficiently small mass difference is a function of parameters including, but not limited to, the mass of the different fragment (as measured by its signal) corresponding to a witness compomer, the peak separation between fragments whose masses differ by a single nucleotide in type or length, and the absolute resolution of the mass spectrometer.

As used herein, a substring or subsequence $s[i,j]$ denotes a cleavage fragment of the string s, which denotes the full length nucleic acid or protein sequence. As used herein, i and j are integers that denote the start and end positions of the substring. For example, for a nucleic acid substring, i and j can denote the base positions in the nucleic acid sequence where the substring begins and ends, respectively. As used herein, $c[i,j]$ refers to a compomer corresponding to $s[i,j]$.

As used herein, sequence variation order k refers to the sequence variation candidates of the target sequence constructed by the techniques provided herein, where the sequence variation candidates contain at most k mutations, polymorphisms, or other sequence variations, including, but not limited to, sequence variations between organisms, insertions, deletions and substitutions, in the target sequence relative to a reference sequence. The value of k is dependent on a number of parameters including, but not limited to, the expected type and number of sequence variations between a reference sequence and the target sequence, e.g., whether the sequence variation is a single base or multiple bases, whether sequence variations are present at one location or at more than one location on the target sequence relative to the reference sequence, or whether the sequence variations interact or do not interact with each in the target sequence. For example, for the detection of SNPs, the value of k is usually, although not necessarily, 1 or 2. As another example, for the detection of mutations and in resequencing, the value of k is usually, although not necessarily, 3 or higher.

As used herein, given a specific cleavage reaction of a base, amino acid, or other feature X recognized by the cleavage reagent in a string s, then the boundary $b[i,j]$ of the substring $s[i,j]$ or the corresponding compomer $c[i,j]$ refers to a set of markers indicating whether cleavage of string s does not take place immediately outside the substring $s[i,j]$. Possible markers are L, indicating whether "s is not cleaved directly before i", and R, indicating whether "s is not cleaved directly after j". Thus, $b[i,j]$ is a subset of the set $\{L,R\}$ that contains L if and only if X is present at position i−1 of the string s, and contains R if and only if X is present at position j+1 of the string s. #b denotes the number of elements in the set b, which can be 0, 1, or 2, depending on whether the substring $s[i,j]$ is specifically cleaved at both immediately flanking positions (i.e., at positions i−1 and j+1), at one immediately flanking position (i.e., at either position i−1 or j+1) or at no immediately flanking position (i.e., at neither position i−1 nor j+1).

As used herein, a compomer boundary or boundary b is a subset of the set $\{L,R\}$ as defined above for $b[i,j]$. Possible values for b are the empty set $\{\}$, i.e., the number of elements in b (#b) is 0; $\{L\}$, $\{R\}$, i.e., #b is 1; and $\{L,R\}$, i.e., #b is 2.

As used herein, bounded compomers refers to the set of all compomers c that correspond to the set of subsequences of a reference sequence, with a boundary that indicates whether or not cleavage sites are present at the two ends of each subsequence. The set of bounded compomers can be compared against possible compomer witnesses to construct all possible sequence variations of a target sequence relative to a reference sequence. For example, (c,b) refers to a 'bounded compomer' that contains a compomer c and a boundary b.

As used herein, C refers to the set of all bounded compomers within the string s; i.e., for all possible substrings $s[i,j]$, find the bounded compomers $(c[i,j],b[i,j])$ and these will belong to the set C. C can be represented as $C:=\{(c[i,j], b[i,j]): 1 \leq i \leq j \leq \text{length of s}\}$ As used herein, $ord[i,j]$ refers to the number of times substring $s[i,j]$ will be cleaved in a particular cleavage reaction.

As used herein, given compomers c,c' corresponding to fragments f,f', d(c,c') is a function that determines the minimum number of sequence variations, polymorphisms or mutations (insertions, deletions, substitutions) that are needed to convert c to c', taken over all potential fragments f,f' corresponding to compomers c,c', where c is a compomer of a fragment s of the reference biomolecule and c' is the compomer of a fragment s' of the target biomolecule resulting from a sequence variation of the s fragment. As used herein, d(c,c') is equivalent to d(c',c).

For a bounded compomer (c,b) constructed from the set C, The function D(c',c,b) measures the minimum number of sequence variations relative to a reference sequence that is needed to generate the compomer witness c'. D(c',c,b) can be represented as D(c',c,b):=d(c',c)+#b. As used herein, D(c',c,b) is equivalent to D(c,c',b)

As used herein, $C_k$ is a subset of C such that compomers for substrings containing more than k number of sequence variations of the cut string will be excluded from the set C. Thus, if there is a sequence variation containing at most k insertions, deletions, and substitutions, and if c' is a compomer corresponding to a peak witness of this sequence variation, then there exists a bounded compomer (c,b) in $C_k$ such that D(c', c,b)≤k. $C_k$ can be represented as $C_k:=\{(c[i,j], b[i,j]): 1 \leq i \leq j \leq \text{length of s, and } ord[i,j]+\#b[i,j] \leq k\}$ The algorithm provided herein is based on this reduced set of compomers corresponding to possible sequence variations.

As used herein, $L_\Delta$ or $L\_\Delta$ denotes a list of peaks or signals corresponding to fragments that are different in a target cleavage reaction relative to the same reference cleavage reaction. The differences include, but are not limited to, signals that are present or absent in the target fragment signals relative to the reference fragment signals, and signals that differ in intensity between the target fragment signals and the reference fragment signals.

As used herein, sequence variation candidate refers to a potential sequence of the target sequence containing one or more sequence variations. The probability of a sequence variation candidate being the actual sequence of the target biomolecule containing one or more sequence variations is measured by a score.

As used herein, a reduced set of sequence variation candidates refers to a subset of all possible sequence variations in the target sequence that would generate a given set of fragments upon specific cleavage of the target sequence. A reduced set of sequence variation candidates can be obtained by creating, from the set of all possible sequence variations of a target sequence that can generate a particular fragmentation pattern (as detected by measuring the masses of the fragments) in a particular specific cleavage reaction, a subset containing only those sequence variations that generate fragments of the target sequence that are different from the fragments generated by actual or simulated cleavage of a reference sequence in the same specific cleavage reaction.

As used herein, fragments that are consistent with a particular sequence variation in a target molecule refer to those different fragments that are obtained by cleavage of a target molecule in more than one reaction using more than one cleavage reagent whose characteristics, including, but not limited to, mass, intensity or signal-to-noise ratio, when analyzed according to the methods provided herein, indicate the presence of the same sequence variation in the target molecule.

As used herein, scoring or a score refers to a calculation of the probability that a particular sequence variation candidate is actually present in the target nucleic acid or protein sequence. The value of a score is used to determine the sequence variation candidate that corresponds to the actual target sequence. Usually, in a set of samples of target sequences, the highest score represents the most likely sequence variation in the target molecule, but other rules for selection can also be used, such as detecting a positive score, when a single target sequence is present.

As used herein, simulation (or simulating) refers to the calculation of a fragmentation pattern based on the sequence of a nucleic acid or protein and the predicted cleavage sites in the nucleic acid or protein sequence for a particular specific cleavage reagent. The fragmentation pattern can be simulated as a table of numbers (for example, as a list of peaks corresponding to the mass signals of fragments of a reference biomolecule), as a mass spectrum, as a pattern of bands on a gel, or as a representation of any technique that measures mass distribution. Simulations can be performed in most instances by a computer program.

As used herein, simulating cleavage refers to an in silico process in which a target molecule or a reference molecule is virtually cleaved.

As used herein, in silico refers to research and experiments performed using a computer. In silico methods include, but are not limited to, molecular modelling studies, biomolecular docking experiments, and virtual representations of molecular structures and/or processes, such as molecular interactions.

As used herein, a subject includes, but is not limited to, animals, plants, bacteria, viruses, parasites and any other organism or entity that has nucleic acid. Among subjects are mammals, preferably, although not necessarily, humans. A patient refers to a subject afflicted with a disease or disorder.

As used herein, a phenotype refers to a set of parameters that includes any distinguishable trait of an organism. A phenotype can be physical traits and can be, in instances in which the subject is an animal, a mental trait, such as emotional traits.

As used herein, "assignment" refers to a determination that the position of a nucleic acid or protein fragment indicates a particular molecular weight and a particular terminal nucleotide or amino acid.

As used herein, "a" refers to one or more.

As used herein, "plurality" refers to two or more polynucleotides or polypeptides, each of which has a different sequence. Such a difference can be due to a naturally occurring variation among the sequences, for example, to an allelic variation in a nucleotide or an encoded amino acid, or can be due to the introduction of particular modifications into various sequences, for example, the differential incorporation of mass modified nucleotides into each nucleic acid or protein in a plurality.

As used herein, an array refers to a pattern produced by three or more items, such as three or more loci on a solid support.

As used herein, "unambiguous" refers to the unique assignment of peaks or signals corresponding to a particular sequence variation, such as a mutation, in a target molecule and, in the event that a number of molecules or mutations are multiplexed, that the peaks representing a particular sequence variation can be uniquely assigned to each mutation or each molecule.

As used herein, a data processing routine refers to a process, that can be embodied in software, that determines the biological significance of acquired data (i.e., the ultimate results of the assay). For example, the data processing routine can make a genotype determination based upon the data collected. In the systems and methods herein, the data processing routine also controls the instrument and/or the data collection routine based upon the results determined. The data processing routine and the data collection routines are integrated and provide feedback to operate the data acquisition by the instrument, and hence provide the assay-based judging methods provided herein.

As used herein, a plurality of genes includes at least two, five, 10, 25, 50, 100, 250, 500, 1000, 2,500, 5,000, 10,000, 100,000, 1,000,000 or more genes. A plurality of genes can include complete or partial genomes of an organism or even a plurality thereof. Selecting the organism type determines the genome from among which the gene regulatory regions are selected. Exemplary organisms for gene screening include animals, such as mammals, including human and rodent, such as mouse, insects, yeast, bacteria, parasites, and plants.

As used herein, "specifically hybridizes" refers to hybridization of a probe or primer only to a target sequence preferentially to a non-target sequence. Those of skill in the art are familiar with parameters that affect hybridization; such as temperature, probe or primer length and composition, buffer composition and salt concentration and can readily adjust these parameters to achieve specific hybridization of a nucleic acid to a target sequence.

As used herein, "sample" refers to a composition containing a material to be detected. In a preferred embodiment, the sample is a "biological sample." The term "biological sample" refers to any material obtained from a living source, for example, an animal such as a human or other mammal, a plant, a bacterium, a fungus, a protist or a virus. The biological sample can be in any form, including a solid material such as a tissue, cells, a cell pellet, a cell extract, or a biopsy, or a biological fluid such as urine, blood, saliva, amniotic fluid, exudate from a region of infection or inflammation, or a mouth wash containing buccal cells, urine, cerebral spinal fluid and synovial fluid and organs. Preferably solid materials are mixed with a fluid. In particular, herein, the sample refers to a mixture of matrix used for mass spectrometric analyses and biological material such as nucleic acids. Derived from means that the sample can be processed, such as by purification or isolation and/or amplification of nucleic acid molecules.

As used herein, a composition refers to any mixture. It can be a solution, a suspension, liquid, powder, a paste, aqueous, non-aqueous or any combination thereof.

As used herein, a combination refers to any association between two or among more items.

As used herein, the term "1¼-cutter" refers to a restriction enzyme that recognizes and cleaves a 2 base stretch in the nucleic acid, in which the identity of one base position is fixed and the identity of the other base position is any three of the four naturally occurring bases.

As used herein, the term "1½-cutter" refers to a restriction enzyme that recognizes and cleaves a 2 base stretch in the nucleic acid, in which the identity of one base position is fixed and the identity of the other base position is any two out of the four naturally occurring bases.

As used herein, the term "2 cutter" refers to a restriction enzyme that recognizes and cleaves a specific nucleic acid site that is 2 bases long.

As used herein, the term "AFLP" refers to amplified fragment length polymorphism, and the term "RFLP" refers to restriction fragment length polymorphism.

As used herein, the term "amplicon" refers to a region of DNA that can be replicated.

As used herein, the term "complete cleavage" or "total cleavage" refers to a cleavage reaction in which all the cleavage sites recognized by a particular cleavage reagent are cut to completion.

As used herein, the term "false positives" refers to mass signals that are from background noise and not generated by specific actual or simulated cleavage of a nucleic acid or protein.

As used herein, the term "false negatives" refers to actual mass signals that are missing from an actual fragmentation spectrum but can be detected in the corresponding simulated spectrum.

As used herein, the term "partial cleavage" refers to a reaction in which only a fraction of the cleavage sites of a particular cleavage reagent are actually cut by the cleavage reagent.

As used herein, cleave means any manner in which a nucleic acid or protein molecule is cut into smaller pieces. The cleavage recognition sites can be one, two or more bases long. The cleavage means include physical cleavage, enzymatic cleavage, chemical cleavage and any other way smaller pieces of a nucleic acid are produced.

As used herein, cleavage conditions or cleavage reaction conditions refers to the set of one or more cleavage reagents that are used to perform actual or simulated cleavage reactions, and other parameters of the reactions including, but not limited to, time, temperature, pH, or choice of buffer.

As used herein, uncleaved cleavage sites means cleavage sites that are known recognition sites for a cleavage reagent but that are not cut by the cleavage reagent under the conditions of the reaction, e.g., time, temperature, or modifications of the bases at the cleavage recognition sites to prevent cleavage by the reagent.

As used herein, complementary cleavage reactions refers to cleavage reactions that are carried out or simulated on the same target or reference nucleic acid or protein using different cleavage reagents or by altering the cleavage specificity of the same cleavage reagent such that alternate cleavage patterns of the same target or reference nucleic acid or protein are generated.

As used herein, a combination refers to any association between two or among more items or elements.

As used herein, a composition refers to a any mixture. It can be a solution, a suspension, liquid, powder, a paste, aqueous, non-aqueous or any combination thereof.

As used herein, fluid refers to any composition that can flow. Fluids thus encompass compositions that are in the form of semi-solids, pastes, solutions, aqueous mixtures, gels, lotions, creams and other such compositions.

As used herein, a cellular extract refers to a preparation or fraction which is made from a lysed or disrupted cell.

As used herein, a kit is combination in which components are packaged optionally with instructions for use and/or reagents and apparatus for use with the combination.

As used herein, a system refers to the combination of elements with software and any other elements for controlling and directing methods provided herein.

As used herein, software refers to computer readable program instructions that, when executed by a computer, performs computer operations. Typically, software is provided on a program product containing program instructions recorded on a computer readable medium, such as but not limited to, magnetic media including floppy disks, hard disks, and magnetic tape; and optical media including CD-ROM discs, DVD discs, magneto-optical discs, and other such media on which the program instructions can be recorded.

For clarity of disclosure, and not by any way of limitation, the detailed description is divided into the subsections below.

B. METHODS OF GENERATING FRAGMENTS

Nucleic Acid Fragmentation

Fragmentation of nucleic acids is known in the art and can be achieved in many ways. For example, polynucleotides composed of DNA, RNA, analogs of DNA and RNA or combinations thereof, can be fragmented physically, chemically, or enzymatically, as long as the fragmentation is obtained by cleavage at a specific site in the target nucleic acid. Fragments can be cleaved at a specific position in a target nucleic acid sequence based on (i) the base specificity of the cleaving reagent (e.g., A, G, C, T or U, or the recognition of modified bases or nucleotides); or (ii) the structure of the target nucleic acid; or (iii) a combination of both, are generated from the target nucleic acid. Fragments can vary in size, and suitable fragments are typically less that about 2000 nucleic acids. Suitable fragments can fall within several ranges of sizes including but not limited to: less than about 1000 bases, between about 100 to about 500 bases, or from about 25 to about 200 bases. In some aspects, fragments of about one nucleic acid are desirable.

Polynucleotides can be fragmented by chemical reactions including for example, hydrolysis reactions including base and acid hydrolysis. Alkaline conditions can be used to fragment polynucleotides comprising RNA because RNA is unstable under alkaline conditions. See, e.g., Nordhoff et al. (1993) *Ion stability of nucleic acids in infrared matrix-assisted laser desorption/ionization mass spectrometry, Nucl. Acids Res.*, 21(15):3347-57. DNA can be hydrolyzed in the presence of acids, typically strong acids such as 6M HCl. The temperature can be elevated above room temperature to facilitate the hydrolysis. Depending on the conditions and length of reaction time, the polynucleotides can be fragmented into various sizes including single base fragments. Hydrolysis can, under rigorous conditions, break both of the phosphate ester bonds and also the N-glycosidic bond between the deoxyribose and the purines and pyrimidine bases.

An exemplary acid/base hydrolysis protocol for producing polynucleotide fragments is described in Sargent et al. (1988) *Methods Enzymol.*, 152:432. Briefly, 1 g of DNA is dissolved in 50 mL 0.1 N NaOH. 1.5 mL concentrated HCl is added, and the solution is mixed quickly. DNA will precipitate immediately, and should not be stirred for more than a few seconds to prevent formation of a large aggregate. The sample is incubated at room temperature for 20 minutes to partially depurinate the DNA. Subsequently, 2 mL 10 N NaOH (OH— concentration to 0.1 N) is added, and the sample is stirred till DNA redissolves completely. The sample is then incubated at 65° C. for 30 minutes to hydrolyze the DNA. Typical sizes range from about 250-1000 nucleotides but can vary lower or higher depending on the conditions of hydrolysis.

Another process whereby nucleic acid molecules are chemically cleaved in a base-specific manner is provided by A. M. Maxam and W. Gilbert, *Proc. Natl. Acad. Sci. USA* 74:560-64, 1977, and incorporated by reference herein. Individual reactions were devised to cleave preferentially at guanine, at adenine, at cytosine and thymine, and at cytosine alone.

Polynucleotides can also be cleaved via alkylation, particularly phosphorothioate-modified polynucleotides. K. A. Browne (2002) *Metal ion-catalyzed nucleic Acid alkylation and fragmentation.* J. Am. Chem. Soc. 124(27):7950-62. Alkylation at the phosphorothioate modification renders the polynucleotide susceptible to cleavage at the modification site. I. G. Gut and S. Beck describe methods of alkylating DNA for detection in mass spectrometry. I. G. Gut and S. Beck (1995) *A procedure for selective DNA alkylation and detection by mass spectrometry.* Nucleic Acids Res. 23(8): 1367-73. Another approach uses the acid lability of P3'-N5'-phosphoroamidate-containing DNA (Shchepinov et al., "Matrix-induced fragmentation of P3'-N5'-phosphoroamidate-containing DNA: high-throughput MALDI-TOF analysis of genomic sequence polymorphisms," Nucleic Acids Res. 25: 3864-3872 (2001). Either dCTP or dTTP are replaced by their analog P—N modified nucleoside triphosphates and are introduced into the target sequence by primer extension reaction subsequent to PCR. Subsequent acidic reaction conditions produce base-specific cleavage fragments. In order to minimize depurination of adenine and guanine residues under the acidic cleavage conditions required, 7-deaza analogs of dA and dG can be used.

Single nucleotide mismatches in DNA heteroduplexes can be cleaved by the use of osmium tetroxide and piperidine, providing an alternative strategy to detect single base substitutions, generically named the "Mismatch Chemical Cleavage" (MCC) (Gogos et al., Nucl. Acids Res., 18: 6807-6817 [1990]).

Polynucleotide fragmentation can also be achieved by irradiating the polynucleotides. Typically, radiation such as gamma or x-ray radiation will be sufficient to fragment the polynucleotides. The size of the fragments can be adjusted by adjusting the intensity and duration of exposure to the radiation. Ultraviolet radiation can also be used. The intensity and duration of exposure can also be adjusted to minimize undesirable effects of radiation on the polynucleotides. Boiling polynucleotides can also produce fragments. Typically a solution of polynucleotides is boiled for a couple hours under constant agitation. Fragments of about 500 bp can be achieved. The size of the fragments can vary with the duration of boiling.

Polynucleotide fragments can result from enzymatic cleavage of single or multi-stranded polynucleotides. Multi-stranded polynucleotides include polynucleotide complexes comprising more than one strand of polynucleotides, including for example, double and triple stranded polynucleotides. Depending on the enzyme used, the polynucleotides are cut nonspecifically or at specific nucleotides sequences. Any enzyme capable of cleaving a polynucleotide can be used including but not limited to endonucleases, exonucleases, ribozymes, and DNAzymes. Enzymes useful for fragmenting polynucleotides are known in the art and are commercially available. See for example Sambrook, J., Russell, D. W., *Molecular Cloning: A Laboratory Manual*, the third edition, Cold Spring Harbor Laboratory Press, Cold Spring Harbor, N.Y., 2001, which is incorporated herein by reference. Enzymes can also be used to degrade large polynucleotides into smaller fragments.

Endonucleases are an exemplary class of enzymes useful for fragmenting polynucleotides. Endonucleases have the capability to cleave the bonds within a polynucleotide strand. Endonucleases can be specific for either double-stranded or single stranded polynucleotides. Cleavage can occur randomly within the polynucleotide or can cleave at specific sequences. Endonucleases which randomly cleave double strand polynucleotides often make interactions with the backbone of the polynucleotide. Specific fragmentation of polynucleotides can be accomplished using one or more enzymes is sequential reactions or contemporaneously. Homogenous or heterogenous polynucleotides can be cleaved. Cleavage can be achieved by treatment with nuclease enzymes provided from a variety of sources including the Cleavase™ enzyme, Taq DNA polymerase, *E. coli* DNA polymerase I and eukaryotic structure-specific endonucleases, murine FEN-1 endonucleases [Harrington and Liener, (1994) Genes and Develop. 8:1344] and calf thymus 5' to 3' exonuclease [Murante, R. S., et al. (1994) J. Biol. Chem. 269:1191]). In addition, enzymes having 3' nuclease activity such as members of the family of DNA repair endonucleases (e.g., the RrpI enzyme from *Drosophila melanogaster*, the yeast RAD1/RAD10 complex and *E. coli* Exo III), can also be used for enzymatic cleavage.

Restriction endonucleases are a subclass of endonucleases which recognize specific sequences within double-strand polynucleotides and typically cleave both strands either within or close to the recognition sequence. One commonly used enzyme in DNA analysis is HaeIII, which cuts DNA at the sequence 5'-GGCC-3'. Other exemplary restriction endonucleases include Acc I, Afl III, Alu I, Alw44 I, Apa I, Asn I, Ava I, Ava II, BamH I, Ban II, Bcl I, Bgl I. Bgl II, Bln I, Bsm I, BssH II, BstE II, Cfo I, Cla I, Dde I, Dpn I, Dra I, EclX I, EcoR I, EcoR I, EcoR II, EcoR V, Hae II, Hae II, Hind II, Hind III, Hpa I, Hpa II, Kpn I, Ksp I, Mlu I, MluN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I. The cleavage sites for these enzymes are known in the art.

Restriction enzymes are divided in types I, II, and III. Type I and type II enzymes carry modification and ATP-dependent cleavage in the same protein. Type III enzymes cut DNA at a recognition site and then dissociate from the DNA. Type I enzymes cleave a random sites within the DNA. Any class of restriction endonucleases can be used to fragment polynucleotides. Depending on the enzyme used, the cut in the polynucleotide can result in one strand overhanging the other also known as "sticky" ends. BamHI generates cohesive 5' overhanging ends. KpnI generates cohesive 3' overhanging ends. Alternatively, the cut can result in "blunt" ends that do not have an overhanging end. DraI cleavage generates blunt ends. Cleavage recognition sites can be masked, for example by methylation, if needed. Many of the known restriction endonucleases have 4 to 6 base-pair recognition sequences (Eckstein and Lilley (eds.), Nucleic Acids and Molecular Biology, vol. 2, Springer-Verlag, Heidelberg [1988]).

A small number of rare-cutting restriction enzymes with 8 base-pair specificities have been isolated and these are widely used in genetic mapping, but these enzymes are few in number, are limited to the recognition of G+C-rich sequences, and cleave at sites that tend to be highly clustered (Barlow and Lehrach, Trends Genet., 3:167 [1987]). Recently, endonucleases encoded by group I introns have been discovered that might have greater than 12 base-pair specificity (Perlman and Butow, Science 246:1106 [1989]).

Restriction endonucleases can be used to generate a variety of polynucleotide fragment sizes. For example, CviJ1 is a restriction endonuclease that recognizes between a two and three base DNA sequence. Complete digestion with CviJ1 can result in DNA fragments averaging from 16 to 64 nucleotides in length. Partial digestion with CviJ1 can therefore fragment DNA in a "quasi" random fashion similar to shearing or sonication. CviJ1 normally cleaves RGCY sites between the G and C leaving readily cloneable blunt ends, wherein R is any purine and Y is any pyrimidine. In the presence of 1 mM ATP and 20% dimethyl sulfoxide the specificity of cleavage is relaxed and CviJ1 also cleaves RGCN and YGCY sites. Under these "star" conditions, CviJ1 cleavage generates quasi-random digests. Digested or sheared DNA can be size selected at this point.

Methods for using restriction endonucleases to fragment polynucleotides are widely known in the art. In one exemplary protocol a reaction mixture of 20-50 μl is prepared containing: DNA 1-3 μg; restriction enzyme buffer 1×; and a restriction endonuclease 2 units for 1 μg of DNA. Suitable buffers are also known in the art and include suitable ionic strength, cofactors, and optionally, pH buffers to provide optimal conditions for enzymatic activity. Specific enzymes can require specific buffers which are generally available from commercial suppliers of the enzyme. An exemplary buffer is potassium glutamate buffer (KGB). Hannish, J. and M. McClelland. (1988). *Activity of DNA modification and restriction enzymes in KGB, a potassium glutamate buffer*. Gene Anal. Tech. 5:105; McClelland, M. et al. (1988) *A single buffer for all restriction endonucleases*. Nucleic Acid Res. 16:364. The reaction mixture is incubated at 37° C. for 1 hour or for any time period needed to produce fragments of a desired size or range of sizes. The reaction can be stopped by heating the mixture at 65° C. or 80° C. as needed. Alternatively, the reaction can be stopped by chelating divalent cations such as $Mg^{2+}$ with for example, EDTA.

More than one enzyme can be used to fragment the polynucleotide. Multiple enzymes can be used in sequential reactions or in the same reaction provided the enzymes are active under similar conditions such as ionic strength, temperature, or pH. Typically, multiple enzymes are used with a standard buffer such as KGB. The polynucleotides can be partially or completely digested. Partially digested means only a subset of the restriction sites are cleaved. Complete digestion means all of the restriction sites are cleaved.

Endonucleases can be specific for certain types of polynucleotides. For example, endonuclease can be specific for DNA or RNA. Ribonuclease H is an endoribonuclease that specifically degrades the RNA strand in an RNA-DNA hybrid. Ribonuclease A is an endoribonuclease that specifically attacks single-stranded RNA at C and U residues. Ribonuclease A catalyzes cleavage of the phosphodiester bond between the 5'-ribose of a nucleotide and the phosphate group attached to the 3'-ribose of an adjacent pyrimidine nucleotide. The resulting 2',3'-cyclic phosphate can be hydrolyzed to the corresponding 3'-nucleoside phosphate. RNase T1 digests RNA at only G ribonucleotides and RNase $U_2$ digests RNA at only A ribonucleotides. The use of mono-specific RNases such as RNase $T_1$ (G specific) and RNase $U_2$ (A specific) has become routine (Donis-Keller et al., Nucleic Acids Res. 4: 2527-2537 (1977); Gupta and Randerath, Nucleic Acids Res. 4: 1957-1978 (1977); Kuchino and Nishimura, Methods Enzymol. 180: 154-163 (1989); and Hahner et al., Nucl. Acids Res. 25(10): 1957-1964 (1997)). Another enzyme, chicken liver ribonuclease (RNase CL3) has been reported to cleave preferentially at cytidine, but the enzyme's proclivity for this base has been reported to be affected by the reaction conditions (Boguski et al., J. Biol. Chem. 255: 2160-2163 (1980)). Recent reports also claim cytidine specificity for another ribonuclease, cusativin, isolated from dry seeds of *Cucumis sativus* L (Rojo et al., Planta 194: 328-338 (1994)). Alternatively, the identification of pyrimidine residues by use of RNase PhyM (A and U specific) (Donis-Keller, H. Nucleic Acids Res. 8: 3133-3142 (1980)) and RNase A (C and U specific) (Simoncsits et al., Nature 269: 833-836 (1977); Gupta and Randerath, Nucleic Acids Res. 4: 1957-1978 (1977)) has been demonstrated. In order to reduce ambiguities in sequence determination, additional limited alkaline hydrolysis can be performed. Since every phosphodiester bond is potentially cleaved under these conditions, information about omitted and/or unspecific cleavages can be obtained this way ((Donis-Keller et al., Nucleic Acids Res. 4: 2527-2537 (1977)). Benzonase™, nuclease P1, and phosphodiesterase I are nonspecific endonucleases that are suitable for generating polynucleotide fragments ranging from 200 base pairs or less. Benzonase™ is a genetically engineered endonuclease which degrades both DNA and RNA strands in many forms and is described in U.S. Pat. No. 5,173,418 which is incorporated by reference herein.

DNA glycosylases specifically remove a certain type of nucleobase from a given DNA fragment. These enzymes can thereby produce abasic sites, which can be recognized either by another cleavage enzyme, cleaving the exposed phosphate backbone specifically at the abasic site and producing a set of nucleobase specific fragments indicative of the sequence, or by chemical means, such as alkaline solutions and or heat. The use of one combination of a DNA glycosylase and its targeted nucleotide would be sufficient to generate a base specific signature pattern of any given target region.

Numerous DNA glycosylases are known. For example, a DNA glycosylase can be uracil-DNA glycolsylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase (see, e.g., U.S. Pat. Nos. 5,536,649; 5,888,795; 5,952,176; 6,099,553; and 6,190,865 B1; International PCT application Nos. WO 97/03210, WO 99/54501; see, also, Eftedal et al. (1993) Nucleic Acids Res 21:2095-2101, Bjelland and Seeberg (1987) Nucleic Acids Res. 15:2787-2801, Saparbaev et al. (1995) Nucleic Acids Res. 23:3750-3755, Bessho (1999) Nucleic Acids Res. 27:979-983) corresponding to the enzyme's modified nucleotide or nucleotide analog target.

Uracil, for example, can be incorporated into an amplified DNA molecule by amplifying the DNA in the presence of normal DNA precursor nucleotides (e.g. dCTP, dATP, and dGTP) and dUTP. When the amplified product is treated with UDG, uracil residues are cleaved. Subsequent chemical treatment of the products from the UDG reaction results in the cleavage of the phosphate backbone and the generation of nucleobase specific fragments. Moreover, the separation of the complementary strands of the amplified product prior to glycosylase treatment allows complementary patterns of fragmentation to be generated. Thus, the use of dUTP and Uracil DNA glycosylase allows the generation of T specific fragments for the complementary strands, thus providing information on the T as well as the A positions within a given sequence. A C-specific reaction on both. (complementary) strands (i.e., with a C-specific glycosylase) yields information on C as well as G positions within a given sequence if the fragmentation patterns of both amplification strands are analyzed separately. With the glycosylase method and mass spectrometry, a full series of A, C, G and T specific fragmentation patterns can be analyzed.

Several methods exist where treatment of DNA with specific chemicals modifies existing bases so that they are recognized by specific DNA glycosylases. For example, treatment of DNA with alkylating agents such as methylnitrosourea generates several alkylated bases including N3-methyladenine and N3-methylguanine which are recognized and cleaved by alkyl purine DNA-glycosylase. Treatment of DNA with sodium bisulfite causes deamination of cytosine residues in DNA to form uracil residues in the DNA which can be cleaved by uracil N-glycosylase (also known as uracil DNA-glycosylase). Chemical reagents can also convert guanine to its oxidized form, 8-hydroxyguanine, which can be cleaved by formamidopyrimidine DNA N-glycosylase (FPG protein) (Chung et al., "An endonuclease activity of *Escherichia coli* that specifically removes 8-hydroxyguanine residues from DNA," Mutation Research 254: 1-12 (1991)). The use of mismatched nucleotide glycosylases have been reported for cleaving polynucleotides at mismatched nucleotide sites for the detection of point mutations (Lu, A-L and Hsu, I-C, Genomics (1992) 14, 249-255 and Hsu, I-C., et al, Carcinogenesis (1994)14, 1657-1662). The glycosylases used include the *E. coli* Mut Y gene product which releases the mispaired adenines of A/G mismatches efficiently, and releases A/C mismatches albeit less efficiently, and human thymidine DNA glycosylase which cleaves at Gfr mismatches. Fragments are produced by glycosylase treatment and subsequent cleavage of the abasic site.

Fragmentation of nucleic acids for the methods as provided herein can also be accomplished by dinucleotide ("2 cutter") or relaxed dinucleotide ("1 and ½ cutter", e.g.) cleavage specificity. Dinucleotide-specific cleavage reagents are known to those of skill in the art and are incorporated by reference herein (see, e.g., WO 94/21663; Cannistraro et al., *Eur. J. Biochem.*, 181:363-370, 1989; Stevens et al., *J. Bacteriol.*, 164:57-62, 1985; Marotta et al., *Biochemistry*, 12:2901-2904, 1973). Stringent or relaxed dinucleotide-specific cleavage can also be engineered through the enzymatic and chemical modification of the target nucleic acid. For example, transcripts of the target nucleic acid of interest can be synthesized with a mixture of regular and α-thio-substrates and the phosphorothioate internucleoside linkages can subsequently be modified by alkylation using reagents such as an alkyl halide (e.g., iodoacetamide, iodoethanol) or 2,3-epoxy-1-propanol. The phosphotriester bonds formed by such modification are not expected to be substrates for RNAses. Using this procedure, a mono-specific RNAse, such as RNAse-T1, can be made to cleave any three, two or one out of the four possible GpN bonds depending on which substrates are used in the α-thio form for target preparation. The repertoire of useful dinucleotide-specific cleavage reagents can be further expanded by using additional RNAses, such as RNAse-U2 and RNAse-A. In the case of RNAse A, for example, the cleavage specificity can be restricted to CpN or UpN dinucleotides through enzymatic incorporation of the 2'-modified form of appropriate nucleotides, depending on the desired cleavage specificity. Thus, to make RNAse A specific for CpG nucleotides, a transcript (target molecule) is prepared by incorporating αS-dUTP, αS-ATP, αS-CTP and GTP nucleotides. These selective modification strategies can also be used to prevent cleavage at every base of a homopolymer tract by selectively modifying some of the nucleotides within the homopolymer tract to render the modified nucleotides less resistant or more resistant to cleavage.

DNAses can also be used to generate polynucleotide fragments. Anderson, S. (1981) *Shotgun DNA sequencing using cloned DNase I-generated fragments*. Nucleic Acids Res. 9:3015-3027. DNase I (Deoxyribonuclease I) is an endonuclease that digests double- and single-stranded DNA into poly- and mono-nucleotides. The enzyme is able to act upon single as well as double-stranded DNA and on chromatin.

Deoxyribonuclease type II is used for many applications in nucleic acid research including DNA sequencing and digestion at an acidic pH. Deoxyribonuclease II from porcine spleen has a molecular weight of 38,000 daltons. The enzyme is a glycoprotein endonuclease with dimeric structure. Optimum pH range is 4.5-5.0 at ionic strength 0.15 M. Deoxyribonuclease II hydrolyzes deoxyribonucleotide linkages in native and denatured DNA yielding products with 3'-phosphates. It also acts on p-nitrophenylphosphodiesters at pH 5.6-5.9. Ehrlich, S. D. et al. (1971) *Studies on acid deoxyribonuclease. IX. 5'-Hydroxy-terminal and penultimate nucleotides of oligonucleotides obtained from calf thymus deoxyribonucleic acid*. Biochemistry. 10(11):2000-9.

Large single stranded polynucleotides can be fragmented into small polynucleotides using nuclease that remove various lengths of bases from the end of a polynuculeotide. Exemplary nucleases for removing the ends of single stranded polynucleotides include but are not limited to S1, Bal 31, and mung bean nucleases. For example, mung bean nuclease degrades single stranded DNA to mono or poly-nucleotides with phosphate groups at their 5' termini. Double stranded nucleic acids can be digested completely if exposed to very large amounts of this enzyme.

Exonucleases are proteins that also cleave nucleotides from the ends of a polynucleotide, for example a DNA molecule. There are 5' exonucleases (cleave the DNA from the 5'-end of the DNA chain) and 3' exonucleases (cleave the DNA from the 3'-end of the chain). Different exonucleases can hydrolyse single-strand or double strand DNA. For example, Exonuclease III is a 3' to 5' exonuclease, releasing 5'-mononucleotides from the 3'-ends of DNA strands; it is a DNA 3'-phosphatase, hydrolyzing 3'-terminal phosphomonoesters; and it is an AP endonuclease, cleaving phosphodiester bonds at apurinic or apyrimidinic sites to produce 5'-termini that are base-free deoxyribose 5'-phosphate residues. In addition, the enzyme has an RNase H activity; it will preferentially degrade the RNA strand in a DNA-RNA hybrid duplex, presumably exonucleolytically. In mammalian cells, the major DNA 3'-exonuclease is DNase III (also called TREX-1). Thus, fragments can be formed by using exonucleases to degrade the ends of polynucleotides.

Catalytic DNA and RNA are known in the art and can be used to cleave polynucleotides to produce polynucleotide fragments. Santoro, S. W. and Joyce, G. F. (1997) *A general purpose RNA-cleaving DNA enzyme*. Proc. Natl. Acad. Sci. USA 94: 4262-4266. DNA as a single-stranded molecule can fold into three dimensional structures similar to RNA, and the 2'-hydroxy group is dispensable for catalytic action. As ribozymes, DNAzymes can also be made, by selection, to depend on a cofactor. This has been demonstrated for a histidine-dependent DNAzyme for RNA hydrolysis. U.S. Pat. Nos. 6,326,174 and 6,194,180 disclose deoxyribonucleic acid enzymes—catalytic or enzymatic DNA molecules—capable of cleaving nucleic acid sequences or molecules, particularly RNA. U.S. Pat. Nos. 6,265,167; 6,096,715; 5,646, 020 disclose ribozyme compositions and methods and are incorporated herein by reference.

A DNA nickase, or DNase, can be used to recognize and cleave one strand of a DNA duplex. Numerous nickases are known. Among these, for example, are nickase NY2A nickase and NYS1 nickase (Megabase) with the following cleavage sites:

```
NY2A:  5'. . . R AG . . . 3'
       3'. . . Y TC . . . 5' where R = A or G and
                                   Y = C or T
NYS1:  5'. . . CC[A/G/T]. . . 3'
       3'. . . GG[T/C/A]. . . 5'.
```

Subsequent chemical treatment of the products from the nickase reaction results in the cleavage of the phosphate backbone and the generation of fragments.

The Fen-1 fragmentation method involves the enzymes Fen-1 enzyme, which is a site-specific nuclease known as a "flap" endonuclease (U.S. Pat. Nos. 5,843,669, 5,874,283, and 6,090,606). This enzyme recognizes and cleaves DNA "flaps" created by the overlap of two oligonucleotides hybridized to a target DNA strand. This cleavage is highly specific and can recognize single base pair mutations, permitting detection of a single homologue from an individual heterozygous at one SNP of interest and then genotyping that homologue at other SNPs occurring within the fragment. Fen-1 enzymes can be Fen-1 like nucleases e.g. human, murine, and Xenopus XPG enzymes and yeast RAD2 nucleases or Fen-1 endonucleases from, for example, *M. jannaschii, P. furiosus*, and *P. woesei*.

Another technique, which is under development as a diagnostic tool for detecting the presence of *M. tuberculosis*, can be used to cleave DNA chimeras. Tripartite DNA-RNA-DNA probes are hybridized to target nucleic acids, such as *M. tuberculosis*-specific sequences. Upon the addition of RNAse H, the RNA portion of the chimeric probe is degraded, releasing the DNA portions [Yule, Bio/Technology 12:1335 (1994)].

Fragments can also be formed using any combination of fragmentation methods as well as any combination of enzymes. Methods for producing specific fragments can be combined with methods for producing random fragments. Additionally, one or more enzymes that cleave a polynucleotide at a specific site can be used in combination with one or more enzymes that specifically cleave the polynucleotide at a different site. In another example, enzymes that cleave specific kinds of polynucleotides can be used in combination, for example, an RNase in combination with a DNase. In still another example, an enzyme that cleaves polynucleotides randomly can be used in combination with an enzyme that cleaves polynucleotides specifically. Used in combination means performing one or more methods after another or contemporaneously on a polynucleotide.

Peptide Fragmentation

As interest in proteomics has increased as a field of study, a number of techniques have been developed for protein fragmentation for use in protein sequencing. Among these are chemical and enzymatic hydrolysis, and fragmentation by ionization energy.

Sequential cleavage of the N-terminus of proteins is well known in the art, and can be accomplished using Edman degradation. In this process, the N-terminal amino acid is reacted with phenylisothiocyanate to a PTC-protein with an intermediate anilinothiazolinone forming when contacted with trifluoroacetic acid. The intermediate is cleaved and converted to the phenylthiohydantoin form and subsequently separated, and identified by comparison to a standard. To facilitate protein cleavage, proteins can be reduced and alkylated with vinylpyridine or iodoacetamide.

Chemical cleavage of proteins using cyanogen bromide is well known in the art (Nikodem and Fresco, Anal. Biochem. 97: 382-386 (1979); Jahnen et al., Biochem. Biophys. Res. Commun. 166: 139-145 (1990)). Cyanogen bromide (CNBr) is one of the best methods for initial cleavage of proteins. CNBr cleaves proteins at the C-terminus of methionyl residues. Because the number of methionyl residues in proteins is usually low, CNBr usually generates a few large fragments. The reaction is usually performed in a 70% formic acid or 50% trifluoroacetic acid with a 50- to 100-fold molar excess of cyanogen bromide to methionine. Cleavage is usually quantitative in 10-12 hours, although the reaction is usually allowed to proceed for 24 hours. Some Met-Thr bonds are not cleaved, and cleavage can be prevented by oxidation of methionines.

Proteins can also be cleaved using partial acid hydrolysis methods to remove single terminal amino acids (Vanfleteren et al., BioTechniques 12: 550-557 (1992). Peptide bonds containing aspartate residues are particularly susceptible to acid cleavage on either side of the aspartate residue, although usually quite harsh conditions are needed. Hydrolysis is usually performed in concentrated or constant boiling hydrochloric acid in sealed tubes at elevated temperatures for various time intervals from 2 to 18 hours. Asp-Pro bonds can be cleaved by 88% formic acid at 37°. Asp-Pro bonds have been found to be susceptible under conditions where other Asp-containing bonds are quite stable. Suitable conditions are the incubation of protein (at about 5 mg/ml) in 10% acetic acid, adjusted to pH 2.5 with pyridine, for 2 to 5 days at 40° C.

Brominating reagents in acidic media have been used to cleave polypeptide chains. Reagents such as N-bromosuccinimide will cleave polypeptides at a variety of sites, including tryptophan, tyrosine, and histidine, but often give side reactions which lead to insoluble products. BNPS-skatole [2-(2-nitrophenylsulfenyl)-3-methylindole] is a mild oxidant and brominating reagent that leads to polypeptide cleavage on the C-terminal side of tryptophan residues.

Although reaction with tyrosine and histidine can occur, these side reactions can be considerably reduced by including tyrosine in the reaction mix. Typically, protein at about 10 mg/ml is dissolved in 75% acetic acid and a mixture of BNPS-skatole and tyrosine (to give 100-fold excess over tryptophan and protein tyrosine, respectively) is added and incubated for 18 hours. The peptide-containing supernatant is obtained by centrifugation.

Apart from the problem of mild acid cleavage of Asp-Pro bonds, which is also encountered under the conditions of BNPS-skatole treatment, the only other potential problem is the fact that any methionine residues are converted to methioninesulfoxide, which cannot then be cleaved by cyanogen bromide. If CNBr cleavage of peptides obtained from BNPS-skatole cleavage is necessary, the methionine residues can be regenerated by incubation with 15% mercaptoethanol at 30° C. for 72 hours.

Treating proteins with o-Iodosobenzoic acid cleaves tryptophan-X bonds under quite mild conditions. Protein, in 80% acetic acid containing 4 M guanidine hydrochloride, is incubated with iodobenzoic acid (approximately 2 mg/ml of protein) that has been preincubated with p-cresol for 24 hours in the dark at room temperature. The reaction can be terminated by the addition of dithioerythritol. Care must be taken to use purified o-iodosobenzoic acid since a contaminant, o-iodoxybenzoic acid, will cause cleavage at tyrosine-X bonds and possibly histidine-X bonds. The function of p-cresol in the reaction mix is to act as a scavenging agent for residual o-iodoxybenzoic acid and to improve the selectivity of cleavage.

Two reagents are available that produce cleavage of peptides containing cysteine residues. These reagents are (2-methyl) N-1-benzenesulfonyl-N-4-(bromoacetyl)quinone diimide (otherwise known as Cyssor, for "cysteine-specific scission by organic reagent") and 2-nitro-5-thiocyanobenzoic acid (NTCB). In both cases cleavage occurs on the amino-terminal side of the cysteine.

Incubation of proteins with hydroxylamine results in the fragmentation of the polypeptide backbone (Saris et al., Anal. Biochem. 132: 54-67 (1983). Hydroxylaminolysis leads to cleavage of any asparaginyl-glycine bonds. The reaction occurs by incubating protein, at a concentration of about 4 to 5 mg/ml, in 6 M guanidine hydrochloride, 20 mM sodium acetate+1% mercaptoethanol at pH 5.4, and adding an equal volume of 2 M hydroxylamine in 6 M guanidine hydrochloride at pH 9.0. The pH of the resultant reaction mixture is kept at 9.0 by the addition of 0.1 N NaOH and the reaction allowed to proceed at 45° C. for various time intervals; it can be terminated by the addition of 0.1 volume of acetic acid. In the absence of hydroxylamine, a base-catalyzed rearrangement of the cyclic imide intermediate can take place, giving a mixture of α-aspartylglycine and β-aspartylglycine without peptide cleavage.

There are many methods known in the art for hydrolysing protein by use of a proteolytic enzymes (Cleveland et al., J. Biol. Chem. 252: 1102-1106 (1977). All peptidases or proteases are hydrolases which act on protein or its partial hydrolysate to decompose the peptide bond. Native proteins are poor substrates for proteases and are usually denatured by treatment with urea prior to enzymatic cleavage. The prior art discloses a large number of enzymes exhibiting peptidase, aminopeptidase and other enzyme activities, and the enzymes can be derived from a number of organisms, including vertebrates, bacteria, fungi, plants, retroviruses and some plant viruses. Proteases have been useful, for example, in the isolation of recombinant proteins. See, for example, U.S. Pat. Nos. 5,387,518, 5,391,490 and 5,427,927, which describe various proteases and their use in the isolation of desired components from fusion proteins.

The proteases can be divided into two categories. Exopeptidases, which include carboxypeptidases and aminopeptidases, remove one or more amino terminal residues from polypeptides. Endopeptidases, which cleave within the polypeptide sequence, cleave between specific residues in the protein sequence. The various enzymes exhibit differing requirements for optimum activity, including ionic strength, temperature, time and pH. There are neutral endoproteases (such as Neutrase™) and alkline endoproteases (such as Alcalase™ and Esperase™), as well as acid-resistant carboxypeptidases (such as carboxypeptidase-P).

There has been extensive investigation of proteases to improve their activity and to extend their substrate specificity (for example, see U.S. Pat. Nos. 5,427,927; 5,252,478; and 6,331,427 B1). One method for extending the targets of the proteases has been to insert into the target protein the cleavage sequence that is required by the protease. Recently, a method has been disclosed for making and selecting site-specific proteases ("designer proteases") able to cleave a user-defined recognition sequence in a protein (see U.S. Pat. No. 6,383, 775).

The different endopeptidase enzymes cleave proteins at a diverse selection of cleavage sites. For example, the endopeptidase renin cleaves between the leucine residues in the following sequence: Pro-Phe-His-Leu-Leu-Val-Tyr (SEQ ID NO:1) (Haffey, M. L. et al., DNA 6:565 (1987). Factor Xa protease cleaves after the Arg in the following sequences: Ile-Glu-Gly-Arg-X; Ile-Asp-Gly-Arg-X; and Ala-Glu-Gly-Arg-X, where X is any amino acid except proline or arginine, (SEQ ID NOS:2-4, respectively) (Nagai, K. and Thogersen, H. C., Nature 309:810 (1984); Smith, D. B. and Johnson, K. S. Gene 67:31 (1988)). Collagenase cleaves following the X and Y residues in following sequence: -Pro-X-Gly-Pro-Y- (where X and Y are any amino acid) (SEQ ID NO:5) (Germino J. and Bastis, D., Proc. Natl. Acad. Sci. USA 81:4692 (1984)). Glutamic acid endopeptidase from S. aureus V8 is a serine protease specific for the cleavage of peptide bonds at the carboxy side of aspartic acid under acid conditions or glutamic acid alkaline conditions.

Trypsin specifically cleaves on the carboxy side of arginine, lysine, and S-aminoethyl-cysteine residues, but there is little or no cleavage at arginyl-proline or lysyl-proline bonds. Pepsin cleaves preferentially C-terminal to phenylalanine, leucine, and glutamic acid, but it does not cleave at valine, alanine, or glycine. Chymotrypsin cleaves on the C-terminal side of phenylalanine, tyrosine, tryptophan, and leucine. Aminopeptidase P is the enzyme responsible for the release of any N-terminal amino acid adjacent to a proline residue. Proline dipeptidase (prolidase) splits dipeptides with a prolyl residue in the carboxyl terminal position.

Ionization Fragmentation Cleavage of Peptides or Nucleic Acids

Ionization fragmentation of proteins or nucleic acids is accomplished during mass spectrometric analysis either by using higher voltages in the ionization zone of the mass spectrometer (MS) to fragment by tandem MS using collision-induced dissociation in the ion trap. (see, e.g., Bieman, Methods in Enzymology, 193:455-479 (1990)). The amino acid or base sequence is deduced from the molecular weight differences observed in the resulting MS fragmentation pattern of the peptide or nucleic acid using the published masses associated with individual amino acid residues or nucleotide residues in the MS.

Complete sequencing of a protein is accomplished by cleavage of the peptide at almost every residue along the peptide backbone. When a basic residue is located at the N-terminus and/or C-terminus, most of the ions produced in the collision induced dissociation (CID) spectrum will contain that residue (see, Zaia, J., in: Protein and Peptide Analysis by Mass Spectrometry, J. R. Chapman, ed., pp. 29-41, Humana Press, Totowa, N.J., 1996; and Johnson, R. S., et al., Mass Spectrom. Ion Processes, 86:137-154 (1988)) since positive charge is generally localized at the basic site. The presence of a basic residue typically simplifies the resulting spectrum, since a basic site directs the fragmentation into a limited series of specific daughter ions. Peptides that lack basic residues tend to fragment into a more complex mixture of fragment ions that makes sequence determination more difficult. This can be overcome by attaching a hard positive charge to the N-terminus. See, Johnson, R. S., et al., Mass Spectrom. Ion Processes, 86:137-154 (1988); Vath, J. E., et al., Fresnius Z Anal. Chem., 331:248-252 (1988); Stults, J. T., et al., Anal. Chem., 65:1703-1708 (1993); Zaia, J., et al., J Am. Soc. Mass Spectrom., 6:423-436 (1995); Wagner, D. S., et al., Biol. Mass Spectrom., 20:419-425 (1991); and Huang, Z.-H., et al., Anal. Biochem., 268:305-317 (1999). The proteins can also be chemically modified to include a label which modifies its molecular weight, thereby allowing differentiation of the mass fragments produced by ionization fragmentation. The labeling of proteins with various agents is known in the art and a wide range of labeling reagents and techniques useful in practicing the methods herein are readily available to those of skill in the art. See, for example, Means et al., Chemical Modification of Proteins, Holden-Day, San Francisco, 1971; Feeney et al., Modification of Proteins: Food, Nutritional and Pharmacological Aspects, Advances in Chemistry Series, Vol. 198, American Chemical Society, Washington, D.C., 1982).

The methods described herein can be used to analyze target nucleic acid or peptide fragments obtained by specific cleavage as provided above for various purposes including, but not limited to, polymorphism detection, SNP scanning, bacteria and viral typing, pathogen detection, antibiotic profiling, organism identification, identification of disease markers, methylation analysis, microsatellite analysis, haplotyping, genotyping, determination of allelic frequency, multiplexing, and nucleotide sequencing and re-sequencing.

C. TECHNIQUES FOR POLYMORPHISM, MUTATION AND SEQUENCE VARIATION DISCOVERY

Provided herein are techniques that increase the speed with which mutations, polymorphisms or other sequence variations can be detected in a target sequence, relative to a reference sequence. Previous methods of discovering known or unknown sequence variations in a target sequence relative to a reference sequence involved simulating, for every possible target sequence variation of the reference sequence (including substitutions, insertions, deletions, polymorphisms and species-dependent variations), a specific fragmentation spectrum that would be generated by a given cleavage reagent or set of cleavage reagents for that particular target sequence. In such previous methods, each of the simulations generated by all possible sequence variations in the target sequence relative to the reference sequence were then compared against the actual fragmentation spectrum obtained for the target sequence, to determine the actual sequence variation that is present in the target sequence. The problem with such an approach is that the time and resources expended to generate simulations of all possible sequence variation candidates can be prohibitive.

One way to address this problem is to reduce the number of possible sequence variations of a given target sequence whose fragmentation patterns are simulated and compared against the actual fragmentation pattern generated by cleavage of the target sequence. In the methods provided herein, an algorithm is used to output only those sequence variation candidates that are most likely to have generated the actual fragmentation spectrum of the target sequence. A second algorithm then simulates only this subset of sequence variation candidates for comparison against the actual target sequence fragmentation spectrum. Thus, the number of sequence variations for simulation analyses is drastically reduced.

In the methods provided herein, in a first step, the fragments corresponding to difference in signals between a target sequence and a reference sequence that are absolute (presence or absence of a signal in the target spectrum relative to a reference spectrum) or quantitative (differences in signal intensities or signal to noise ratios) differences obtained by actual cleavage of the target sequence relative to actual or simulated cleavage of the reference sequence under the same conditions are identified, and the masses of these "different" target nucleic acid fragments are determined. Once the masses of the different fragments are determined, one or more nucleic acid base compositions (compomers) are identified whose masses differ from the actual measured mass of each different fragment by a value that is less than or equal to a sufficiently small mass difference. These compomers are called witness compomers. The value of the sufficiently small mass difference is determined by parameters such as the peak separation between fragments whose masses differ by a single nucleotide equivalent in type or length, and the absolute resolution of the mass spectrometer. Cleavage reactions specific for one or more of the four nucleic acid bases (A, G, C, T or U for RNA, or modifications thereof, or amino acids or modifications thereof for proteins) can be used to generate data sets comprising the possible witness compomers for each specifically cleaved fragment that nears or equals the measured mass of each different fragment by a value that is less than or equal to a sufficiently small mass difference.

The techniques provided herein can reconstruct the target sequence variations from possible witness compomers corresponding to differences between the fragments of the target nucleic acid relative to the reference nucleic acid.

Algorithm 1: Find Sequence Variation Candidates

This is the basic technique that is used to analyze the results from one or more specific cleavage reactions of a target nucleic acid sequence. The first step identifies all possible compomers whose masses differ by a value that is less than or equal to a sufficiently small mass difference from the actual mass of each different fragment generated in the target nucleic acid cleavage reaction relative to the same reference nucleic acid cleavage reaction. These compomers are the 'compomer witnesses'. For example, suppose a different fragment peak is detected at 2501.3 Da. The only natural compomer having a mass within, e.g., a +/−2 Da interval of the peak mass is $A_1C_4G_2T_1$ at 2502.6 Da. In the case of cleavage reactions that do not remove the recognized base (herein, T) at the cleavage site, (for example, UDG will remove the cleaved base, but RNAse A will not) the recognition base is subtracted, resulting in the compomer $A_1C_4G_2$. Every compomer detected in this fashion is called a compomer witness.

The basic technique then determines all compomers that can be transformed into each compomer witness c' with at most k mutations, polymorphisms, or other sequence variations including, but not limited to, sequence variations between organisms. The value of k, the sequence variation order, is predefined by the user and is dependent on a number of parameters including, but not limited to, the expected type and number of sequence variations between a reference sequence and the target sequence, e.g., whether the sequence variation is a single base or multiple bases, whether sequence variations are present at one location or at more than one location on the target sequence relative to the reference sequence, or whether the sequence variations interact or do not interact with each in the target sequence. For example, for the detection of SNPs, the value of k is usually, although not necessarily, 1 or 2. As another example, for the detection of mutations and in resequencing, the value of k is usually, although not necessarily, 3 or higher.

A set of bounded compomers are constructed, which refers to the set of all compomers c that correspond to the set of subsequences of a reference sequence, with a boundary b that indicates whether or not cleavage sites are present at the two ends of each subsequence. The set of bounded compomers can be compared against possible compomer witnesses to construct all possible sequence variations of a target sequence relative to a reference sequence. Using the constructed pairs of compomer witnesses and bounded compomers, the algorithm then constructs all sequence variation candidates that would lead to the obtained differences in the fragmentation pattern of a target sequence relative to a reference sequence under the same cleavage conditions.

The determination of sequence variation candidates significantly reduces the sample set of sequence variations that are analyzed to determine the actual sequence variations in the target sequence, relative to the previous approach of simulating the fragmentation pattern of every possible sequence that is a variation of a reference sequence, and comparing the simulated patterns with the actual fragmentation pattern of the target nucleic acid sequence.

Two functions $d_+$, $d_-$ are defined as:

$$d_+(c) := \Sigma_{b \text{ in } \{A,C,G,T\}} c(b) \text{ for those } b \text{ with } c(b) > 0$$

$$d_-(c) := \Sigma_{b \text{ in } \{A,C,G,T\}} c(b) \text{ for those } b \text{ with } c(b) < 0$$

and a function d(c) is defined as $d(c) := \max\{d_+(c), d_-(c)\}$ and $d(c,c') := d(c-c')$. This is a metric function that provides a lower bound for the number of insertions, deletions, substitutions and other sequence variations that are needed to mutate one fragment, e.g., a reference fragment into another, e.g., a target fragment. If f,f' are fragments and c,c' are the corresponding compomers, then we need at least d(c,c') sequence variations to transform f into f'.

A substring (fragment) of the string s (full length sequence) is denoted s[i,j], where i,j are the start and end positions of the substring satisfying $1 \leq i \leq j \leq$ length of s.

A compomer boundary or boundary is a subset of the set {L,R}. Possible values for b are { } (the empty set), {L}, {R}, {L,R}. For a boundary b, #b denotes the number of elements in b, that is, 0, 1, or 2. A bounded compomer (c,b) contains a compomer c and a boundary b. Bounded compomers refers to the set of all compomers c that correspond to the set of subsequences of a reference sequence, with a boundary that indicates whether or not cleavage sites are present at the two ends of each subsequence. The set of bounded compomers can be compared against possible compomer witnesses to construct all possible sequence variations of a target sequence relative to a reference sequence.

The distance between a compomer c' and a bounded compomer (c,b) is defined as:

$$D(c',c,b) := d(c',c) + \#b$$

The function D(c',c,b) measures the minimum number of sequence variations relative to a reference sequence that is needed to generate the compomer witness c'.

Given a specific cleavage reaction of a base, amino acid, or other feature X recognized by the cleavage reagent in a string s, then the boundary b[i,j] of the substring s[i,j] or the corresponding compomer c[i,j] refers to a set of markers indicating whether cleavage of string s does not take place immediately outside the substring s[i,j]. Possible markers are L, indicating whether "s is not cleaved directly before i", and R, indicating whether "s is not cleaved directly after j". Thus, b[i,j] is a subset of the set {L,R} that contains L if and only if X is present at position i−1 of the string s, and contains R if and only if X is present at position j+1 of the string s. #b denotes the number of elements in the set b, which can be 0, 1, or 2, depending on whether the substring s[i,j] is specifically cleaved at both immediately flanking positions (i.e., at positions i−1 and j+1), at one immediately flanking position (i.e., at either position i−1 or j+1) or at no immediately flanking position (i.e., at neither position i−1 nor j+1). b[i,j] is a subset of the set {L,R} and denotes the boundary of s[i,j] as defined by the following:

b[i,j] := {L,R} if s is neither cleaved directly before i nor after j b[i,j] := {R} if s is cleaved directly before i, but not after j b[i,j] := {L} if s is cleaved directly after j, but not before i b[i,j] := { } if s is cleaved directly before i and after j b[i,j] denotes the number of elements of the set b[i,j].

The set of all bounded compomers of s is defined as:

C := {(c[i,j], b[i,j]) : $1 \leq i \leq j \leq$ length of s}, where the compomer corresponding to the substring s[i,j] of s is denoted c[i,j].

If there is a sequence variation of a target sequence containing at most k mutations, polymorphisms, or other sequence variations, including, but not limited to, sequence variations between organisms, insertions, deletions and substitutions (usually, for a nucleic acid, k would represent the number of single base variations in a sequence variation), and if c' is a compomer witness of this sequence variation, then there exists a bounded compomer (c,b) in C such that $D(c',c,b) \leq k$. In other words, of every sequence variation of a target sequence containing at most k mutations, polymorphisms, or other sequence variations, including, but not limited to, sequence variations between organisms, insertions, deletions and substitutions (usually, for a nucleic acid, k would represent the number of single base variations in a sequence variation) that leads to a different fragment corresponding to a signal that is different in the target sequence relative to the reference sequence and that corresponds to a compomer witness c', there is a bounded compomer (c,b) in C with the property $D(c',c,b) \leq k$. Thus, the number of fragments under consideration can be reduced to just those which contain at most k cleavage points:

$C_k := \{(c[i,j], b[i,j]) : 1 \leq i \leq j \leq$ length of s, and ord$[i,j]+\#b[i,j] \leq k\}$, where ord[i,j] is the number of times the fragment s[i,j] will be cleaved.

Algorithm 1

Find Sequence Variation Candidates

INPUT: Reference sequence s (or more than one reference sequence), description of cleavage reaction, whether modified nucleotides or amino acids are incorporated into all or part of the sequence, list of peaks corresponding to different fragments (either missing signals or additional signals or qualitative differences in the target sequence relative to the reference sequence(s)), maximal sequence variation order k.

OUTPUT: List of sequence variations that contain at most k insertions, deletions, and substitutions, and that have a different peak as a witness.

Given the reference sequence s and the specific cleavage reaction, compute all bounded compomers (c[i,j],b[i,j]) in $C_k$, and store them together with the indices i,j. This is usually independent of the samples containing target sequences being analyzed, and is usually done once.

For every different peak, find all compomers with mass close to the peak mass by a sufficiently small mass difference, and store them as compomer witnesses.

For every compomer witness c', find all bounded compomers (c,b) in $C_k$ such that D(c',c,b)≦k.

For every such bounded compomer (c,b) with indices i,j compute all sequence variations of s to a new reference sequence s' using at most k insertions, deletions, and substitutions such that:

if L in b, then we insert/substitute to a cleaved base or amino acid directly before position i;

if R in b, then we insert/substitute to a cleaved base or amino acid directly after position j;

Use at most k-#b insertions, deletions, and insertions that transform the fragment f=s[i,j] with corresponding compomer c into some fragment f' of s' with corresponding compomer c'.

Output every such sequence variation.

FIG. 1 is a flow diagram that illustrates operations performed with a computer system that is engaged in data analysis to determine those sequence variation candidates that satisfy the criteria described above. In the first operation, indicated by box 102, the target molecule is cleaved into fragments using one or more cleavage reagents, using techniques that are well-known to those of skill in the art and described herein. In the next operation, represented by box 104, the reference molecule is actually or virtually (by simulation) cleaved into fragments using the same one or more cleavage reagents. From the fragments produced by the cleavage reactions, data, such as mass spectra for the target and reference sequences, are produced. The produced data can be used to extract a list of peaks of the sequence data corresponding to fragments that represent differences between the target sequence and the reference sequence.

The next operation is to determine a reduced set of sequence variation candidates based on the identified different fragments. This operation is depicted by box 106. The sequence variation candidates are then scored (box 108), and the sequence variation candidates corresponding to the actual sequence variations in the target sequence are identified based on the value of the score. Usually, in a set of samples of target sequences, the highest score represents the most likely sequence variation in the target molecule, but other rules for selection can also be used, such as detecting a positive score, when a single target sequence is present.

In an exemplary embodiment described herein, the data produced from cleavage reactions comprises the output of conventional laboratory equipment for the analysis of molecular information. Such output is readily available in a variety of digital data formats, such as plain text or according to word processing formats or according to proprietary computer data representations.

Figure 2:
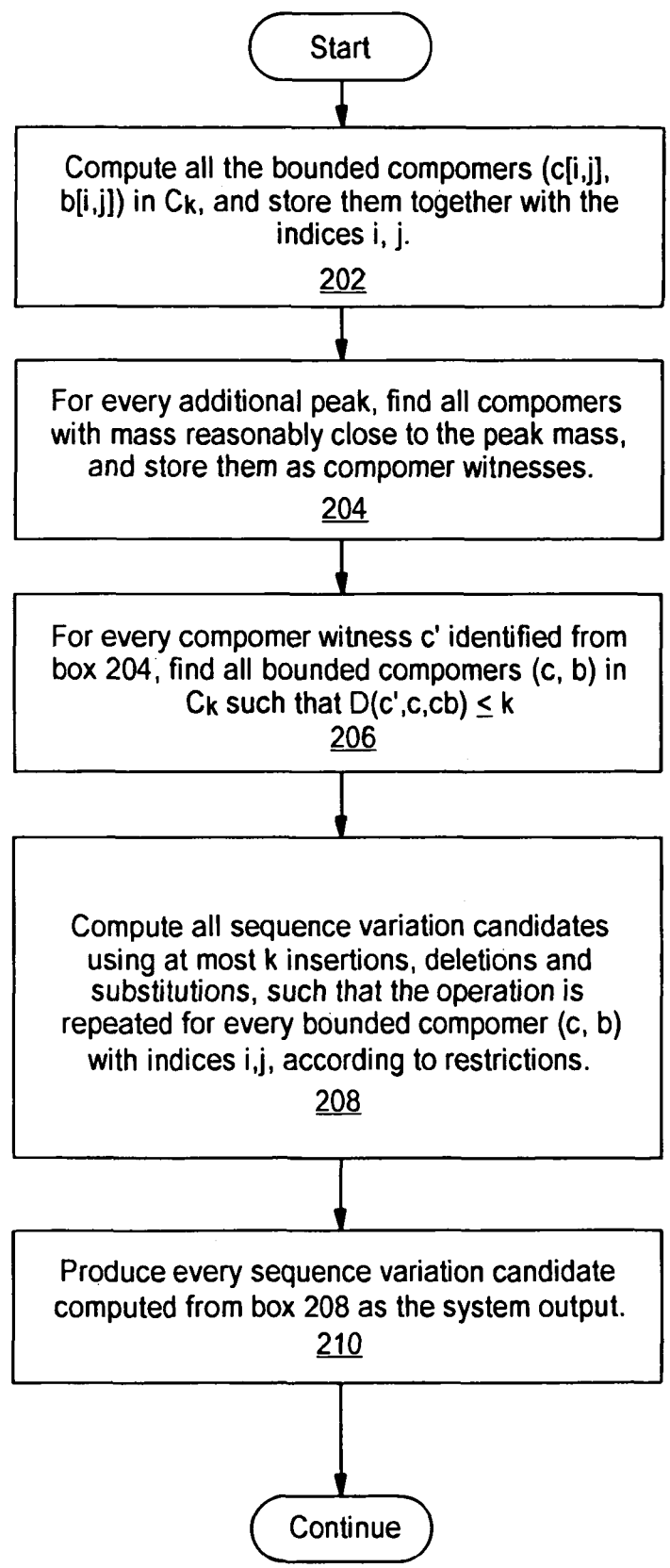
FIG. 2 is a flow diagram that illustrates operations executed by a computer system to determine a reduced set of sequence variation candidates.

As described above, the process of determining a reduced set of sequence variation candidates based on the identified different fragments is preferably carried out with a programmed computer. FIG. 2 is a flow diagram that illustrates the operations executed by a computer system to determine the reduced set of sequence variation candidates.

In the first operation, represented by box 202, the reaction data described above is processed to compute all bounded compomers (c[i,j],b[i,j]) in $C_k$, and stored together with the indices i,j, in accordance with the reference sequence s and the specific cleavage reaction data described above. The next operation, indicated by box 204, is to find, for every different peak, all compomers with mass that differs from the peak mass by a sufficiently small mass difference that is reasonably close to the peak mass. The value of the sufficiently small mass difference is determined by parameters that include, but are not limited to, the peak separation between fragments whose masses differ by a single nucleotide in type or length, and the absolute resolution of the mass spectrometer. These compomers are stored as compomer witnesses. After the compomer witnesses are identified, the next operation is to find, for every compomer witness c' identified from box 204, all bounded compomers (c,b) in $C_k$ such that D(c',c,b)≦k. The bounded compomer operation is represented by box 206. Box 208 represents the operation that involves the computation of all sequence variations of s to a new reference sequence s' using at most k insertions, deletions, and substitutions such that:

if L in b, then we insert/substitute to a cleaved base or amino acid directly before position i;

if R in b, then we insert/substitute to a cleaved base or amino acid directly after position j;

Use at most k-#b insertions, deletions, and insertions that transform the fragment f=s[i,j] with corresponding compomer c into some fragment f' of s' with corresponding compomer c'.

The last operation, indicated by box 210, is to produce every such sequence variation computed from box 208 as the system output. Here, d(c,c') is the function as defined herein that determines the minimum number of sequence variations, polymorphisms or mutations (insertions, deletions, substitutions) that are needed to convert c to c', where c is a compomer of a fragment of the reference molecule and c' is the compomer of the target molecule resulting from mutation of the c fragment.

A substring (fragment) of the string s (full length sequence) is denoted s[i,j], where i,j are the start and end positions of the substring. Given a specific cleavage reaction of a base, amino acid, or other feature X recognized by the cleavage reagent in a string s, then the boundary b[i,j] of the substring s[i,j] or the corresponding compomer c[i,j] refers to a set of markers indicating whether cleavage of string s does not take place immediately outside the substring s[i,j]. Possible markers are L, indicating whether "s is not cleaved directly before i", and R, indicating whether "s is not cleaved directly after j". Thus, b[i,j] is a subset of the set {L,R} that contains L if and only if X is present at position i−1 of the string s, and contains R if and only if X is present at position j+1 of the string s. #b denotes the number of elements in the set b, which can be 0, 1, or 2, depending on whether the substring s[i,j] is specifically cleaved at both immediately flanking positions (i.e., at positions i−1 and j+1), at one immediately flanking position (i.e., at either position i−1 or j+1) or at no immediately flanking position (i.e., at neither position i−1 nor j+1). b[i,j] is a subset of the set {L,R} and denotes the boundary of s[i,j] as defined by the following:

b[i,j]:={L,R} if s is neither cleaved directly before i nor after j b[i,j]:={R} if s is cleaved directly before i, but not after j b[i,j]:={L} if s is cleaved directly after j, but not before i b[i,j]:={ } if s is cleaved directly before i and after j b[i,j] denotes the number of elements of the set b[i,j].

ord[i,j] refers to the number of times s[i,j] will be cleaved in a particular cleavage reaction; i.e., the number of cut strings present in s[i,j].

D(c',c,b):=d(c,c')+#b refers to the distance between compomer 'c and bounded compomer (c,b)'; i.e., the total minimum number of changes needed to create the fragment with compomer c' from the fragment with compomer c, including sequence variations of the boundaries of substring s[i,j] into cut strings, if necessary.

$C := \{(c[i,j], b[i,j]) : 1 \leq i \leq j \leq \text{length of } s\}$ refers to the set of all bounded compomers within the string s; i.e., for all possible substrings s[i,j], find the bounded compomer (c[i,j],b[i,j]) and these will belong to the set C.

$C_k := \{(c[i,j], b[i,j]) : 1 \leq i \leq j \leq \text{length of } s, \text{ and } \text{ord}[i,j] + \#b[i,j] \leq k\}$ is the same as C above, except that compomers for substrings containing more than k number of sequence variations of the cut string will be excluded from the set, i.e., $C_k$ is a subset of C. It can be shown that if there is a sequence variation containing at most k insertions, deletions, and substitutions, and if c' is a compomer corresponding to a peak witness of this sequence variation, then there exists (c,b) in $C_k$ such that $D(c',c,b) \leq k$. The algorithm is based on this reduced set of possible sequence variations corresponding to compomer witnesses.

Every sequence variation constructed in this fashion will lead to the creation of at least one different peak out of the list of input different peaks. Further, every sequence variation that contains at most k insertions, deletions, and insertions that was not constructed by the algorithm is either the superset of the union of one or more sequence variations that were constructed, or does not lead to the creation of any different peaks out of the list of different peaks that served as input for the algorithm.

Algorithm 1 can be repeated for more than one specific cleavage reagent generating more than one target fragmentation pattern relative to a reference fragmentation pattern, and more than one list of compomer witnesses. In one embodiment, the final output contains the set of sequence variation candidates that is the union of the sets of sequence variation candidates for each cleavage reaction.

Algorithm 2

A second algorithm is used to generate a simulated spectrum for each computed output sequence variation candidate. The simulated spectrum for each sequence variation candidate is scored, using a third (scoring) algorithm, described below, against the actual target spectrum, applying the reference spectrum for the reference sequence. The value of the scores (the higher the score, the better the match, with the highest score usually being the sequence variation that is most likely to be present) can then be used to determine the sequence variation candidate that is actually present in the target nucleic acid sequence.

Provided below is an exemplary algorithm where the sequence variations to be detected are SNPs. Algorithms for detecting other types of sequence variations, including homozygous or heterozygous allelic variations, can be implemented in a similar fashion.

a) For each cleavage reaction, a simulated spectrum is generated for a given sequence variation candidate from Algorithm 1.
b) The simulated spectrum is scored against the actual target spectrum.
c) The scores from all cleavage reactions, preferably complementary cleavage reactions, for the given target sequence are added. The use of more than one specific cleavage reaction improves the accuracy with which a particular sequence variation can be identified.
d) After all scores have been calculated for all sequence variations, sequence variations are sorted according to their score.

Algorithm 2

Find SNPs

INPUT: Reference sequences, one or more cleavage reaction, for every cleavage reaction a simulated or actual reference fragmentation spectrum, for every cleavage reaction a list of peaks found in the corresponding sample spectrum, maximal sequence variation order k.

OUTPUT: List of all SNP candidates corresponding to sequence variations containing at most k insertions, deletions, and substitutions, and that have a different peak as a witness; and for every such SNP candidate, a score.

For every cleavage reaction, extract the list of different peaks by comparing the sample spectrum with the simulated reference spectrum.

For every cleavage reaction, use FINDSEQUENCEVARIATIONCANDIDATES (Algorithm 1) with input s, the current cleavage reaction, the corresponding list of different peaks, and k.

Combine the lists of sequence variation candidates returned by FINDSEQUENCEVARIATIONCANDIDATES into a single list, removing duplicates.

For every sequence variation candidate:

Apply the sequence variation candidate, resulting in a sequence s'.

For every cleavage reaction, simulate the reference spectrum of s' under the given cleavage reaction.

Use SCORESNP (Algorithm 3) with the peak lists corresponding to the spectra of s,s' as well as the peak list for the measured sample spectrum as input, to calculate scores (heterozygous and homozygous) of this sequence variation (or SNP) candidate for the cleavage reaction.

Add up the scores of all cleavage reactions, keeping separate scores for heterozygous and homozygous variations.

Store a SNP candidate containing the sequence variation candidate plus its scores; the overall score of the SNP candidate is the maximum of its heterozygous and homozygous scores.

Sort the SNP candidates with respect to their scores.

Output the SNP candidates together with their scores.

An exemplary implementation of a scoring algorithm, SCORESNP, is as follows:

Algorithm 3

Score SNP

INPUT: Peak lists corresponding to reference sequence s (denoted L), modified reference sequence s' (denoted L'), and sample spectrum (denoted $L_s$).

OUTPUT: Heterozygous score, homozygous score.

Set both scores to 0.

Compute a list of intensity changes (denoted $L_A$) that includes those peaks in the lists corresponding to s,s' that show differences:

If a peak is present in L but not in L', add this peak to $L_A$ and mark it as wild-type.

If a peak is present in L' but not in L, add this peak to $L_A$ and mark it as mutant-type.

If a peak has different expected intensities in L and L', add this peak to $L_A$ together with the expected intensity change from L to L'.

For every peak in $L_A$ marked as mutant-type that is also found in $L_s$, add +1 to both scores.

For every peak in $L_A$ marked as mutant-type that is not found in $L_s$, add −1 to both scores.

For every peak in $L_A$ marked as wild-type that is not found in $L_s$, add +1 to the homozygous score.

For every peak in $L_A$ marked as wild-type that is also found in $L_s$, add −1 to the homozygous score.

Output both scores.

Other implementations of the scoring function will be obvious to those of skill in the art. For example, one implementation would make use of peaks that are not differentiated as either mutant or wild-type. Another implementation might, in addition or as a separate feature, take into account intensities in L, $L_A$, and $L_s$. Other exemplary parameters include using peaks designated as "wild-type" to modify the heterozygous score, or incorporation of a weighing function that is based on the confidence level in the actual (measured) target sequence fragmentation spectrum. A preferred implementation can use a logarithmic likelihood approach to calculate the scores.

In one embodiment, instead of using the scores of potential SNPs output by Algorithm 2 directly, scores from more than one target sequence expected to contain or actually containing the same SNP can be joined. When more than one target sequence is analyzed simultaneously against the same reference sequence, instead of reporting the SNP score for each target sequence independently, the scores of all identical scored sequence variations for the different target sequences may be joined to calculate a joined score for the SNP. The joined score can be calculated by applying a function to the set of scores, which function may include, but is not limited to, the maximum of scores, the sum of scores, or a combination thereof.

After all SNP or other sequence variation candidates with their scores have been calculated, a threshold score can be determined to report only those SNPs or sequence variations that have a score that is equal to or higher than the threshold score (and, therefore, a reasonable chance of being real, i.e., of corresponding to the actual sequence variation in the target sequence). Generally, the sequence variation with the highest score will correspond to an actual sequence variation in the target sequence. Sequence variations that are accepted as being real can then be used to modify the initial reference peak list L. The modified peak list can then be used to re-evaluate (score) all other potential sequence variations or SNPs using the SCORESNP algorithm, or even search for new witnesses in the case of homozygous SNPs. This leads to an iterative process of SNP or other sequence variation detection. For example, in the iterative process of detecting more than one sequence variation in a target sequence, the sequence variation with the highest score is accepted as an actual sequence variation, and the signal or peak corresponding to this sequence variation is added to the reference fragment spectrum to generate an updated reference fragment spectrum. All remaining sequence variation candidates are then scored against this updated reference fragment spectrum to output the sequence variation candidate with the next highest score. This second sequence variation candidate can also represent a second actual sequence variation in the target sequence. Therefore, the peak corresponding to the second sequence variation can be added to the reference fragment spectrum to generate a second updated reference spectrum against which a third sequence variation can be detected according to its score. This process of iteration can be repeated until no more sequence variation candidates representing actual sequence variations in the target sequence are identified.

The presented approach can be applied to any type and number of cleavage reactions that are complete, including 2-, 1½-, or 1¼-base cutters. In another embodiment, this approach can applied to partial cleavage experiments.

This approach is not limited to SNP and mutation detection but can be applied to detect any type of sequence variation, including polymorphisms, mutations and sequencing errors.

Since the presented algorithms are capable of dealing with homogeneous samples, it will be apparent to one of skill in the art that their use can be extended to the analysis of sample mixtures. Such "sample mixtures" usually contain the sequence variation or mutation or polymorphism containing target nucleic acid at very low frequency, with a high excess of wildtype sequence. For example, in tumors, the tumor-causing mutation is usually present in less than 5-10% of the nucleic acid present in the tumor sample, which is a heterogeneous mixture of more than one tissue type or cell type. Similarly, in a population of individuals, most polymorphisms with functional consequences that are determinative of, e.g., a disease state or predisposition to disease, occur at low allele frequencies of less than 5%. The methods provided herein can detect high frequency sequence variations or can be adapted to detect low frequency mutations, sequence variations, alleles or polymorphisms that are present in the range of less than about 5-10%.

D. APPLICATIONS

1. Detection of Polymorphisms

An object herein is to provide improved methods for identifying the genomic basis of disease and markers thereof. The sequence variation candidates identified by the methods provided herein include sequences containing sequence variations that are polymorphisms. Polymorphisms include both naturally occurring, somatic sequence variations and those arising from mutation. Polymorphisms include but are not limited to: sequence microvariants where one or more nucleotides in a localized region vary from individual to individual, insertions and deletions which can vary in size from one nucleotides to millions of bases, and microsatellite or nucleotide repeats which vary by numbers of repeats. Nucleotide repeats include homogeneous repeats such as dinucleotide, trinucleotide, tetranucleotide or larger repeats, where the same sequence in repeated multiple times, and also heteronucleotide repeats where sequence motifs are found to repeat. For a given locus the number of nucleotide repeats can vary depending on the individual.

A polymorphic marker or site is the locus at which divergence occurs. Such site can be as small as one base pair (an SNP). Polymorphic markers include, but are not limited to, restriction fragment length polymorphisms (RFLPs), variable number of tandem repeats (VNTR's), hypervariable regions, minisatellites, dinucleotide repeats, trinucleotide repeats, tetranucleotide repeats and other repeating patterns, simple sequence repeats and insertional elements, such as Alu. Polymorphic forms also are manifested as different mendelian alleles for a gene. Polymorphisms can be observed by differences in proteins, protein modifications, RNA expression modification, DNA and RNA methylation, regulatory factors that alter gene expression and DNA replication, and any other manifestation of alterations in genomic nucleic acid or organelle nucleic acids.

Furthermore, numerous genes have polymorphic regions. Since individuals have any one of several allelic variants of a polymorphic region, individuals can be identified based on the type of allelic variants of polymorphic regions of genes. This can be used, for example, for forensic purposes. In other situations, it is crucial to know the identity of allelic variants that an individual has. For example, allelic differences in certain genes, for example, major histocompatibility complex (MHC) genes, are involved in graft rejection or graft versus host disease in bone marrow transportation. Accordingly, it is highly desirable to develop rapid, sensitive, and accurate methods for determining the identity of allelic variants of polymorphic regions of genes or genetic lesions. A method or a kit as provided herein can be used to genotype a subject by determining the identity of one or more allelic variants of one or more polymorphic regions in one or more genes or chromosomes of the subject. Genotyping a subject using a method as provided herein can be used for forensic or identity testing purposes and the polymorphic regions can be present in mitochondrial genes or can be short tandem repeats.

Single nucleotide polymorphisms (SNPs) are generally biallelic systems, that is, there are two alleles that an individual can have for any particular marker. This means that the information content per SNP marker is relatively low when compared to microsatellite markers, which can have upwards of 10 alleles. SNPs also tend to be very population-specific; a marker that is polymorphic in one population can not be very polymorphic in another. SNPs, found approximately every kilobase (see Wang et al. (1998) Science 280:1077-1082), offer the potential for generating very high density genetic maps, which will be extremely useful for developing haplotyping systems for genes or regions of interest, and because of the nature of SNPS, they can in fact be the polymorphisms associated with the disease phenotypes under study. The low mutation rate of SNPs also makes them excellent markers for studying complex genetic traits.

Much of the focus of genomics has been on the identification of SNPs, which are important for a variety of reasons. They allow indirect testing (association of haplotypes) and direct testing (functional variants). They are the most abundant and stable genetic markers. Common diseases are best explained by common genetic alterations, and the natural variation in the human population aids in understanding disease, therapy and environmental interactions.

2. Pathogen Typing

Provided herein is a process or method for identifying strains of microorganisms. The microorganism(s) are selected from a variety of organisms including, but not limited to, bacteria, fungi, protozoa, ciliates, and viruses. The microorganisms are not limited to a particular genus, species, strain, or serotype. The microorganisms can be identified by determining sequence variations in a target microorganism sequence relative to one or more reference sequences. The reference sequence(s) can be obtained from, for example, other microorganisms from the same or different genus, species strain or serotype, or from a host prokaryotic or eukaryotic organism.

Identification and typing of bacterial pathogens is critical in the clinical management of infectious diseases. Precise identity of a microbe is used not only to differentiate a disease state from a healthy state, but is also fundamental to determining whether and which antibiotics or other antimicrobial therapies are most suitable for treatment. Traditional methods of pathogen typing have used a variety of phenotypic features, including growth characteristics, color, cell or colony morphology, antibiotic susceptibility, staining, smell and reactivity with specific antibodies to identify bacteria. All of these methods require culture of the suspected pathogen, which suffers from a number of serious shortcomings, including high material and labor costs, danger of worker exposure, false positives due to mishandling and false negatives due to low numbers of viable cells or due to the fastidious culture requirements of many pathogens. In addition, culture methods require a relatively long time to achieve diagnosis, and because of the potentially life-threatening nature of such infections, antimicrobial therapy is often started before the results can be obtained.

In many cases, the pathogens are very similar to the organisms that make up the normal flora, and can be indistinguishable from the innocuous strains by the methods cited above. In these cases, determination of the presence of the pathogenic strain can require the higher resolution afforded by the molecular typing methods provided herein. For example, PCR amplification of a target nucleic acid sequence followed by fragmentation by specific cleavage (e.g., base-specific), followed by matrix-assisted laser desorption/ionization time-of-flight mass spectrometry, followed by screening for sequence variations as provided herein, allows reliable discrimination of sequences differing by only one nucleotide and combines the discriminatory power of the sequence information generated with the speed of MALDI-TOF MS.

3. Detecting the Presence of Viral or Bacterial Nucleic Acid Sequences Indicative of an Infection The methods provided herein can be used to determine the presence of viral or bacterial nucleic acid sequences indicative of an infection by identifying sequence variations that are present in the viral or bacterial nucleic acid sequences relative to one or more reference sequences. The reference sequence(s) can include, but are not limited to, sequences obtained from related non-infectious organisms, or sequences from host organisms.

Viruses, bacteria, fungi and other infectious organisms contain distinct nucleic acid sequences, including polymorphisms, which are different from the sequences contained in the host cell. A target DNA sequence can be part of a foreign genetic sequence such as the genome of an invading microorganism, including, for example, bacteria and their phages, viruses, fungi, protozoa, and the like. The processes provided herein are particularly applicable for distinguishing between different variants or strains of a microorganism in order, for example, to choose an appropriate therapeutic intervention. Examples of disease-causing viruses that infect humans and animals and that can be detected by a disclosed process include but are not limited to Retroviridae (e.g., human immunodeficiency viruses such as HIV-1 (also referred to as HTLV-III, LAV or HTLV-III/LAV; Ratner et al., *Nature*, 313: 227-284 (1985); Wain Hobson et al., *Cell*, 40:9-17 (1985), HIV-2 (Guyader et al., *Nature*, 328:662-669 (1987); European Patent Publication No. 0 269 520; Chakrabarti et al., *Nature*, 328:543-547 (1987); European Patent Application No. 0 655 501), and other isolates such as HIV-LP (International Publication No. WO 94/00562); Picornaviridae (e.g., polioviruses, hepatitis A virus, (Gust et al., *Intervirology*, 20:1-7 (1983)); enteroviruses, human coxsackie viruses, rhinoviruses, echoviruses); Calcivirdae (e.g. strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses);

Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arenaviridae (hemorrhagic fever viruses); Reoviridae (e.g., reoviruses, orbiviruses and rotaviruses); Birnaviridae; Hepadnaviridae (*Hepatitis B* virus); Parvoviridae (parvoviruses); Papovaviridae; Hepadnaviridae (Hepatitis B virus); Parvoviridae (most adenoviruses); Papovaviridae (papilloma viruses, polyoma viruses); Adenoviridae (most adenoviruses); Herpesviridae (herpes simplex virus type 1 (HSV-1) and HSV-2, varicella zoster virus, cytomegalovirus, herpes viruses; Poxviridae (variola viruses, vaccinia viruses, pox viruses); Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted, i.e., Hepatitis C); Norwalk and related viruses, and astroviruses.

Examples of infectious bacteria include but are not limited to *Helicobacter pyloris, Borelia burgdorferi, Legionella pneumophilia, Mycobacteria* sp. (e.g. *M. tuberculosis, M. avium, M. intracellulare, M. kansaii, M. gordonae*), *Staphylococcus aureus, Neisseria gonorrheae, Neisseria meningitidis, Listeria monocytogenes, Streptococcus pyogenes* (Group A *Streptococcus*), *Streptococcus agalactiae* (Group B *Streptococcus*), *Streptococcus* sp. (viridans group), *Streptococcus faecalis, Streptococcus bovis, Streptococcus* sp. (anaerobic species), *Streptococcus pneumoniae*, pathogenic *Campylobacter* sp., *Enterococcus* sp., *Haemophilus influenzae, Bacillus antracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, and *Actinomyces israelli*.

Examples of infectious fungi include but are not limited to *Cryptococcus neoformans, Histoplasma capsulatum, Coccidioides immitis, Blastomyces dermatitidis, Chlamydia trachomatis, Candida albicans*. Other infectious organisms include protists such as *Plasmodium falciparum* and *Toxoplasma gondii*.

4. Antibiotic Profiling

The analysis of specific cleavage fragmentation patterns as provided herein improves the speed and accuracy of detection of nucleotide changes involved in drug resistance, including antibiotic resistance. Genetic loci involved in resistance to isoniazid, rifampin, streptomycin, fluoroquinolones, and ethionamide have been identified [Heym et al., Lancet 344: 293 (1994) and Morris et al., J. Infect. Dis. 171:954 (1995)]. A combination of isoniazid (inh) and rifampin (rif) along with pyrazinamide and ethambutol or streptomycin, is routinely used as the first line of attack against confirmed cases of *M. tuberculosis* [Banerjee et al., Science 263:227 (1994)]. The increasing incidence of such resistant strains necessitates the development of rapid assays to detect them and thereby reduce the expense and community health hazards of pursuing ineffective, and possibly detrimental, treatments. The identification of some of the genetic loci involved in drug resistance has facilitated the adoption of mutation detection technologies for rapid screening of nucleotide changes that result in drug resistance.

5. Identifying Disease Markers

Provided herein are methods for the rapid and accurate identification of sequence variations that are genetic markers of disease, which can be used to diagnose or determine the prognosis of a disease. Diseases characterized by genetic markers can include, but are not limited to, atherosclerosis, obesity, diabetes, autoimmune disorders, and cancer. Diseases in all organisms have a genetic component, whether inherited or resulting from the body's response to environmental stresses, such as viruses and toxins. The ultimate goal of ongoing genomic research is to use this information to develop new ways to identify, treat and potentially cure these diseases. The first step has been to screen disease tissue and identify genomic changes at the level of individual samples. The identification of these "disease" markers is dependent on the ability to detect changes in genomic markers in order to identify errant genes or polymorphisms. Genomic markers (all genetic loci including single nucleotide polymorphisms (SNPs), microsatellites and other noncoding genomic regions, tandem repeats, introns and exons) can be used for the identification of all organisms, including humans. These markers provide a way to not only identify populations but also allow stratification of populations according to their response to disease, drug treatment, resistance to environmental agents, and other factors.

6. Haplotyping

The methods provided herein can be used to detect haplotypes. In any diploid cell, there are two haplotypes at any gene or other chromosomal segment that contain at least one distinguishing variance. In many well-studied genetic systems, haplotypes are more powerfully correlated with phenotypes than single nucleotide variations. Thus, the determination of haplotypes is valuable for understanding the genetic basis of a variety of phenotypes including disease predisposition or susceptibility, response to therapeutic interventions, and other phenotypes of interest in medicine, animal husbandry, and agriculture.

Haplotyping procedures as provided herein permit the selection of a portion of sequence from one of an individual's two homologous chromosomes and to genotype linked SNPs on that portion of sequence. The direct resolution of haplotypes can yield increased information content, improving the diagnosis of any linked disease genes or identifying linkages associated with those diseases.

7. Microsatellites

The fragmentation-based methods provided herein allow for rapid, unambiguous detection of sequence variations that are microsatellites. Microsatellites (sometimes referred to as variable number of tandem repeats or VNTRs) are short tandemly repeated nucleotide units of one to seven or more bases, the most prominent among them being di-, tri-, and tetranucleotide repeats. Microsatellites are present every 100, 000 bp in genomic DNA (J. L. Weber and P. E. Can, Am. J. Hum. Genet. 44, 388 (1989); J. Weissenbach et al., Nature 359, 794 (1992)). CA dinucleotide repeats, for example, make up about 0.5% of the human extra-mitochondrial genome; CT and AG repeats together make up about 0.2%. CG repeats are rare, most probably due to the regulatory function of CpG islands. Microsatellites are highly polymorphic with respect to length and widely distributed over the whole genome with a main abundance in non-coding sequences, and their function within the genome is unknown.

Microsatellites are important in forensic applications, as a population will maintain a variety of microsatelites characteristic for that population and distinct from other populations which do not interbreed.

Many changes within microsatellites can be silent, but some can lead to significant alterations in gene products or expression levels. For example, trinucleotide repeats found in the coding regions of genes are affected in some tumors (C. T. Caskey et al., Science 256, 784 (1992) and alteration of the microsatellites can result in a genetic instability that results in a predisposition to cancer (P. J. McKinnen, Hum. Genet. 1 75, 197 (1987); J. German et al., Clin. Genet. 35, 57 (1989)).

8. Short Tandem Repeats

The methods provided herein can be used to identify short tandem repeat (STR) regions in some target sequences of the human genome relative to, for example, reference sequences in the human genome that do not contain STR regions. STR regions are polymorphic regions that are not related to any disease or condition. Many loci in the human genome contain a polymorphic short tandem repeat (STR) region. STR loci contain short, repetitive sequence elements of 3 to 7 base pairs in length. It is estimated that there are 200,000 expected trimeric and tetrameric STRs, which are present as frequently as once every 15 kb in the human genome (see, e.g., International PCT application No. WO 9213969 A1, Edwards et al., Nucl. Acids Res. 19:4791 (1991); Beckmann et al. (1992) Genomics 12:627-631). Nearly half of these STR loci are polymorphic, providing a rich source of genetic markers. Variation in the number of repeat units at a particular locus is responsible for the observed polymorphism reminiscent of variable nucleotide tandem repeat (VNTR) loci (Nakamura et al. (1987) Science 235:1616-1622); and minisatellite loci (Jeffreys et al. (1985) Nature 314:67-73), which contain longer repeat units, and microsatellite or dinucleotide repeat loci (Luty et al. (1991) Nucleic Acids Res. 19:4308; Litt et al. (1990) Nucleic Acids Res. 18:4301; Litt et al. (1990) Nucleic Acids Res. 18:5921; Luty et al. (1990) Am. J. Hum. Genet. 46:776-783; Tautz (1989) Nucl. Acids Res. 17:6463-6471; Weber et al. (1989) Am. J. Hum. Genet. 44:388-396; Beckmann et al. (1992) Genomics 12:627-631).

Examples of STR loci include, but are not limited to, pentanucleotide repeats in the human CD4 locus (Edwards et al., Nucl. Acids Res. 19:4791 (1991)); tetranucleotide repeats in the human aromatase cytochrome P-450 gene (CYP19; Polymeropoulos et al., Nucl. Acids Res. 19:195 (1991)); tetranucleotide repeats in the human coagulation factor XIII A subunit gene (F13A1; Polymeropoulos et al., Nucl. Acids Res. 19:4306 (1991)); tetranucleotide repeats in the F13B locus (Nishimura et al., Nucl. Acids Res. 20:1167 (1992)); tetranucleotide repeats in the human c-les/fps, proto-oncogene (FES; Polymeropoulos et al., Nucl. Acids Res. 19:4018 (1991)); tetranucleotide repeats in the LFL gene (Zuliani et al., Nucl. Acids Res. 18:4958 (1990)); trinucleotide repeats polymorphism at the human pancreatic phospholipase A-2 gene (PLA2; Polymeropoulos et al., Nucl. Acids Res. 18:7468 (1990)); tetranucleotide repeats polymorphism in the VWF gene (Ploos et al., Nucl. Acids Res. 18:4957 (1990)); and tetranucleotide repeats in the human thyroid peroxidase (hTPO) locus (Anker et al., Hum. Mol. Genet. 1:137 (1992)).

9. Organism Identification

Polymorphic STR loci and other polymorphic regions of genes are sequence variations that are extremely useful markers for human identification, paternity and maternity testing, genetic mapping, immigration and inheritance disputes, zygosity testing in twins, tests for inbreeding in humans, quality control of human cultured cells, identification of human remains, and testing of semen samples, blood stains and other material in forensic medicine. Such loci also are useful markers in commercial animal breeding and pedigree analysis and in commercial plant breeding. Traits of economic importance in plant crops and animals can be identified through linkage analysis using polymorphic DNA markers. Efficient and accurate methods for determining the identity of such loci are provided herein.

10. Detecting Allelic Variation

The methods provided herein allow for high-throughput, fast and accurate detection of allelic variants. Studies of allelic variation involve not only detection of a specific sequence in a complex background, but also the discrimination between sequences with few, or single, nucleotide differences. One method for the detection of allele-specific variants by PCR is based upon the fact that it is difficult for Taq polymerase to synthesize a DNA strand when there is a mismatch between the template strand and the 3' end of the primer. An allele-specific variant can be detected by the use of a primer that is perfectly matched with only one of the possible alleles; the mismatch to the other allele acts to prevent the extension of the primer, thereby preventing the amplification of that sequence. This method has a substantial limitation in that the base composition of the mismatch influences the ability to prevent extension across the mismatch, and certain mismatches do not prevent extension or have only a minimal effect (Kwok et al., Nucl. Acids Res., 18:999 [1990]).) The fragmentation-based methods provided herein overcome the limitations of the primer extension method.

11. Determining Allelic Frequency

The methods herein described are valuable for identifying one or more genetic markers whose frequency changes within the population as a function of age, ethnic group, sex or some other criteria. For example, the age-dependent distribution of ApoE genotypes is known in the art (see, Schächter et al. (1994) Nature Genetics 6:29-32). The frequencies of polymorphisms known to be associated at some level with disease can also be used to detect or monitor progression of a disease state. For example, the N291S polymorphism (N291S) of the Lipoprotein Lipase gene, which results in a substitution of a serine for an asparagine at amino acid codon 291, leads to reduced levels of high density lipoprotein cholesterol (HDL-C) that is associated with an increased risk of males for arteriosclerosis and in particular myocardial infarction (see, Reymer et al. (1995) Nature Genetics 10:28-34). In addition, determining changes in allelic frequency can allow the identification of previously unknown polymorphisms and ultimately a gene or pathway involved in the onset and progression of disease.

12. Epigenetics

The methods provided herein can be used to study variations in a target nucleic acid or protein relative to a reference nucleic acid or protein that are not based on sequence, e.g., the identity of bases or amino acids that are the naturally occurring monomeric units of the nucleic acid or protein. For example, the specific cleavage reagents employed in the methods provided herein may recognize differences in sequence-independent features such as methylation patterns, the presence of modified bases or amino acids, or differences in higher order structure between the target molecule and the reference molecule, to generate fragments that are cleaved at sequence-independent sites. Epigenetics is the study of the inheritance of information based on differences in gene expression rather than differences in gene sequence. Epigenetic changes refer to mitotically and/or meiotically heritable changes in gene function or changes in higher order nucleic acid structure that cannot be explained by changes in nucleic acid sequence. Examples of features that are subject to epigenetic variation or change include, but are not limited to, DNA methylation patterns in animals, histone modification and the Polycomb-trithorax group (Pc-G/tx) protein complexes (see, e.g., Bird, A., *Genes Dev.*, 16:6-21 (2002)).

Epigenetic changes usually, although not necessarily, lead to changes in gene expression that are usually, although not necessarily, inheritable. For example, as discussed further below, changes in methylation patterns is an early event in cancer and other disease development and progression. In many cancers, certain genes are inappropriately switched off or switched on due to aberrant methylation. The ability of methylation patterns to repress or activate transcription can be inherited. The Pc-G/trx protein complexes, like methylation, can repress transcription in a heritable fashion. The Pc-G/trx multiprotein assembly is targeted to specific regions of the genome where it effectively freezes the embryonic gene expression status of a gene, whether the gene is active or inactive, and propagates that state stably through development. The ability of the Pc-G/trx group of proteins to target and bind to a genome affects only the level of expression of the genes contained in the genome, and not the properties of the gene products. The methods provided herein can be used with specific cleavage reagents that identify variations in a target sequence relative to a reference sequence that are based on sequence-independent changes, such as epigenetic changes.

13. Methylation Patterns

The methods provided herein can be used to detect sequence variations that are epigenetic changes in the target sequence, such as a change in methylation patterns in the target sequence. Analysis of cellular methylation is an emerging research discipline. The covalent addition of methyl groups to cytosine is primarily present at CpG dinucleotides (microsatellites). Although the function of CpG islands not located in promoter regions remains to be explored, CpG islands in promoter regions are of special interest because their methylation status regulates the transcription and expression of the associated gene. Methylation of promotor regions leads to silencing of gene expression. This silencing is permanent and continues through the process of mitosis. Due to its significant role in gene expression, DNA methylation has an impact on developmental processes, imprinting and X-chromosome inactivation as well as tumor genesis, aging, and also suppression of parasitic DNA. Methylation is thought to be involved in the cancerogenesis of many widespread tumors, such as lung, breast, and colon cancer, an in leukemia. There is also a relation between methylation and protein dysfunctions (long Q-T syndrome) or metabolic diseases (transient neonatal diabetes, type 2 diabetes).

Bisulfite treatment of genomic DNA can be utilized to analyze positions of methylated cytosine residues within the DNA. Treating nucleic acids with bisulfite deaminates cytosine residues to uracil residues, while methylated cytosine remains unmodified. Thus, by comparing the sequence of a target nucleic acid that is not treated with bisulfite with the sequence of the nucleic acid that is treated with bisulfite in the methods provided herein, the degree of methylation in a nucleic acid as well as the positions where cytosine is methylated can be deduced.

Methylation analysis via restriction endonuclease reaction is made possible by using restriction enzymes which have methylation-specific recognition sites, such as HpaII and MSPI. The basic principle is that certain enzymes are blocked by methylated cytosine in the recognition sequence. Once this differentiation is accomplished, subsequent analysis of the resulting fragments can be performed using the methods as provided herein.

These methods can be used together in combined bisulfite restriction analysis (COBRA). Treatment with bisulfite causes a loss in BstUI recognition site in amplified PCR product, which causes a new detectable fragment to appear on analysis compared to untreated sample. The fragmentation-based methods provided herein can be used in conjunction with specific cleavage of methylation sites to provide rapid, reliable information on the methylation patterns in a target nucleic acid sequence.

14. Resequencing

The dramatically growing amount of available genomic sequence information from various organisms increases the need for technologies allowing large-scale comparative sequence analysis to correlate sequence information to function, phenotype, or identity. The application of such technologies for comparative sequence analysis can be widespread, including SNP discovery and sequence-specific identification of pathogens. Therefore, resequencing and high-throughput mutation screening technologies are critical to the identification of mutations underlying disease, as well as the genetic variability underlying differential drug response.

Several approaches have been developed in order to satisfy these needs. The current technology for high-throughput DNA sequencing includes DNA sequencers using electrophoresis and laser-induced fluorescence detection. Electrophoresis-based sequencing methods have inherent limitations for detecting heterozygotes and are compromised by GC compressions. Thus a DNA sequencing platform that produces digital data without using electrophoresis will overcome these problems. Matrix-assisted laser desorption/ionization time-of-flight mass spectrometry (MALDI-TOF MS) measures DNA fragments with digital data output. The methods of specific cleavage fragmentation analysis provided herein allow for high-throughput, high speed and high accuracy in the detection of sequence variations relative to a reference sequence. This approach makes it possible to routinely use MALDI-TOF MS sequencing for accurate mutation detection, such as screening for founder mutations in BRCA1 and BRCA2, which are linked to the development of breast cancer.

15. Multiplexing

The methods provided herein allow for the high-throughput detection or discovery of sequence variations in a plurality of target sequences relative to one or a plurality of reference sequences. Multiplexing refers to the simultaneous detection of more than one polymorphism or sequence variation. Methods for performing multiplexed reactions, particularly in conjunction with mass spectrometry, are known (see, e.g., U.S. Pat. Nos. 6,043,031, 5,547,835 and International PCT application No. WO 97/37041).

Multiplexing can be performed, for example, for the same target nucleic acid sequence using different complementary specific cleavage reactions as provided herein, or for different target nucleic acid sequences, and the fragmentation patterns can in turn be analyzed against a plurality of reference nucleic acid sequences. Several mutations or sequence variations can also be simultaneously detected on one target sequence by employing the methods provided herein where each sequence variation corresponds to a different cleavage fragment relative to the fragmentation pattern of the reference nucleic acid sequence. Multiplexing provides the advantage that a plurality of sequence variations can be identified in as few as a single mass spectrum, as compared to having to perform a separate mass spectrometry analysis for each individual sequence variation. The methods provided herein lend themselves to high-throughput, highly-automated processes for analyzing sequence variations with high speed and accuracy.

E. SYSTEM AND SOFTWARE METHOD

Also provided are systems that automate the methods for determining sequence variations in a target nucleic acid or protein or the detection methods provided herein using a computer programmed for identifying the sequence variations based upon the methods provided herein. The methods herein can be implemented, for example, by use of the following computer systems and using the following calculations, systems and methods.

An exemplary automated testing system contains a nucleic acid workstation that includes an analytical instrument, such as a gel electrophoresis apparatus or a mass spectrometer or other instrument for determining the mass of a nucleic acid molecule in a sample, and a computer for fragmentation data analysis capable of communicating with the analytical instrument (see, e.g., copending U.S. application Ser. Nos. 09/285,481, 09/663,968 and 09/836,629; see, also International PCT application No. WO 00/60361 for exemplary automated systems). In an exemplary embodiment, the computer is a desktop computer system, such as a computer that operates under control of the "Microsoft Windows" operation system of Microsoft Corporation or the "Macintosh" operating system of Apple Computer, Inc., that communicates with the instrument using a known communication standard such as a parallel or serial interface.

For example, systems for analysis of nucleic acid samples are provided. The systems include a processing station that performs a base-specific or other specific cleavage reaction as described herein; a robotic system that transports the resulting cleavage fragments from the processing station to a mass measuring station, where the masses of the products of the reaction are determined; and a data analysis system, such as a computer programmed to identify sequence variations in the target nucleic acid sequence using the fragmentation data, that processes the data from the mass measuring station to identify a nucleotide or plurality thereof in a sample or plurality thereof. The system can also include a control system that determines when processing at each station is complete and, in response, moves the sample to the next test station, and continuously processes samples one after another until the control system receives a stop instruction.

Figure 3:
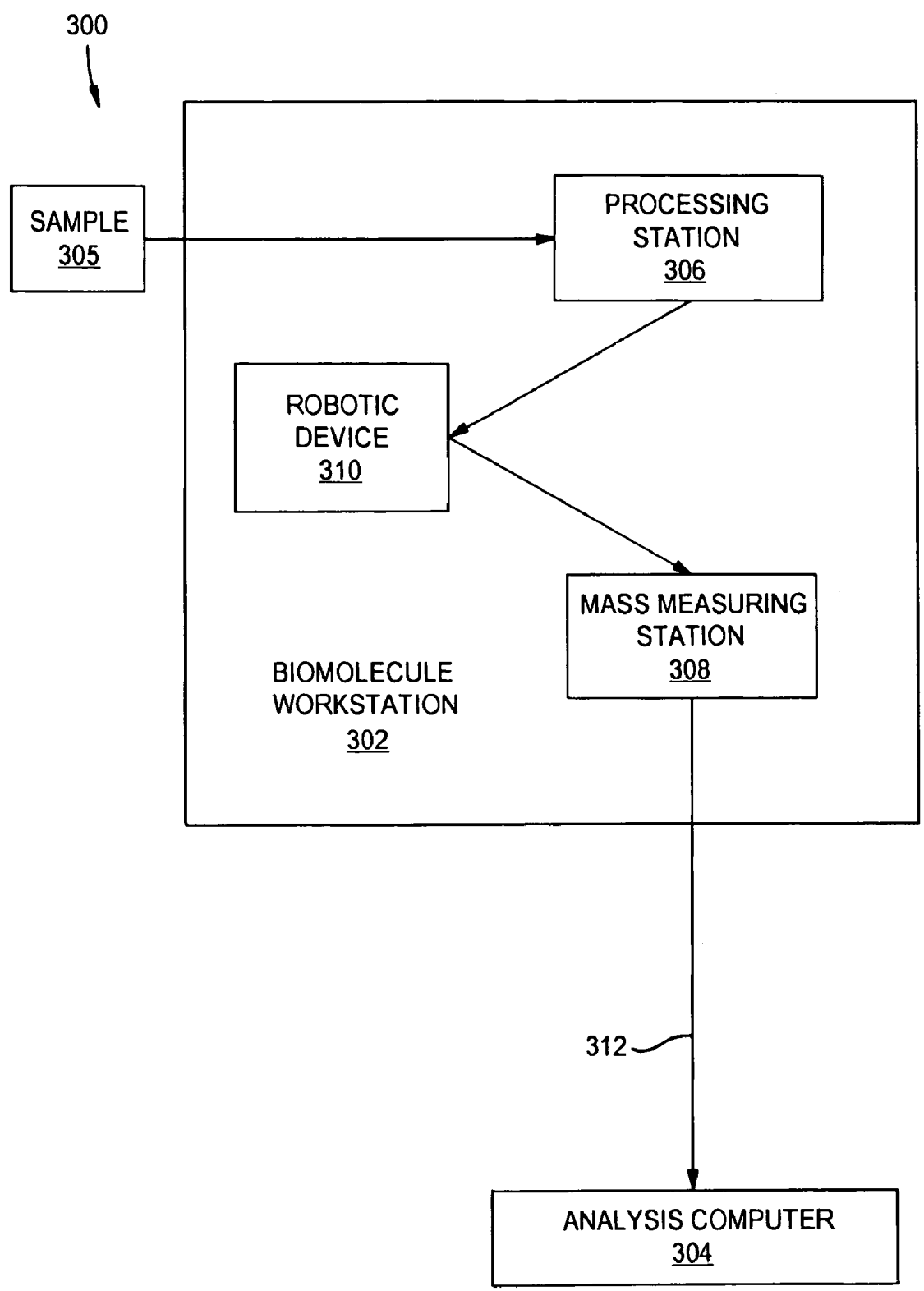
FIG. 3 is a block diagram of a system that performs sample processing and performs the operations illustrated in FIGS. 1 and 2.

FIG. 3 is a block diagram of a system that performs sample processing and performs the operations illustrated in FIG. 1 and FIG. 2. The system 300 includes a nucleic acid workstation 302 and an analysis computer 304. At the nucleic work station, one or more molecular samples 305 are received and prepared for analysis at a processing station 306, where the above-described cleavage reactions can take place. The samples are then moved to a mass measuring station 308, such as a mass spectrometer, where further sample processing takes place. The samples are preferably moved from the sample processing station 306 to the mass measuring station 308 by a computer-controlled robotic device 310.

The robotic device can include subsystems that ensure movement between the two processing stations 306, 308 that will preserve the integrity of the samples 305 and will ensure valid test results. The subsystems can include, for example, a mechanical lifting device or arm that can pick up a sample from the sample processing station 306, move to the mass measuring station 308, and then deposit the processed sample for a mass measurement operation. The robotic device 310 can then remove the measured sample and take appropriate action to move the next processed sample from the processing station 306.

The mass measurement station 308 produces data that identifies and quantifies the molecular components of the sample 305 being measured. Those skilled in the art will be familiar with molecular measurement systems, such as mass spectrometers, that can be used to produce the measurement data. The data is provided from the mass measuring station 308 to the analysis computer 304, either by manual entry of measurement results into the analysis computer or by communication between the mass measuring station and the analysis computer. For example, the mass measuring station 308 and the analysis computer 304 can be interconnected over a network 312 such that the data produced by the mass measuring station can be obtained by the analysis computer. The network 312 can comprise a local area network (LAN), or a wireless communication channel, or any other communications channel that is suitable for computer-to-computer data exchange.

The measurement processing function of the analysis computer 304 and the control function of the nucleic acid workstation 302 can be incorporated into a single computer device, if desired. In that configuration, for example, a single general purpose computer can be used to control the robotic device 310 and to perform the data processing of the data analysis computer 304. Similarly, the processing operations of the mass measuring station and the sample processing operations of the sample processing station 306 can be performed under the control of a single computer.

Thus, the processing and analysis functions of the stations and computers 302, 304, 306, 308, 310 can be performed by variety of computing devices, if the computing devices have a suitable interface to any appropriate subsystems (such as a mechanical arm of the robotic device 310) and have suitable processing power to control the systems and perform the data processing.

The data analysis computer 304 can be part of the analytical instrument or another system component or it can be at a remote location. The computer system can communicate with the instrument can communicate with the instrument, for example, through a wide area network or local area communication network or other suitable communication network. The system with the computer is programmed to automatically carry out steps of the methods herein and the requisite calculations. For embodiments that use predicted fragmentation patterns (of a reference or target sequence) based on the cleavage reagent(s) and modified bases or amino acids employed, a user enters the masses of the predicted fragments. These data can be directly entered by the user from a keyboard or from other computers or computer systems linked by network connection, or on removable storage medium such as a data CD, minidisk (MD), DVD, floppy disk or other suitable storage medium. Next, the user initiates execution software that operates the system in which the fragment differences between the target nucleic acid sequence and the reference nucleic acid sequence, are identified. The sequence variation software performs the steps of Algorithm 1 and, in some embodiments, Algorithms 2 or 3 as described herein.

Figure 4:
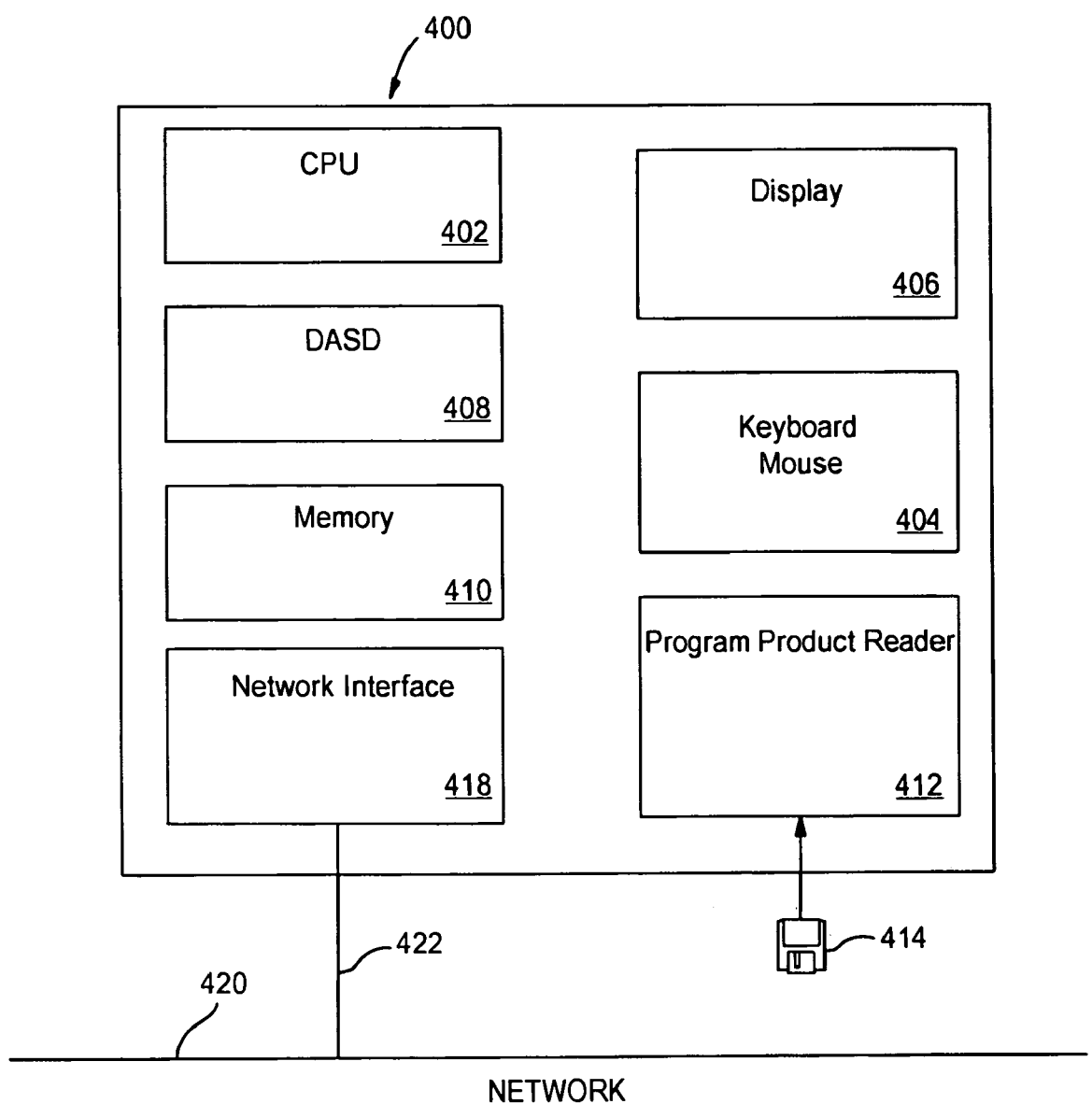
FIG. 4 is a block diagram of the data analysis computer illustrated in FIG. 3.

FIG. 4 is a block diagram of a computer in the system 300 of FIG. 3, illustrating the hardware components included in a computer that can provide the functionality of the stations and computers 302, 304, 306, 308. Those skilled in the art will appreciate that the stations and computers illustrated in FIG. 3 can all have a similar computer construction, or can have alternative constructions consistent with the capabilities and respective functions described herein. The FIG. 4 construction is especially suited for the data analysis computer 304 illustrated in FIG. 3.

FIG. 4 shows an exemplary computer 400 such as might comprise a computer that controls the operation of any of the stations and analysis computers 302, 304, 306, 308. Each computer 400 operates under control of a central processor unit (CPU) 402, such as a "Pentium" microprocessor and associated integrated circuit chips, available from Intel Corporation of Santa Clara, Calif., USA. A computer user can input commands and data from a keyboard and computer mouse 404, and can view inputs and computer output at a display 406. The display is typically a video monitor or flat panel display. The computer 400 also includes a direct access storage device (DASD) 408, such as a hard disk drive. The computer includes a memory 410 that typically comprises volatile semiconductor random access memory (RAM). Each computer preferably includes a program product reader 412 that accepts a program product storage device 414, from which the program product reader can read data (and to which it can optionally write data). The program product reader can comprise, for example, a disk drive, and the program product storage device can comprise removable storage media such as a magnetic floppy disk, a CD-R disc, a CD-RW disc, or DVD disc.

Each computer 400 can communicate with the other FIG. 3 systems over a computer network 420 (such as, for example, the local network 312 or the Internet or an intranet) through a network interface 418 that enables communication over a connection 422 between the network 420 and the computer. The network interface 418 typically comprises, for example, a Network Interface Card (NIC) that permits communication over a variety of networks, along with associated network access subsystems, such as a modem.

The CPU 402 operates under control of programming instructions that are temporarily stored in the memory 410 of the computer 400. When the programming instructions are executed, the computer performs its functions. Thus, the programming instructions implement the functionality of the respective workstation or processor. The programming instructions can be received from the DASD 408, through the program product storage device 414, or through the network connection 422. The program product storage drive 412 can receive a program product 414, read programming instructions recorded thereon, and transfer the programming instructions into the memory 410 for execution by the CPU 402. As noted above, the program product storage device can comprise any one of multiple removable media having recorded computer-readable instructions, including magnetic floppy disks and CD-ROM storage discs. Other suitable program product storage devices can include magnetic tape and semiconductor memory chips. In this way, the processing instructions necessary for operation in accordance with them methods and disclosure herein can be embodied on a program product.

Alternatively, the program instructions can be received into the operating memory 410 over the network 420. In the network method, the computer 400 receives data including program instructions into the memory 410 through the network interface 418 after network communication has been established over the network connection 422 by well-known methods that will be understood by those skilled in the art without further explanation. The program instructions are then executed by the CPU 402 thereby comprising a computer process.

It should be understood that all of the stations and computers of the system 300 illustrated in FIG. 3 can have a construction similar to that shown in FIG. 4, so that details described with respect to the FIG. 4 computer 400 will be understood to apply to all computers of the system 300. It should be appreciated that any of the communicating stations and computers can have an alternative construction, so long as they can communicate with the other communicating stations and computers illustrated in FIG. 3 and can support the functionality described herein. For example, if a workstation will not receive program instructions from a program product device, then it is not necessary for that workstation to include that capability, and that workstation will not have the elements depicted in FIG. 4 that are associated with that capability.

The following Examples are included for illustrative purposes only and are not intended to limit the scope of the invention.

Example 1

Base-Specific Cleavage of RNA

Provided herein is a semi-automated protocol for a one tube reaction including RNA transcription and a G-specific endonucleolytic cleavage reaction with the exemplary RNAse, RNase T1, to analyze sequence variations of a target nucleic acid of interest. The fragments produced by the RNAse cleavage method as provided herein can be analyzed according to the methods provided herein. The RNase T1 reaction is carried out to about 100% cleavage at the G nucleotide sites on the target nucleic acid. This cleavage produces a characteristic pattern of fragment masses, which is indicative of the sequence variations in a target sequence of interest.

Materials and Methods

Oligonucleotides were purchased from Metabion (Germany). 5-Methylcytidine 5'-triphosphate lithium salt (Me-CTP) and 5-Methyluridine 5'-triphosphate lithium salt (Me-UTP) were obtained from Trilink (USA).

PCR Amplification

A 5 µl PCR reaction contained 5 ng of genomic DNA, 0.1 units of HotStarTaq DNA Polymerase (Qiagen, Germany), 1 pmol each of forward and reverse primer, 0.2 mM of each dNTP and 1× HotStarTaq PCR buffer as supplied by the enzyme manufacturer (Qiagen, Germany; contains 1.5 mM $MgCl_2$, Tris-HCl, KCl and $(NH_4)_2SO_4$ pH 8.7). Enzyme activation and initial denaturation was performed at 94° C. for 15 min, followed by 45 amplification cycles (94° C. for 20 sec, 56° C. for 30 sec and 72° C. for 60 sec) and a final extension at 72° C. for 3 min.

RNA Transcription and RNase T1 Cleavage

Following PCR amplification, 2.4 µl of the PCR product was used in a 6 µl transcription reaction containing 10 units of T7 (or SP6) RNA polymerase (Epicentre) and 0.5 mM of each NTP in 1× transcription buffer (containing 6 mM $MgCl_2$, 10 mM DTT, 10 mM NaCl, 10 mM Spermidine and 40 mM Tris.Cl pH 7.9 at 20° C.). When transcription was carried out using Me-UTP or Me-CTP, UTP or CTP was completely replaced by modified methyl nucleotide. The transcription reactions were incubated at 37° C. for 2 h. After the transcription reactions were performed, 20 units of RNase T1 was added and the reaction mixture was incubated for 30 min at 30° C. Incubation at 30° C. was found to force the cleavage reaction towards the 3'-phosphate group and eliminated complexity generated by multiple mass signals for each given parent fragment in the mass spectrum.

An alternative approach is to use different RNA endonucleases to generate base-specific fragments. For example, the in vitro transcript can be completely digested with either RNase U2 at every A-position, RNase PhyM at every A and U position, or RNase A at every C and U position.

Sample Conditioning and Mass Spectrometry

Following transcription and cleavage, each sample was diluted by adding 21 µl $H_2O$. Conditioning of the phosphate backbone was achieved with 6 mg SpectroCLEAN™ cation exchange resin (ion exchange resin loaded with ammonium ion; Sequenom, USA). Next, 16 nl of the resulting solution was robotically dispensed onto a silicon chip (Spectro-CHIP™, Sequenom). All mass spectra were recorded with a Biflex III mass spectrometer (Bruker Daltonik, Germany). Positive ions were analyzed and ~50 single-shot spectra were accumulated. All samples were analyzed in linear time-of-flight mode using delayed ion extraction and a total acceleration voltage of 20 kV.

In an alternate method, instead of carrying out the amplification, transcription and digestion reactions in a single tube (homogeneous approach), the transcript can be isolated by hybridization onto an immobilized oligonucleotide that is complementary to the 3'-end of the transcript, e.g., an immobilized oligonucleotide containing a T7 or SP6 promotor. The isolated transcripts can then be digested with RNAse under MALDI-MS compatible conditions.

Results and Discussion

RNase T1 cleavage was driven to completion. Reaction conditions with a sufficient RNase concentration were optimized to avoid even low amounts of denaturing reagents, such as urea or formamide, which disturb analyte/matrix crystallization. One advantage of the presented homogeneous approach over a limited/incomplete digestion is that it can be extended to template regions of 500 nt or more, without signal loss in a higher mass range (>12000 Da). In complete digests, the highest mass fragment is sequence dependent, as determined by the largest distance between two G-positions, but the highest mass fragment is independent of the length of the RNA transcript.

Since homogenous assay formats do not apply any washing or removal of liquids, all of the above mentioned reagents and reagent components have an influence on the downstream MALDI analysis and its evaluation. Best performance was obtained with 5 µl PCR set-ups. This provides enough volume for two transcription reactions analyzing the forward and reverse strands. Sufficient PCR product yield and quality is achieved with 5 ng genomic DNA and 1 pmol of each required primer. An increase of DNA concentration resulted in only slightly higher yields. Increased primer concentration led in some cases to a significant generation of primer dimers. These reaction conditions could be applied to a wide range of target regions. In addition, the subsequent RNA transcription compensates for any variations in PCR product yield. The total volume of each RNA transcription and cleavage reaction was minimized without loss in data quality of individual mass spectra, i.e. signal to noise ratio of the fragment signals and the mass accuracy of the fragment signals were not diminished. Reproducible in vitro transcript yields were obtained by using 8 units of wt T7 RNA or SP6 RNA polymerase for a 6 µl reaction independent of the sequence of the PCR-amplified target region. Reproducibility testing and high-throughput analysis in 384 MTP format can be carried out using automated liquid handling devices.

RNase cleavage reactions at 37° C. or higher temperatures almost always generated a 1:3 mixture of 3'-cyclic phosphates and 3'-phosphates, whereas incubation at 30° C. was found to force the cleavage reaction towards 3'-phosphate groups. This eliminated complications by multiple signals for each given fragment in the mass spectra. In addition to the cleavage conditions, the ribonucleoside triphosphate concentration, transcription buffer composition and the amount of RNA polymerase were found to result in a reproducible, homogeneous RNA-based cleavage assay.

Miniaturized MALDI sample preparation with nanodispensing devices, which transfer the sample onto a chip array, represents an improvement over the standard 3-HPA macro preparation. Non-homogeneous analyte distribution in the MALDI sample (hot spot formation), which is almost always observed in 3-HPA macro preparations and hampers automated MALDI measurement, was largely suppressed by the miniaturized and homogeneous sample crystallization on the chip array. Also, sample portioning representing either only the low or the high mass window of the full spectrum of analyte masses was not observed. Further, the acquisition time for the automatic mass spectrometry measurement could be reduced to 5 seconds for any single sample.

Good sample crystallization on the silicon chip (Spectro-CHIP™) was achieved with a final dilution of the sample. Without dilution, buffer ingredients and detergent inhibited the crystallization process of the MALDI sample, resulting in no fragment signals detected in the MALDI-TOF spectra. Sample dilution and addition of ion-exchange resin to the final solution proved sufficient to condition the phosphate backbone of nucleic acid fragments, permitting efficient combination of the homogeneous fragmentation assay with chip array based MALDI-TOF MS analysis.

Representative fragmentation spectra demonstrated that all observed fragments possess 5'-OH and 3'-phosphate groups, and no fragments were observed that had 2',3'-cyclic phosphate groups, a stable intermediate under limited cleavage conditions. This permitted all major signals in the spectrum to be unambiguously assigned to expected fragments. Thus, following the described protocol, the method, provides highly reproducible and accurate results.

A limitation of an RNA-based fragmentation approach is caused by the small mass difference between U and C (1 Da). In some cases, two RNA fragments with identical length and differing by only one or a few U or C residues can not be separable with the current resolution of the linear MALDI-TOF instrument. To avoid this instrument related limitation, an alternative method can be used where a pyrimidine residue of one nucleotide is completely replaced by a chemically modified base during the transcription reaction. Either UTP or CTP can be replaced by the respective 5-Me-modified ribonucleotide analogue without a loss in transcription yield, increasing the mass of the corresponding nucleotide by 14 Da.

Another advantage of the mass modification method derives from the fact, that without any previous sequence information, the A-C-U-composition of any RNase T1 fragment can be calculated. Three different RNase T1 cleavage reactions can be separately carried out on nucleic acids containing: (a) CTP, UTP (b) 5-Me CTP, UTP and (c) CTP, 5-Me UTP. For any RNA-fragment, the mass difference between a given fragment of reaction (a) and (b) and the difference between reaction (a) and (c) can be used to calculate the number of U residues and C residues in the fragment. Since each fragment, except for the last fragment, contains only one G, the number of A residues also can be derived.

For partial base-specific cleavage, a modified or non-natural nucleotide that is not cleaved by the base-specific RNAse is added to the transcription reaction mix in a ratio that determines the number of cleavage sites that are cleaved. An exemplary protocol is provided below:

PCR Primer and Amplicon Sequence

```
Forward primer (SEQ ID NO. 6):
5'CAGTAATACGACTCACTATAGGGAGAAGGCTCCCCAGCAAGACGGAC
TT-3'

Reverse primer (SEQ ID NO. 7):
5'-AGGAAGAGAGCGCCTCGGCAAGTACAC-3'

Amplicon (SEQ ID NO. 8):
5'-GGGAGAAGGC TCCCCAGCAA GACGGACTTG TTCAAAAACA

TCATGAACTT CATAGACATT GTGGCCATCA TTCCTTATTT

CATCACGCTG GGCACCGAGA TAGCTGAGCA GGAAGGAAAC

CAGAAGGGCG AGCAGGCCAC CTCCCTGGCC ATCCTCAGGG

TCATCCGCTT GGTAAGGGTT TTTAGAATCT TCAAGCTCTC

CCGCCACTCT AAGGGCCTCC AGATCCTGGG CCAGACCCTC

AAAGCTAGTA TGAGAGAGCT AGGGCTGCTC ATCTTTTTCC

TCTTCATCGG GGTCATCCTG TTTTCTAGTG CAGTGTACTT

TGCCGAGGCG CTCTCTTCCT-3'
```

RNA Transcription and RNas Cleavag

Each reaction requires 2 µl of transcription mix and 2 µl of the amplified DNA sample. For a T-specific cleavage, the transcription mix contains 40 mM Tris-acetate pH 8, 40 mM potassium acetate, 10 mM magnesium acetate, 8 mM spermidine, 1 mM each of ATP, GTP and UTP, 2.5 mM of dCTP, 5 mM of DTT and 20 units of T7 R&D polymerase (Epicentre). For T-specific partial cleavage, a 4:1 ratio of dTTP to UTP is used. Transcription reactions were performed at 37° C. for 2 hours. Following transcription, 2 µl of RNase A (0.5 µg) was added to each transcription reaction. The RNase cleavage reactions were carried out at 37° C. for 1 hour.

Sample Conditioning and MALDI-TOF MS Analysis

Following RNase cleavage, each reaction mixture was diluted within a tube or 384-well plate by adding 20 µl of ddH$_2$O. Conditioning of the phosphate backbone was achieved by addition 6 mg of cation exchange resin (SpectroCLEAN™, Sequenom) to each well, rotation for 5 min and centrifugation for 5 min at 640×g (2000 rpm, centrifuge IEC Centra CL3R, rotor CAT.244). Following centrifugation, 15 nl of sample was transferred to a SpectroCHIP™ using a piezoelectric pipette. Samples were analyzed on a Biflex linear TOF mass spectrometer (Bruker Daltonics, Bremen).

Example 2

Base-Specific Cleavage of DNA

The following example describes a method for fragmenting a target nucleic acid according to the presence of a U residue in the nucleic acid, which is accomplished by digestion with the enzyme Uracil DNA glycosylase and phosphate backbone cleavage using NH$_3$. The fragmentation method provided herein can be used to generate base-specifically cleaved fragments of a target DNA, which can then be analyzed according to the methods provided herein to identify the sequence variations in the target DNA relative to a reference DNA.

The DNA region of interest was amplified using PCR in the presence of dUTP instead of dTTP. The target region was amplified using a 50 µl PCR reaction containing 25 ng of genomic DNA, 1 unit of HotStarTaq DNA Polymerase (Qiagen), 0.2 mM each of dATP, dCTP and dGTP and 0.6 mM of dUTP in 1× HotStarTaq PCR buffer. PCR primers were used in asymmetric ratios of 5 pmol biotinylated primer and 15 pmol of non-biotinylated primer. The temperature profile program included 15 min of enzyme activation at 94° C., followed by 45 amplification cycles (95° C. for 30 sec, 56° C. for 30 sec and 72° C. for 30 sec), followed by a final extension at 72° C. for 5 min.

For microsatellite analysis, the temperature profile was changed to a touchdown program with a starting annealing temperature of 62° C. and a 2° C. decrease in annealing temperature every two cycles until reaching a final annealing temperature of 56° C. This temperature profile proved to be more generally applicable for amplification of microsatellite loci.

To the crude PCR product, 50 µg of prewashed paramagnetic streptavidin beads (Dynal) in 45 µl of 2× B/W buffer (10 mM Tris-HCl, pH 7.5, 1 mM EDTA, 2 M NaCl) were added and incubated at room temperature for 20 min. The streptavidin beads carrying the immobilized PCR product were then incubated with 0.1 M NaOH for 5 min at room temperature. After removal of the supernatant containing the non-biotinylated PCR strand, the beads were washed three times with 10 mM Tris-HCl pH 7.8.

The beads carrying single stranded biotinylated PCR product were redissolved in 12 µl UDG buffer (60 mM Tris-HCl, pH 7.8, 1 mM EDTA), 2 units of Uracil DNA Glycosylase (MBI Fermentas) was added, and the mixture was incubated for 45 min at 37° C. Following the cleavage reaction, the beads were washed twice with 10 mM Tris-HCl pH 7.8 and one time with ddH$_2$O. The beads were then resuspended in 12 µl aqueous NH$_3$, incubated at 60° C. for 10 min, and cooled to 4° C. The supernatant containing the eluted strands was transferred to a new tube and then heated to 95° C. for 10 min, followed by incubation at 80° C. for 11 min with an open lid to evaporate the ammonia.

An exemplary protocol for partial cleavage is provided below:

PCR Primer and Amplicon Sequence

```
Forward primer (SEQ ID NO. 9):
5'-Bio CCCAGTCACGACGTTGTAAAACG-3'
```

-continued

```
Reverse Primer (SEQ ID NO. 10):
5'-AGCGGATAACAATTTCACACAGG-3'

Amplicon (SEQ ID NO. 11):
5'-CCCAGTCACG ACGTTGTAAA ACGTCCAGGG AGGACTCACC

ATGGGCATTT GATTGCAGAG CAGCTCCGAG TCCATCCAGA

GCTTCCTGCA GTCACCTGTG TGAAATTGTT ATCCGCT-3'
```

To achieve partial cleavage, 75 μg of Streptavidin Beads (Dynal, Oslo) were prewashed 2 times in 50 μl of 1× B/W buffer and resuspended in 45 μl of 2× B/W buffer (according to recommendation by manufacturer). Biotinylated PCR product was immobilized by adding the 50 μl PCR reaction to the resuspended Streptavidin Beads and incubation at room temperature for 20 min. The streptavidin beads carrying the immobilized PCR product were then incubated with 0.1 M NaOH for 5 min at room temperature to denature the double-stranded PCR product. After removal of the supernatant containing the non-biotinylated PCR strand, the beads were washed three times with 10 mM Tris-HCl pH 7.8 to neutralize the pH.

The beads were resuspended in 10 μl of UDG buffer (60 mM Tris-HCl pH 7.8, 1 mM EDTA pH 7.9), 2 units of Uracil DNA Glycosylase were added (MBI Fermentas) and the mixture was incubated at 37° C. for 45 min. Following the reaction, the beads were washed twice with 25 μl of 10 mM Tris-HCl pH 8, and once with 10 μl ddH$_2$O. The biotinylated strand was eluted by adding 12 μl of 500 mM NH$_4$OH and incubating at 60° C. for 10 min. After the 10 min incubation, the supernatant was collected into a fresh microtiter plate or tube to cleave the phosphate at abasic sites, followed by incubation at 95° C. for 10 minutes with a closed lid. To evaporate the ammonia, an incubation at 80° C. for 11 minutes is performed with an open lid.

Mass Spectrometric Analysis

Following DNA cleavage, 15 nl of sample were transferred onto a SpectroCHIP™ (Sequenom) using a piezoelectric pipette. Analysis was performed on a Bruker Bilex mass spectrometer (Bruker Daltonics, Bremen).

Example 3

A. SNP Discovery by Base-Specific Fragmentation of Amplified DNA

Base-specifically cleaved fragments of target sequences containing SNPs can be analyzed by the methods provided herein to detect known SNPs or discover unknown SNPs. High-throughput base-specific fragmentation followed by mass spectrometric analysis may be performed according to Rodi et al., *BioTechniques*, 32:S62-S69 (2002) (incorporated by reference herein), using systems such as the system denoted by the trademark MassARRAY™. MassARRAY™ relies on mass spectral analysis combined with the miniaturized array and MALDI-TOF (Matrix-Assisted Laser Desorption Ionization-Time of Flight) mass spectrometry to deliver results rapidly. The fragment signals generated according to the methods provided herein and in Rodi et al., *BioTechniques*, 32:S62-S69 (2002) can be analyzed according to the methods provided herein.

In base-specific fragmentation, a single-stranded copy of the target sequence is created and in four separate reactions fragmented to completion at positions corresponding to each of the four bases. This reduces the nucleic acid to a collection of sets of oligonucleotides, which are easily resolvable with the precision, accuracy, and resolution of the MALDI-TOF MS. Using a reference sequence allows one to definitively identify each resulting peak. Changes in sequence have profound and easily discernible affects on the pattern of peaks produced. This is illustrated in the following sequence:

```
XXXACTGXXXC/AXXXTGACXXX        (SEQ ID NO. 12)
```

In this example an A/C transversion is shown. Suppose the known (reference) sequence were the A-containing sequence; then one would expect that an A-specific cleavage of the displayed sequence would produce the two fragments shown, a 7-mer and a 6-mer (ignoring the end fragments). Now consider the result if a sample contained a C at the second A position. There would be only two A residues, and the cuts would produce the single large fragment shown, a 13-mer; the 7-mer and 6-mer would disappear (or in the case of a heterozygote, be diminished in intensity). The C-specific cleavage would, of course, produce the converse result, of a 13-mer for the A allele and a 6-mer plus a 7-mer for the C allele. Even the T-specific and G-specific cleavages yield discernible changes, since the C-allele is 24 Da less massive than the A-allele, a peak shift that is easily detected in the low mass portion of the mass spectrum. Any one of these reactions would be sufficient to detect this polymorphism, but taken together the precise location can be determined, since in most instances there is only one way to reconcile all four peak patterns.

The single-stranded nucleic acid is produced by transcription, a very reliable, economical, and process-friendly method. A T7 RNA polymerase promoter can be attached to either end of an amplicon during DNA amplification using a three-primer system (see Rodi et al., *BioTechniques*, 32:S62-S69 (2002)). Target-specific amplification primers are used, each with a slightly different sequence tag at the 5' end. By including a universal forward T7 primer in the reaction amplicons are created that produce + transcripts; by substituting a universal reverse T7 primer into the reaction, amplicons are created that produce − transcripts. In high-throughput mode, it is recommended to simply run two + strand reactions and two − strand reactions rather than distribute transcripts after they are produced. The two + strands are fragmented using an RNase reaction specific for C residues in one well and a second reaction specific for U residues in the other well. G-specific and A-specific cleavages are deduced by simply running the C-specific and U-specific reactions, respectively, on the − strands.

One of the great advantages of the fragmentation approach for discovery of genetic variation is the clarity of the signal produced. This permits targeted discovery using amplicons (rather than clones) and fully automated interpretation of the results. An example of this is shown in the CETP gene (see Rodi et al., *BioTechniques*, 32:S62-S69 (2002)). A 500 bp amplicon from intron 10 of the CETP gene (SEQ ID NO. 13) was produced from each of 12 individuals, transcribed, and subjected to T-specific fragmentation. The partial spectrum corresponded precisely to the predicted peak pattern based on the Ensembl sequence; all expected peaks were present and no unexpected peaks were seen. Two of the twelve individuals showed different patterns, showing an unexpected peak at 3159 Da; furthermore, the peak at 2830.7 Da had a significantly reduced signal intensity. Since no predicted peaks were absent, this is consistent with one of the homologues of this individual having a nucleotide substitution at a T residue, thereby rendering it resistant to cleavage and resulting in the new signal at the higher mass. The second individual had the same unexpected peak at 3159 Da, but its relative intensity was greater and the peak at 2830.7 Da was completely absent; this individual is therefore homozygous for the here-to-fore unknown SNP. The clarity, accuracy and rapidity with which the fragment signals are generated according to the aforementioned fragmentation method renders them among the preferred signals for analysis according to the methods provided herein.

B. Evaluation of SNP Discovery by Base-Specific Fragmentation

The methods provided herein for analysis of a reduced set of sequence variation candidates ("automated" method) were implemented in C++. Included in the implementation was the refined SNP scoring scheme and the iterative SNP selection process according to the methods provided herein. In some instances, as provided below, analyses according to the algorithms implemented in C++ were compared to manual assembly of the list of candidate SNPs. Manual assembly was performed by examining the consistency among the complementary cleavage reactions and/or the recurrence of an indicative fragment in the sample set, then simulating the variant mass spectrum or other indicator of mass, such as mobility in the case of gel electrophoresis, for every possible sequence change (rather than obtaining a reduced set of sequence variation candidates according to the methods provided herein) of a reference sequence that does not contain the sequence variation. In the manual approach, each simulated variant spectrum corresponding to a particular sequence variation or set of sequence variations is then matched against the actual variant mass spectrum to determine the most likely sequence change or changes that resulted in the variant spectrum.

Two sets of samples, a first set of 10 amplicons (Amplicon 1-Amplicon 10; SEQ ID NOS. 45-54) and a second set of 30 amplicons (Amplicon 2.1-2.30; SEQ ID NOS. 55-84) of 500 bp average lengths derived from various regions of the human genome, were analyzed. For each amplicon, DNA samples from 12 Caucasian individuals (Dausset et al., *Genomics*, 6(3):575-577 (1990)) were analyzed and compared against a corresponding reference sequence for the presence of SNPs within the region spanned by the amplicon sequence.

Method

Base-specific cleavage was performed employing RNA-transcription with T7 RNA polymerase followed by RNAse cleavage as provided herein. All PCR primers were tagged with a T7 promoter at their 5' end. Two sets of PCR primers, having sequences identical or complementary to 18-22 bases at the 5' and 3' ends of the 40 amplicons whose sequences are provided in the sequence listing as SEQ ID NOS. 45-84, were ordered for each amplicon to allow for transcription of either sense or anti-sense strand. RNase A was used to obtain T-specific and C-specific cleavage using sense transcripts and the equivalent of A-specific and G-specific cleavage using anti-sense transcripts (the activity of RNase A toward C (T) residues was blocked by incorporation of dCTP (dTTP) into the transcripts, thus rendering the RNase A specific for either U or C residues). In this way, the equivalent of all four base-specific cleavages was analyzed.

5 µl PCR reactions in 384 well plates were set-up. Uniform PCR conditions were employed as provided herein. Following PCR, transcription mix was added into each well of the microtiter plate and transcription was performed for 2 hours at 37° C. Subsequent to transcription, RNase A was added into each well and cleavage proceeded for 60 minutes at 37°

C. Conditioning of RNA fragments for MALDI-TOF MS analysis was performed by adding 6 mg of SpectroCLEAN™ to each well.

For MALDI-TOF MS analysis, 10 nl of analyte was automatically dispensed onto a 384 array chip with a pintool device. All post-PCR pipetting steps were performed using a Beckman Multimek pipettor.

Results

SNPs were identified by automated analysis generating a reduced set of sequence variation candidates, simulation of the reduced set and scoring according to the methods provided herein. Results were further verified by manual analysis of additional and missing signals reported in the software. All identified SNPs were validated by a subsequent chain terminating primer extension reaction. In cases where the base-specific reaction could not exactly locate the position of the SNP, the primer extension reaction was also used to locate the SNP.

A. Set 1: 10 amplicons

The following Table provides the SNPs (base change and position in the amplicon sequence) identified in the first set of 10 amplicons.

| Amplicon | Identified SNP | SEQ ID NO. |
| --- | --- | --- |
| 1 | C/T, @123 | 45 |
| 2 | T/G, @179<br>C/T, @317 | 46 |
| 3 | G/A, @285 | 47 |
| 4 | A/G, @131 | 48 |
| 5 | G/A, @50<br>T/C, @111<br>C/T, @133 or 135<br>C/T, @185<br>T/G, @198<br>C/A, @253*<br>T/C, @359* | 49 |
| 6 | C/G, @131 | 50 |
| 7 | T/A, @236 | 51 |
| 8 | C/G, @84<br>T/C, @269 | 52 |
| 9 | C/A, @136<br>G/A, @383 | 53 |
| 10 | G/C, @76 | 54 |

Of the above 19 SNPs that were identified by the automated method provided herein, only 2 (marked with *) were determined to be false positives that were not detected by the confirmatory primer extension reactions. Moreover, the two false positives were reported with very low confidence by the software.

B. Set 2: 30 amplicons

The SNPs (base change and position in the amplicon sequence) were similarly identified in the second set of 30 amplicons. In addition, the SNPs identified by automation generating and analyzing a reduced set of sequence variation candidates according to the methods provided herein were compared to the SNPs that were identified by a manual examination and analysis (construction, simulation and scoring of all possible sequence variation candidates) of the cleavage patterns obtained by the four complementary base-specific cleavage reactions. All SNPs, whether detected by manual or automated analysis, were verified as being true positives or false positives by chain terminating primer extension reactions.

Thirty 'disjoint' amplicons (non-overlapping sub-regions of DNA amplified by PCR) of lengths 328 to 790 base pairs were amplified from various regions on Human Chromosome 22 (Dunham et al., *Nature*, 402(6761):489-495 (1999)), the average length of an amplicon being 433 base pairs. In total, 11793 base pairs were analyzed. For the mass spectrometric analysis, four base-specific cleavage reactions were performed using RNAse A and measured by mass spectrometry independently.

Analyzing the mass spectrometry data manually, 50 SNPs were discovered and verified by chain terminating primer extension. For 6 of these 50 SNPs, the exact position could not be determined from the cleavage mass spectrometry data. Manual analysis of the mass spectrometry data was very time consuming, and it took several weeks to complete the analysis. In addition, one SNP was found using the electrophoresis data that was missed in the manual analysis of the mass spectrometry data.

In total, 51 SNPs were discovered by manual analysis of mass spectrometry data or electrophoresis data (on average, one SNP every 231 base pairs). This indicates that a desirable threshold to be reached in the case of SNP discovery applications is a sequence variation order k of usually, although not necessarily, 1 or 2, where the order 2 covers SNPs that are in closer vicinity with respect to each other. In cases of mutation discovery or resequencing, the value of k is usually, although not necessarily, 3 or 4 or higher because multiple base changes in close proximity to each other are more likely to be observed.

The cleavage mass spectrometry data was then analyzed by implementing the automated methods provided herein. All of the 51 SNPs were included in the 22,447 potential reduced set of sequence variation candidates constructed using the algorithm implemented according to the methods provided herein. The analysis was performed for every sample individually, so that 1871 sequence variations per sample were scored on average. Of the 53 SNPs identified by the automated method, 7 were verified as false positives and 46 were verified as true positives. Again, for 6 of the 46 true positive SNPs, the exact position could not be determined.

While the automated method identified 5 fewer SNPs than the manual method, it is noted that this level of sensitivity and specificity was achieved using the default scoring scheme and threshold of the analysis package, rather than tailoring the parameters of the package to the present example. Moreover, in contrast to the time required to complete the manual analysis, which was several weeks, the automated method, which constructed and scored a reduced set of 22,447 sequence variation candidates compared to manual simulation of a total set of 1132128 sequence variation candidates, provided a significant reduction in the runtime required to process the data for analysis, which in turn reduced the total analysis time.

Runtime measurements corresponding to sequence variation order k=1, 2 or 3, were performed on a single processor desktop computer using a 1.0 GHz Pentium III processor. For k=1, the automated runtime was 1.5 s compared to a manual runtime of 62.6 s. As the sequence variation order increases, the difference in runtimes greatly increases. Thus, for k=2, the automated runtime was 32.2 s, versus a manual runtime of 91.9 min. For k=3, the automated runtime was 467 s, versus a manual runtime of 57 h. Thus, by using the algorithm implemented according to the methods provided herein, the sequence variation analysis for even higher order variations (k=3) can be performed in 0.33 seconds per analyzed mass spectrum and is therefore well suited for real time analysis of mass spectrometry data.

Example 4

Bacterial Typing by Base-Specific Fragmentation

This example provides a method for base-specific fragmentation of bacterial strains. The fragments produced according to the fragmentation methods provided herein and in von Wintzingerode et al. (*Proc. Natl. Acad. Sci. U.S.A.* 99(10):7039-7044 (2002)), incorporated by reference herein, can be analyzed according to the methods provided herein to identify target bacterial strains.

Materials and Methods

Bacterial Strains

Twelve reference strains ("type" strains) of *Mycobacterium* species, provided by the German Collection of Microorganisms and Cell Cultures (DSMZ, Braunschweig, Germany) and Institute for Standardization and Documentation in Medical Laboratory reg. ass. (Instand e.V., Düsseldorf, Germany), and twenty-four clinical isolates of mycobacteria were used in this study. The mycobacteria were grown in liquid medium (MGIT liquid medium; Becton Dickinson Europe, France) with enrichment supplement (MGIT system oleic acid-albumin-dextrose-citric acid) and antimicrobial supplement (MGIT system PANTA (polymyxin B, nalidixic acid, trimethoprim, and azlocillin)). The mycobacteria were cultured at 37° C., with the exception of *Mycobacterium marinum*, which was cultured at 30° C. When bacterial growth was indicated, mycobacteria were concentrated in 0.5 ml broth by centrifugation at 3300×g for 20 min.

DNA Extraction

DNA was extracted using a commercially available kit (Respiratory Specimen Preparation Kit, AMPLICOR: Roche Molecular Systems, Inc., Branchburg, N.J., USA). Briefly, 100 µl of resuspended mycobacterial pellet was transferred into a 1.5 ml polypropylene tube, washed with washing solution (500 µl) provided by the kit, and centrifuged (14,000×g) for 10 min. The supernatant was discarded and the bacterial pellet was resuspended in lysis reagent (100 µl). After incubation in a 60° C. heating-block for 45 min, the lysate was neutralized with the provided neutralizing reagent (100 µl) and the resulting DNA solution was stored at 4° C.

Identification by PCR and Sequencing.

Full-length 16S rRNA genes from the twelve *Mycobacterium* reference strains (see SEQ ID NOs. 14-25) were analyzed as described (see von Wintzingerode et al., *Appl. Environ. Microbiol.* 65:283-286 (1999)). Briefly, 16S rDNA was PCR amplified using eubacterial primers

TPU1 (AGA GTT TGA TCM TGG CTC AG, (SEQ ID NO. 39)

corresponding to *E. coli* positions 8-27) and RTU8 (AAG GAG GTG ATC CAK CCR CA (SEQ ID NO. 40), corresponding to *E. coli* positions 1541-1522 (see SEQ ID NO. 29 for the 16S rRNA gene sequence from *E. coli*)). PCR-products were ligated with the vector pCR2.1 (TA cloning kit, Invitrogen, de Schelp, Netherlands) and transformed into *E. coli* according to the manufacturer's instructions. Recombinant plasmid DNA was purified using the GFX Plasmid Preparation Kit (Amersham Pharmacia, Freiburg, Germany), and used directly for cycle-sequencing with the Thermosequenase Fluorescent Labeled Primer cycle sequencing kit (Amersham Pharmacia, Freiburg, Germany). Sequencing reactions were analyzed on a LICOR 4000 L automated DNA sequencer (MWG-Biotech, Ebersberg, Germany) and alignments were generated with ARB-software (http://www.arb-home.de/). Full-length 16S rRNA gene sequences of the twelve reference strains were deposited in the EMBL nucleotide sequence database (see EMBL Accession Nos. AJ536031-AJ536042) and are provided in the sequence listing as SEQ ID NOs. 14-25.

Identification of mycobacteria from clinical sources was performed by PCR amplification of partial 16S rDNA and direct sequencing focusing on hypervariable regions A and B corresponding to E. coli 16S rDNA (SEQ ID NO. 29) positions 129 to 267 and 430 to 500, respectively, according to the protocol of Springer et al. (*J. Clin. Microbiol.* 34:296-303 (1996)). The resulting sequences were compared with those of all 16S rRNA entries in the EMBL and GenBank databases by using the programs BLASTN and FASTA of the Husar program package (version 4.0; Heidelberg Unix Sequence Analysis Resources, DKFZ, Heidelberg, Germany). Clinical isolates were identified to the species level based upon sequence identity in both hypervariable regions with a database entry, and a total sequence identity of >99%.

Identification by PCR and MALDI-TOF.

PCR and MALDI-TOF analyses were done in triplicate for every mycobacterial strain. PCR amplification mixture contained PCR buffer (Tris-HCl, KCl, $(NH_4)_2SO_4$, $MgCl_2$ (pH 8.7)) with a final $MgCl_2$ concentration of 2.5 mM, 200 µM (each) deoxynucleoside triphosphates, 1 U of HotStarTaq (QIAGEN GmbH, Hilden, Germany), 10 pmol of primer Myko 109-T7 (5'-gtaatacgactcactataggg ACG GGT GAG TAA CAC GT-3' (SEQ ID NO. 41); corresponding to E. coli 16S rRNA from positions 105 to 121), 10 pmol of primer R259-SP6 (5'-atttaggtgacactataga TTT CAC GAA CAA CGC GAC AA-3' (SEQ ID NO. 42); corresponding to E. coli 16S rRNA from positions 609 to 590) and 5 µl DNA in a total volume of 50 µl. PCR amplification was performed using a thermal cycler (Goldblock; Biometra, Göttingen, Germany) for 40 cycles of denaturation (1 min, 95° C.), annealing (1 min, 58° C.), and extension (1 min 30 sec, 72° C.), after an initial step of HotStarTaq activation (15 min, 95° C.). Amplification was verified by agarose gel electrophoresis.

RNA Transcription and RNase T1 Cleavage

Forward strand RNA transcription was performed by incubation of 2.4 µl PCR product, 10 U of T7 (or SP6) RNA polymerase (Epicentre), 0.5 mM each of ATP, GTP, UTP, and 5-Methyl ribo-CTP in 1× transcription buffer (6 mM $MgCl_2$, 10 mM DTT, 10 mM NaCl, 10 mM Spermidine, 40 mM TrisCl (pH 7.9) at 20° C.) for 2 h at 37° C. Ribo-CTP was replaced by the chemically modified analog 5-Methyl ribo-CTP (Trilink, USA) to generate a mass difference between U and C. After transcription was performed, complete G-specific cleavage was achieved by adding 20 U of RNase T1 and 1 U shrimp alkaline phosphatase (SAP) and incubating at 30° C. for 30 min.

Sample Conditioning and MALDI-TOF MS Analysis.

Each sample was diluted by adding 21 µl of water. Conditioning of the phosphate backbone was achieved by adding 6 mg SpectroCLEAN™ resin (cation ion exchange resin loaded with ammonium ion; Sequenom, USA). After conditioning, 10 nl of sample was automatically transferred onto a SpectroCHIP™ silicon chip (Sequenom, USA) preloaded with 3-HPA matrix using a pintool device. All mass spectra were recorded using a Biflex III mass spectrometer (Bruker Daltonik, Bremen, Germany). Exclusively positively charged ions were analyzed and approximately 50 single-shot spectra were accumulated per sample. All samples were analyzed in linear time-of-flight mode using delayed ion extraction and a total acceleration voltage of 20 kV. Spectrum processing and peak assignment was performed using the software package XMASS 5.0, provided by the manufacturer (Bruker Daltonik) or in-house software for baseline correction, peak identification and calibration to identify strains of clinical isolates by comparing their detected mass signal pattern with the reference sequence derived in silico pattern of the type strains and to in silico mass patterns of published 16S rDNA sequences.

Results

*Mycobacterium* Isolates

An approximately 500 bp region of the 16S rRNA gene corresponding to E. coli 16S rDNA positions 105-609 (SEQ ID NO. 29) was PCR-amplified from all type strains and clinical isolates. RNA transcription and base-specific cleavage resulted in unique MALDI-TOF mass spectra for all tested type strains.

A representative mass spectrum of *Mycobacterium tuberculosis* H37Rv (SEQ ID NO. 24) was assessed. The main cleavage products were assigned peak numbers of 1-27 and their nucleic acid composition and exact location within the uncleaved PCR amplicon was determined. Reference mass signals have been calculated from the reference sequence by in silico cleavage at all positions of guanine and correlated to mass signals detected by MALDI-TOF MS. Calculated fragments with a mass difference smaller than 4 Da could not be separated by the linear, axial MALDI-TOF MS. Corresponding detected cleavage products were assessed as one fragment only (peak nos. 2, 3, 4, 8, 9, 11, 12, 18).

Mass signals were classified either "MAIN" cleavage products (before the 3'-end of the amplicon) or "LAST" cleavage products (at the 3' end of the amplicon). Mass signals number 22, 24 and 25 were classified "LAST", because they represented cleavage products at the 3'-end of the transcript (all at position 510), differing by the addition of one 5-Methyl-CTP (3' fragment +319.2 Da) or one ATP (3' fragment +329.2 Da), respectively. Non-templated addition of a nucleotide to the 3'-end of the RNA transcript reflected terminal transferase activity of T7-RNA polymerase, a feature well known for Taq DNA polymerases. The non-templated addition of nucleotides to the terminal fragments was included in the software-automated identification of fragments for all mycobacterial species to avoid misinterpretation.

Characteristic mass spectra of five representative mycobacterial type strains in a mass range between 1500 and 2600 Da were analyzed. *M. tuberculosis* (SEQ ID NO. 24), *M. avium* (SEQ ID NO. 15), *M. intracellulare* (SEQ ID NO. 19), *M. kansasii* (SEQ ID NO. 20) and *M. celatum* (SEQ ID NO. 16) were clearly differentiated by their unique mass spectra. *M. tuberculosis* was the only species lacking a fragment at 1828 Da. *M. celatum* showed a signal at 1884 Da not present within all other mass patterns. The spectrum of *M. kansasii* displayed no signal at 2180 Da. Mass spectra of *M. avium* and *M. intracellulare* differ from the other species by fragments at 2532 Da and 2157 Da, respectively.

In silico, discriminatory peak patterns of all mycobacterial species used in this study were compiled. The ranking was performed according to the number of missing and additional peaks as compared to the mass spectrum of *M. tuberculosis*. Only discriminatory peaks that were not present throughout all *Mycobacteria* species were included. *M. tuberculosis* could be clearly differentiated from other species on the basis of multiple additional or missing mass signals. *M. celatum* and *M. kansasii* were the closest species as compared to *M.*

*tuberculosis* showing one missing and three additional peaks or two missing and two additional peaks, respectively. *M. marinum* (SEQ ID NO. 24) and *M. scrofulaceum* (SEQ ID NO. 22) differed by only two fragments (2453.5 Da, 2795.8 Da). All calculated mass patterns were confirmed experimentally. A comparison of all mass spectra resulted in unambiguous identification of all *Mycobacteria* species.

In the case of the *M. xenopi* type strain DSM 43995, comparison of experimental and calculated mass patterns revealed an additional mass peak at 4408.8 Da in MALDI TOF analysis. Cloning of the respective *M. xenopi* 16S rDNA amplicon (SEQ ID NO. 25) and repeated sequencing of several plasmids resulted in the detection of three sequence variants differing in 1-2 base pairs at *E. coli* position 198 (T/C) and 434 (T/C). The sequence variation at *E. coli* position 198 is not detected in a G-specific cleavage reaction. The resulting dimeric fragments (50H-TG-3p and 50H-CG-3p) overlapped with cleavage products of the same composition originating from different positions in the amplicon. Base-specific cleavage of an approximately 500 bp amplicon statistically results in all possible combinations of dimers, represented multiple times. In addition, the mass range below 1000 Da can be affected by background noise signals caused by matrix molecules, a feature specific to the use of 3-hydroxypicolinic acid matrices (3-HPA) in matrix-assisted laser desorption/ionization time-of-flight mass spectrometry.

Sequence variation at *E. coli* position 434 (T/C) affects a 14 bp G-specific cleavage product. The nucleotide mass difference between a T (corresponding to U in cleaved RNA) and a C diminishes the mass of the expected fragment by 13 Da. The detection of both mass signals at 4408.8 Da and 4421.8 Da indicates that the analyzed amplicon of the type strain contains of a mixture of both sequence variants.

After establishing a database including the twelve mycobacterial type strains, twenty-four clinical isolates were analyzed automatically with MALDI-TOF mass spectrometry. G-specific cleavage of RNA-transcribed 16S rDNA amplification products and mass spectrometry led to unambiguous identification of twenty-one isolates. Of the twenty-one isolates, eight were identified as *M. tuberculosis* (SEQ ID NO. 24) and two isolates were identified from each of *M. avium* (SEQ ID NO. 15), *M. gordonae* (SEQ ID NO. 18), *M. intracellulare* (SEQ ID NO. 19) and *M. xenopi* (SEQ ID NO. 25). The remaining five isolates were identified as *M. chelonae* (SEQ ID NO. 85), *M. fortuitum* (SEQ ID NO. 17), *M. kansasii* (SEQ ID NO. 20), *M. marinum* (SEQ ID NO. 21) and *M. smegmatis* (SEQ ID NO. 23).

All isolates representing species from the type strain database were identified correctly in repeated experiments. Three clinical isolates representing *M. aurum* (MT1 323), *M. paraffinicum* (MT1 423) and *M. interjectum* (MT1 223) could not be identified after MALDI-TOF analysis of their RNA cleavage products. The database lacked the corresponding in silico mass pattern of all three species. An extension of the database with the species specific mass signal pattern calculated from published 16S rDNA sequences of *M. paraffinicum* (SEQ ID NO. 26), *M. interjectum* (SEQ ID NO. 27) and *M. aurum* (SEQ ID NO. 28) led to correct identification in all corresponding experiments.

*Bordetella* Strains

Three known *Bordetella* species, *Bordetella avium*, *Bordetella trematum*, and *Bordetella petrii* and six as yet uncultured bacteria of anaerobic, organochlorine-reducing microbial consortia (see von Wintzingerode et al. (*Proc. Natl. Acad. Sci. U.S.A.* 99(10):7039-7044 (2002)) also were analyzed by the methods described above by amplifying their variable 16S rRNA gene region (see SEQ ID NOs. 30-38) using eubacterial primers TPU1 (SEQ ID NO. 39) and RTU8 (SEQ ID NO. 40). As described, the mass difference of 1 Da between ribo-CTP and ribo-UTP nucleotides was increased by replacement of either pyrimidine base with its 5 Me-analog, without detectable loss of transcription yield. G-specific cleavage with RNAse T1 produced a characteristic pattern of fragment masses, which was indicative of the individual 16S rRNA gene target sequences. All six as yet uncultured *Bordetella* strains were identified unambiguously and the results were concordant with those obtained by standard fluorescent dideoxy sequencing.

Example 5

Detection of Methylation Patterns by Base-Specific Fragmentation

The covalent addition of methyl groups to cytosine is primarily observed at CpG dinucleotides. These CpG islands are observed less frequently than other dinucleotides, and less frequently than would be expected for a random nucleic acid sequence. A high number of CpG dinucleotides is observed at the promoter region and at the 5' end of genes. Provided herein is an exemplary protocol for using fragmentation analysis to study methylation patterns in a target sequence. The fragments generated according to the exemplary protocol herein may be analyzed according to the methods provided herein for studying variations in the methylation pattern of a target sequence relative to a reference sequence.

Genomic DNA containing methylated cytosine can be treated with sodium bisulphite, where the non-methylated cytosine converts to uracil but methylated cytosine remains cytosine. After bisulphite treatment, the top and bottom strands are no longer complementary. This methylation dependent sequence variation can serve as a basis for analysing methylation patterns. Detection of methylation associated sequence variation using mass spectrometry can be accomplished by creating defined fragments, where methylation results in mass shift of affected fragments.

Detection of cytosine methylation was tested at the Igf2/H19 locus of chromosome 11.p15.5 (SEQ ID NO. 43). A sequence between H19 and Igf2 known as the imprinting control region (ICR) is completely methylated in sperm and completely unmethylated in oocytes. In adult blood samples, the IGF2/H19 region is methylated only on one parental allele. Igf2 is an essential fetal growth factor, and its misregulation plays a role in Beckwith-Wiedemann syndrome and Wilms Tumor. H19 is an enigmatic untranslated RNA whose function is still unknown. For Igf2/H19, the differentially methylated ICR is necessary for imprinted transcription of both genes.

Bisulphite treatment of genomic DNA was followed by PCR. Primers for PCR contained a transcription tag at the 5' end for T7 or SP6 polymerase. In some cases a transcription tag containing 6 bases (agaagg) is placed between polymerase tag and DNA binding site of the oligo. This improved the transcription reaction and helps suppress the effect of premature termination.

RNA transcription was done in a 384 well plate format. After adding the transcription mastermix to the PCR product, transcription was performed @37° C. for 2 h. Next, the cleavage enzyme mix was added to the transcription reaction. Afterwards an ion exchanger was added, and the reaction solution was spotted on a chip and analysed by MALDI-TOF MS.

RNA cleavage can be done with two different enzymes: Endoribonuclease RNase T1 and RNase A. Both act on single stranded RNA by cleaving the phosphodiester bond but differ in their target nucleotides. RNase T1 cleaves between 3'-guanylic residues and the 5'-hydroxy residues of flanking nucleotides. This reaction yields oligonucleotides with a terminal 3'-GMP. RNase A specifically attacks RNA at C and U residues. RNase A catalyzes cleavage between the 5'-ribose of a nucleotide and the phosphate group attached to the 3'-ribose of a flanking pyrimidine nucleotide.

After RNase treatment, SAP was added to the cleavage reaction to reduce the quantity of cyclic monophosphate side products.

A mutant polymerase T7 was used to incorporate either dCTP or dTTP into the transcript. This permitted base specific cleavage at U or C residues when dCTP or dTTP, respectively, was incorporated, and also circumvented the problem arising from the almost identical masses of rCTP and rTTP.

Therefore there are six theoretically possible cleavage schemes of one sequence:

|  | Forward primer T7 tagged | Reverse Primer T7 tagged |
|---|---|---|
| RNase T1 | G specific cleavage | G specific cleavage |
| RNase A; dCTP | T specific cleavage | T specific cleavage |
| RNase A; dTTP | C specific cleavage | C specific cleavage |

In one example, a bisulfite treated DNA Sequence like TAAAC$^{(5'me)}$GCAT will remain TAAACGTAT if methylated at the cytosine at the fifth position and will convert to TAAATGTAT if not methylated.

The transcription product of the M32053 target region is a 430 nucleotide long fragment containing both the ggg transcription start and a agaagg tag and the 421 nucleotide long transcription product. The number of resulting fragments after base specific cleavage depends on the cleavage scheme, the transcription direction and the methylation status.

Results

RNAse A Cleavage

Forward Transcript

Spectra of methylated samples were clearly distinguished from non-methylated samples. In all cases of CpG methylation a new fragment was created that could be assigned to methylation in those fragments. Five of those fragments contained two CpG sites and two signals were created by two fragments containing one CpG site each. In some cases it was not clearly differentiable which one of the CpG sites was responsible for the detected signal; in those cases, the absence of signals resulting from non methylated CpG islands helped to identify the methylation status.

Reverse Transcript

Methylated and non-methylated samples were clearly distinguishable. In contrast to the forward transcription, every methylation event resulted in a mass shift of the corresponding signal. Signal intensity was slightly better compared to the forward reaction.

RNAse T1 Cleavage

Signal intensity overall was lower than in RNAse A cleaved samples. The transcription results were best with wildtype T7 polymerase. Addition of SAP to the cleavage reaction as well as fitting in an agaagg tag into the primer did not improve efficiency.

Forward Transcript

In the forward reaction, methylated samples were clearly distinguished from non-methylated ones. The mass shifts of 13 d in the methylated samples were sometimes hard to detect in clusters of signals, because the peaks were close together.

Reverse Transcript

The reverse reaction was more complicated in the non-methylated samples compared to the other transcriptions. Because there was no cytosine in the forward strand, there was no guanosine in the reverse transcript, and, therefore, there was no recognition site for the enzyme to cut. Therefore, signal intensity was weak.

Methylation Pattern of IGF2/H19 Imprinted Region M32053

The methylation pattern of the m32053 region was clearly distinguished in methylated and non-methylated DNA. The analysed samples were either completely methylated or not methylated. Previous articles described complete segregation of methylated and non methylated DNA in germlines and also further stages of maturity. The DNA CpG site at position 470 was clearly typed methylated. The data also confirmed methylation of the CpNpG site at position 347.

Methylation Ratio

In order to determine methylation ratios in DNA samples different amounts of methylated and nonmethylated DNA were pooled. Determination of the plasmid DNA concentration was performed with Pico Green fluorescent assay.

The analysed samples had a rising concentration of methylated DNA. DNA pools containing 0%, 0.5%, 1%, 5%, 10%, 20% . . . 90%, 95%, 99%, 99.5% and 100% methylated DNA were analysed. RNAse A cleavage was performed in both transcription directions. There was no significant difference in accuracy or reliability comparing the forward and the reverse reaction. Peak area was measured to examine the methylation ratios of methylated vs. non methylated.

Methylation ratios were determined in a range from 10-90% methylated DNA with an accuracy of ±2%. The accuracy decreases in the high and in the low ranges of methylated DNA. In samples where the concentration of methylated DNA falls under 5%, the corresponding peak becomes difficult to resolve from background. Therefore, the detection limit was in between about 1-5% methylated DNA.

Genomic DNA

The analysis showed the methylated and the non-methylated clone in a 50/50 ratio. This indicates equal PCR amplification of methylated and non-methylated alleles in a genomic DNA.

Coverage and Redundancy

In theory, each methylated CpG can generate a specific fragment resulting in at least one indicative mass signal in the mass spectrum. Some of these signals might not be detectable because their masses fall in the high or low mass cut off. MALDI-TOF equipment can allow detection of cleavage products with a mass between 1000 to 11000 Da, equivalent to fragments about 3 to 35 nucleotides in length. Depending on the target nucleic acid sequence, one reaction alone can allow determation of the methylation status of, for example, around 75% of all CpG sites within the target nucleic acid. To obtain the information about all CpG sites, two to four reactions can be used, where the reactions can include C or T specific cleavage of the forward or reverse transcription products. This combination can permit base specific cleavage at every nucleotide on the forward strand, since C specific cleavage on the reverse strand is equivalent to G specific cleavage on the forward strand, and T specific cleavage on the reverse strand is equivalent to A specific cleavage on the forward strand. The combined information from two to four cleavage reactions can allow compilation of the exact methylation pattern. For the IGF2/H19 region, even two reactions were sufficient to obtain the methylation status for each CpG site. Using four reactions provided redundant information, where 92% of all CpG sites were represented by more than one signal. Thus, each methylation event was independently confirmed by one or more observations.

Methylation analysis using RNA fragmentation combined with MALDI-TOF MS detection is a successful technique offering the potential of high throughput analysis combined with the use of small amounts of poor quality DNA. It is a not only a qualitative but also a quantitative method. The fragments generated according to the exemplified protocol can be used for analysis according to the methods provided herein.

Example 6

Analysis of Sequence Variations in Sample Mixtures

The aim of this study was to perform analysis of sequence variations in a target sequence relative to a reference sequence by base-specific fragmentation in samples with different DNA ratios of wildtype and mutant DNA, and to evaluate detection sensitivity.

Materials and Methods

The DNA was a 269 bp amplicon derived from the oncogene K-Ras (SEQ ID NO. 44). DNA samples contained either the wild-type sequence or a K-Ras mutant sequence derived from tumor ecII lines. DNA samples (Samples A, B, C, D and E) were mixed in different ratios of wildtype and heterozygote mutated DNA. The ratio of mutated DNA in the mixture varied from 0% to 50% per sample as represented in the table below:

| DNA Name | Ratio of wt DNA to heterozygote mutated DNA | Percent mutated DNA |
| --- | --- | --- |
| DNA A | 1:1 | 25% |
| DNA B | 9:1 | 5% |
| DNA C | 0:1 | 50% |
| DNA D | 4:1 | 10% |
| DNA E | 1:0 | 0% |

Each DNA sample contained 50 ng (5 μl of 10 ng/μl). The homogenous base-specific cleavage reactions according to the protocol provided in Example 1 were performed four times on four different days. The fragments obtained by differential cleavage of the mutant amplicon relative to the wild-type amplicon were analyzed by mass spectrometry, followed by analysis of the mass spectral fragment peaks according to the methods provided herein.

Results

A G/A substitution at position 216 was detected in the mutant amplicon. The mutation was confirmed by a mass shift in the C specific forward reaction from 2313d in the G allele to 2297d in the A allele. Detection of this signal was necessary to identify the presence of an SNP in the mutant sequence. The signal at 2297d (corresponding to the A allele) was detected in all DNA samples A, B, C, and D, even when the mutant allele was only present at a level of 5% (DNA sample B).

Since modifications will be apparent to those of skill in this art, it is intended that this invention be limited only by the scope of the appended claims.

What is claimed is:

1. A method for determining the sequence of one or more sequence variations in a target nucleic acid relative to a reference sequence, comprising:
   (a) generating mass signals for target nucleic acid fragments by mass spectrometry, wherein the target nucleic acid fragments result from a specific cleavage reaction of the target nucleic acid;
   (b) generating or simulating mass signals for reference fragments, wherein the reference fragments result from cleavage or simulated cleavage of the reference sequence using the same specific cleavage reaction in (a);
   (c) identifying mass signals in the target nucleic acid fragment spectrum that are different relative to the reference fragment spectrum, thereby identifying different target nucleic acid fragments;
   (d) generating one or more compomer witnesses corresponding to each different target nucleic acid fragment identified in (c);
   (e) selecting, from the set of all possible subsequences of the reference sequence, a subset of subsequences having at most k cleavage points for the specific cleavage reaction, wherein k is user-defined;
   (f) generating for each compomer witness in (d) all possible sequence variations of one or more subsequences in the subset selected in (e) that would lead to the compomer witness, thereby identifying a reduced set of candidate sequence variations; and
   (g) scoring the candidate sequence variations identified in (f) to determine the sequence of the one or more sequence variations in the target nucleic acid.

2. The method of claim 1, wherein the differences in mass signals in (c) are additional signals.

3. The method of claim 1, wherein two or more sequence variations are determined.

4. The method of claim 1, wherein the sequence variation is at one or more base positions.

5. The method of claim 1, wherein the sequence variation is a mutation or a polymorphism.

6. The method of claim 5, wherein the mutation is an insertion, a deletion or a substitution.

7. The method of claim 5, wherein the polymorphism is a single nucleotide polymorphism.

8. The method of claim 1, wherein the target nucleic acid is from an organism selected from the group consisting of eukaryotes, prokaryotes and viruses.

9. The method of claim 8, wherein the organism is a bacterium.

10. The method of claim 9, wherein the bacterium is selected from the group consisting of *Helicobacter pyloris, Borelia burgdorferi, Legionella pneumophilia, Mycobacteria* sp, *M. tuberculosis, M. avium, M. intracellulare, M. kansaii, M. gordonae, Staphylococcus aureus, Neisseria gonorrheae, Neisseria meningitidis, Listeria monocytogenes, Streptococcus pyogenes, Streptococcus agalactiae, Streptococcus* sp., *Streptococcus faecalis, Streptococcus bovis, Streptococcus pneumoniae, Campylobacter* sp., *Enterococcus* sp., *Haemophilus influenzae, Bacillus antracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidum, Treponema pertenue, Leptospira* and *Actinomyces israelli*.

11. The method of claim 1, which further comprises (i) providing a target nucleic acid and a reference nucleic acid; (ii) generating fragments of the target nucleic acid and the reference nucleic acid by specific cleavage; and wherein the fragments of (ii) are provided in (a) and (b).

12. The method of claim 11, wherein the target nucleic acid is in a mixture of nucleic acids.

13. The method of claim 11, wherein the mixture comprises the reference nucleic acid.

14. The method of claim 11, wherein the mixture comprises a plurality of reference nucleic acids.

15. The method of claim 11, wherein the mixture comprises a plurality of target nucleic acids.

16. The method of claim 11, wherein one specific cleavage agent is utilized to generate fragments.

17. The method of claim 11, wherein two or more specific cleavage agents are utilized to generate fragments.

18. The method of claim 11, wherein specific cleavage comprises treatment with an RNAse.

19. The method of claim 11, wherein specific cleavage comprises treatment with a specific cleavage agent selected from the group consisting of RNase T1, RNase U2, the RNase PhyM, RNase A, chicken liver RNase, RNase CL3 and cusativin.

20. The method of claim 11, wherein specific cleavage comprises treatment with a glycosylase.

21. The method of claim 11, wherein the target nucleic acid is in a pool of nucleic acids from individuals.

22. The method of claim 11, wherein the target nucleic acid is genomic DNA from a single individual.

23. The method of claim 11, wherein the target nucleic acid is selected from the group consisting of single stranded DNA, double stranded DNA, cDNA, single stranded RNA, double stranded RNA, DNA/RNA hybrid, and a DNA/RNA mosaic nucleic acid.

24. The method of claim 11, wherein the target nucleic acid is produced by transcription.

25. The method of claim 1, wherein sequence variations in the target biomolecule permit genotyping a subject, forensic analysis, disease diagnosis or disease prognosis.

26. The method of claim 1, wherein the method determines epigenetic changes in a target nucleic acid molecule relative to a reference nucleic acid molecule.

27. The method of claim 1, wherein the target nucleic acid is from a tumor sample.

28. The method of claim 1, wherein compomer witnesses are generated based upon parameters selected from the group consisting of mass of the different fragment, peak separation between fragments whose masses differ by a single nucleotide in type or length, and mass spectrometer resolution.

29. The method of claim 1, wherein sequence variations in (f) are determined according to one or more candidate sequences having at most k nucleotide insertions, deletions, substitutions and/or modifications compared to the reference sequence.

30. The method of claim 29, wherein k is one or two.

31. The method of claim 29, wherein k is three or more.

32. The method of claim 1, wherein a simulated spectrum is generated for each sequence variation candidate, and each spectrum is scored.

33. The method of claim 1, wherein scores assigned to a sequence variation candidate for multiple target nucleic acids are combined for an overall score of the sequence variation candidate.

34. The method of claim 1, wherein sequence variation in the target nucleic acid is recorded in a record.

35. The method of claim 1, wherein the one or more compomer witnesses for each different fragment have a mass within a selected mass difference from the actual mass of the different fragment.

36. The method of claim 35, wherein the mass difference is the resolution of mass measurement.

37. A method for detecting a sequence variation in a target nucleic acid, comprising:
(a) generating mass signals for target nucleic acid fragments and reference nucleic acid fragments by mass spectrometry, wherein the target nucleic acid fragments and the reference nucleic acid fragments result from cleavage of the target nucleic acid and reference nucleic acid by two or more specific cleavage reactions;
(b) identifying, for at least two of the two or more specific cleavage reactions, mass signals in the target nucleic acid fragment spectrum that are different relative to the reference fragment spectrum, thereby identifying different target nucleic acid fragments;
(c) identifying different target nucleic acid fragments in each of the at least two specific cleavage reactions that are consistent with the sequence variation in the target nucleic acid, thereby identifying consistent different fragments;
(d) combining the consistent different fragments of (c) to obtain set of consistent different fragments;
(e) generating for each of the consistent different fragments of (d) one or more compomer witnesses;
(f) determining a reduced set of sequence variation candidates corresponding to the compomer witnesses; and
(g) scoring the sequence variation candidates of (f) to determine the presence or absence of the sequence variation in the target.

38. The method of claim 37, wherein compomer witnesses are generated based upon parameters selected from the group consisting of mass of the different fragment, peak separation between fragments whose masses differ by a single nucleotide in type or length, and mass spectrometer resolution.

39. The method of claim 37, wherein candidate sequence variations in (f) are determined according to one or more candidate sequences having at most k nucleotide insertions, deletions, substitutions and/or modifications compared to the reference sequence, wherein k is user-defined.

40. The method of claim 39, wherein k is one or two.

41. The method of claim 39, wherein k is three or more.

42. The method of claim 37, wherein one or more sequence variations are recorded in a record.

43. The method of claim 37, wherein the one or more compomer witnesses for each consistent different fragment have a mass within a selected mass difference from the actual mass of the consistent different fragment.

44. The method of claim 43, wherein the mass difference is the resolution of mass measurement.

45. A method for detecting one or more sequence variations in a target nucleic acid, comprising:
(a) providing reference sequence s for the target nucleic acid sequence, a description of cleavage reaction conditions, and maximal sequence variation order k;
(b) determining for reference sequence s all subsequences s[i,j] in set $C_k$, wherein s[i,j] represents a subsequence of reference sequence s beginning at position i and ending at position j, wherein $C_k$ is described by $C_k:=\{(c[i,j], b[i,j]): 1 \leq i \leq j \leq \text{length of s, and ord}[i,j]+\#b[i,j] \leq k\}$,
wherein c[i,j] represents the compomer corresponding to s[i,j]
wherein b[i,j] represents the boundary corresponding to s[i,j],
wherein ord[i,j] is the number of times s[i,j] is cleaved under the cleavage reaction conditions,
wherein #b[i,j] is the value of b[i,j], wherein:
b[i,j]=2 if s is neither cleaved directly before i nor after j,
b[i,j]=1 if s is cleaved either directly before i or directly after j, but s is not cleaved directly before i and directly after j, and
b[i,j]=0 if s is cleaved directly before i and directly after j;
(c) generating mass signals for target nucleic acid fragments by mass spectrometry, wherein the target nucleic acid fragments result from the cleavage reaction conditions in (a);
(d) generating or simulating mass signals for reference sequence fragments, wherein the reference sequence fragments result from reference sequence s using the cleavage reaction conditions in (a);
(e) identifying mass signals in the target nucleic acid fragment spectrum that are different relative to the reference fragment spectrum, thereby identifying different target nucleic acid fragments;

(f) generating one or more compomer witnesses c' corresponding to each different target nucleic acid fragment identified in (e);

(g) for every compomer witness c', identifying all c[i,j] in $C_k$ such that $D(c',c,b) \leq k$, wherein $D(c',c,b)$ is the minimum number of nucleotide insertions, deletions, substitutions or modifications relative to the reference sequence needed to generate the compomer witness c' from c[i,j];

(h) for every compomer c[i,j] identified in (g), determining all sequence variations using at most k-#b insertions, deletions, substitutions or modifications that transform c into c', thereby identifying a reduced set of candidate sequence variations; and (i) scoring the reduced set of candidate sequence variations to detect the one or more sequence variations in the target nucleic acid from the reduced set of candidate sequence variations.

46. The method of claim 45, wherein k is 1 or 2.

47. The method of claim 45, wherein k is 3.

48. The method of claim 45, wherein one or more sequence variations are recorded in a record.

49. The method of claim 45, wherein the differences in mass signals in (e) are additional signals.

50. The method of claim 45, which further comprises (i) providing a target nucleic acid and a reference nucleic acid; (ii) generating fragments of the target nucleic acid and the reference nucleic acid by specific cleavage; and wherein the fragments of (ii) are provided in (c) and (d).

51. The method of claim 45, wherein compomer witnesses are generated based upon parameters selected from the group consisting of mass of the different fragment, peak separation between fragments whose masses differ by a single nucleotide in type or length, and mass spectrometer resolution.

52. The method of claim 45, wherein scores assigned to a sequence variation candidate for multiple target nucleic acids are combined for an overall score of the sequence variation candidate.

53. A method of determining a reduced set of sequence variation candidates in a target nucleic acid relative to a reference sequence, comprising:

(a) generating mass signals for target nucleic acid fragments by mass spectrometry, wherein the target nucleic acid fragments result from a specific cleavage reaction of the target nucleic acid;

(b) generating or simulating mass signals for reference fragments, wherein the reference fragments result from cleavage or simulated cleavage of the reference sequence using the same specific cleavage reaction in (a);

(c) identifying mass signals in the target nucleic acid fragment spectrum that are different relative to the reference fragment spectrum, thereby identifying different target nucleic acid fragments;

(d) generating one or more compomer witnesses corresponding to each different target nucleic acid fragment identified in (c);

(e) selecting, from the set of all possible subsequences of the reference sequence, a subset of subsequences having at most k cleavage points for the specific cleavage reaction; and (f) generating for each compomer witness in (d) all possible sequence variations of one or more subsequences in the subset selected in (e) that would lead to the compomer witness, thereby identifying a reduced set of candidate sequence variations in the target nucleic acid.

54. The method of claim 53, further comprising scoring the candidate sequence variations identified in (f) to determine the sequence of one or more sequence variations in the target nucleic acid.

55. The method of claim 53, wherein the differences in mass signals in (c) are additional signals.

56. The method of claim 53, which further comprises (i) providing a target nucleic acid and a reference nucleic acid; (ii) generating fragments of the target nucleic acid and the reference nucleic acid by specific cleavage, wherein the fragments of (ii) are provided in (a) and (b).

57. The method of claim 56, wherein one specific cleavage agent is utilized to generate fragments.

58. The method of claim 56, wherein two or more specific cleavage agents are utilized to generate fragments.

59. The method of claim 53, wherein compomer witnesses are generated based upon parameters selected from the group consisting of mass of the different fragment, peak separation between fragments whose masses differ by a single nucleotide in type or length, and mass spectrometer resolution.

60. The method of claim 54, wherein the one or more sequence variations are determined according to one or more candidate sequence variations having at most k nucleotide insertions, deletions, substitutions and/or modifications compared to the reference sequence, wherein k is user-defined.

61. The method of claim 53, wherein a simulated spectrum is generated for each sequence variation candidate, and each spectrum is scored.

62. The method of claim 53, wherein scores assigned to a sequence variation candidate for multiple target nucleic acids are combined for an overall score of the sequence variation candidate.

* * * * *

SEQUENCE LISTING

```
<160> NUMBER OF SEQ ID NOS: 85

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Pro Phe His Leu Leu Val Tyr
 1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Any amino acid except pro or arg

<400> SEQUENCE: 2

Ile Glu Gly Arg Xaa
 1               5
```

```
<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Any amino acid except pro or arg

<400> SEQUENCE: 3

Ile Asp Gly Arg Xaa
 1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Any amino acid except pro or arg

<400> SEQUENCE: 4

Ala Glu Gly Arg Xaa
 1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (5)
<223> OTHER INFORMATION: Variable amino acid

<400> SEQUENCE: 5

Pro Xaa Gly Pro Xaa
 1               5

<210> SEQ ID NO 6
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cagtaatacg actcactata gggagaaggc tccccagcaa gacggactt           49

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 7
aggaagagag cgcctcggca aagtacac                                                28

<210> SEQ ID NO 8
<211> LENGTH: 340
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 8
gggagaaggc tccccagcaa gacggacttc ttcaaaaaca tcatgaactt catagacatt        60
gtggccatca ttccttattt catcacgctg gcaccgaga tagctgagca ggaaggaaac        120
cagaagggcg agcaggccac ctccctggcc atcctcaggg tcatccgctt ggtaagggtt       180
tttagaatct tcaagctctc ccgccactct aagggcctcc agatcctggg ccagaccctc       240
aaagctagta tgagagagct agggctgctc atctttttcc tcttcatcgg ggtcatcctg       300
ttttctagtg cagtgtactt tgccgaggcg ctctcttcct                             340

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cccagtcacg acgttgtaaa acg                                                23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agcggataac aatttcacac agg                                                23

<210> SEQ ID NO 11
<211> LENGTH: 117
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 11
cccagtcacg acgttgtaaa acgtccaggg aggactcacc atgggcattt gattgcagag        60
cagctccgag tccatccaga gcttcctgca gtcacctgtg tgaaattgtt atccgct          117

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:
      Illustrative nucleotide sequence
<220> FEATURE:

```
<221> NAME/KEY: modified_base
<222> LOCATION: (1)..(3)
<223> OTHER INFORMATION: a, c, g, t, unknown, or other
<220> FEATURE:
<221> NAME/KEY: modified_base
<222> LOCATION: (8)..(10)
<223> OTHER INFORMATION: a, c, g, t, unknown, or other
<220> FEATURE:
<221> NAME/KEY: modified_base
<222> LOCATION: (12)..(14)
<223> OTHER INFORMATION: a, c, g, t, unknown, or other
<220> FEATURE:
<221> NAME/KEY: modified_base
<222> LOCATION: (19)..(21)
<223> OTHER INFORMATION: a, c, g, t, unknown, or other

<400> SEQUENCE: 12
nnnactgnnn mnnntgacnn n                                             21

<210> SEQ ID NO 13
<211> LENGTH: 583
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 13
cttcagtgct cacaccgacc ctatgagtgg ggcggtcaaa ctgtccccat tttacacaca     60
gggaaactta gtgaatggca aggctgggtt tgagcccagc tctattgccc ccaaagataa    120
ggctccattc cctgctccat ttcccaggca tagggacttg taggggctg gaaccccagg     180 atcaactctg ggctcagagg gccccagcaa taagtgactg ttgattactc ctgatcccaa    240
agctgacttc aggcaagctc cttggaggtc gcagccccctt cttgctatgc ccagtggcaa    300
tgatgttcat aatcccactc ctcagtgcag ggttccacta agaacccatg atctcctacc    360
tcaaatggac ctcatgcttt ctgagtaagc ctccctcagc tttctggtca cctcactccc    420
cccacccact gcaatgactt cttcaggcct tccctgccat cctcaaatct ccagctgccc    480
cctcctgtct accttccact tccctctcca cacacaacct gcttaccaga gagctgagca    540
gagccaccaa cagaacttcc cccccacgtc gctgctccca gtc                     583

<210> SEQ ID NO 14
<211> LENGTH: 483
<212> TYPE: DNA
<213> ORGANISM: Mycobacterium abscessus

<400> SEQUENCE: 14
acgggtgagt aacacgtggg tgatctgccc tgcactctgg gataagcctg ggaaactggg     60
tctaataccg gataggacca cacttcat ggtgagtggt gcaaagcttt tgcggtgtgg      120
gatgagcccg cggcctatca gcttgttggt ggggtaatgg cccaccaagg cgacgacggg    180
tagccggcct gagagggtga ccggccacac tgggactgag atacggccca gactcctacg    240
ggaggcagca gtggggaata ttgcacaatg ggcgcaagcc tgatgcagcg acgccgcgtg    300
agggatgacg gccttcgggt tgtaaaccte tttcagtagg gacgaagcga agtgacggt    360 acctacagaa gaaggaccgg ccaactacgt gccagcagcc gcggtaatac gtagggtccg    420
agcgttgtcc ggaattactg ggcgtaaaga gctcgtaggt ggtttgtcgc gttgttcgtg    480
aaa                                                                 483

<210> SEQ ID NO 15
```

<211> LENGTH: 495
<212> TYPE: DNA
<213> ORGANISM: Mycobacterium avium

<400> SEQUENCE: 15

```
acgggtgagt aacacgtggg caatctgccc tgcacttcgg gataagcctg ggaaactggg      60
tctaataccg gataggacct caagacgcat gtcttctggt ggaaagcttt tgcggtgtgg     120
gatgggcccg cggcctatca gcttgttggt ggggtgacgg cctaccaagg cgacgacggg    180
tagccggcct gagagggtgt ccggccacac tgggactgag atacggccca gactcctacg    240
ggaggcagca gtggggaata ttgcacaatg ggcgcaagcc tgatgcagcg acgccgcgtg    300
ggggatgacg gccttcgggt tgtaaacctc tttcaccatc gacgaaggtc cgggttttct    360
cggattgacg gtaggtggag aagaagcacc ggccaactac gtgccagcag ccgcggtaat    420
acgtagggtg cgagcgttgt ccggaattac tgggcgtaaa gagctcgtag gtggtttgtc    480
gcgttgttcg tgaaa                                                      495
```

<210> SEQ ID NO 16
<211> LENGTH: 495
<212> TYPE: DNA
<213> ORGANISM: Mycobacterium celatum

<400> SEQUENCE: 16

```
acgggtgagt aacacgtggg tgatctgccc tgcacttcgg gataagcttg ggaaactggg      60
tctaataccg gataggacca tgggatgcat gtcttgtggt ggaaagcttt tgcggtgtgg     120
gatgggcccg cggcctatca gcttgttggt ggggtgatgg cctaccaagg cgacgacggg    180
tagccggcct gagagggtgt ccggccacac tgggactgag atacggccca gactcctacg    240
ggaggcagca gtggggaata ttgcacaatg ggcgcaagcc tgatgcagcg acgccgcgtg    300
ggggatgacg gccttcgggt tgtaaacctc tttcaccatc gacgaagctg ccggttttcc    360
ggtggtgacg gtaggtggag aagaagcacc ggccaactac gtgccagcag ccgcggtaat    420
acgtagggtg cgagcgttgt ccggaattac tgggcgtaaa gagctcgtag gtggtttgtc    480
gcgttgttcg tgaaa                                                      495
```

<210> SEQ ID NO 17
<211> LENGTH: 483
<212> TYPE: DNA
<213> ORGANISM: Mycobacterium fortuitum

<400> SEQUENCE: 17

```
acgggtgagt aacacgtggg tgatctgccc tgcactttgg gataagcctg ggaaactggg      60
tctaataccg aatatgacca cgcgcttcat ggtgtgtggt ggaaagcttt tgcggtgtgg     120
gatgggcccg cggcctatca gcttgttggt ggggtaatgg cctaccaagg cgacgacggg    180
tagccggcct gagagggtga ccggccacac tgggactgag atacggccca gactcctacg    240
ggaggcagca gtggggaata ttgcacaatg ggcgcaagcc tgatgcagcg acgccgcgtg    300
agggatgacg gccttcgggt tgtaaacctc tttcaatagg gacgaagcgc aagtgacggt    360
acctatagaa gaaggaccgg ccaactacgt gccagcagcc gcggtaatac gtagggtccg    420
agcgttgtcc ggaattactg ggcgtaaaga gctcgtaggt ggtttgtcgc gttgttcgtg    480
aaa                                                                   483
```

<210> SEQ ID NO 18
<211> LENGTH: 495

<212> TYPE: DNA
<213> ORGANISM: Mycobacterium gordonae

<400> SEQUENCE: 18

```
acgggtgagt aacacgtggg taatctgccc tgcacatcgg gataagcctg ggaaactggg      60
tctaataccg aataggacca caggacacat gtcctgtggt ggaaagcttt tgcggtgtgg     120
gatgggcccg cggcctatca gcttgttggt ggggtgatgg cctaccaagg cgacgacggg     180
tagccggcct gagagggtgt ccggccacac tgggactgag atacggccca gactcctacg     240
ggaggcagca gtggggaata ttgcacaatg ggcgaaagcc tgatgcagcg acgccgcgtg     300
ggggatgacg gccttcgggt tgtaaacctc tttcaccatc gacgaaggtc cgggttttct     360
cgggctgacg gtaggtggag aagaagcacc ggccaactac gtgccagcag ccgcggtaat     420
acgtagggtg cgagcgttgt ccggaattac tgggcgtaaa gagctcgtag gtggtttgtc     480
gcgttgttcg tgaaa                                                     495
```

<210> SEQ ID NO 19
<211> LENGTH: 495
<212> TYPE: DNA
<213> ORGANISM: Mycobacterium intracellulare

<400> SEQUENCE: 19

```
acgggtgagt aacacgtggg caatctgccc tgcacttcgg gataagcctg ggaaactggg      60
tctaataccg gataggacct ttaggcgcat gtctttaggt ggaaagcttt tgcggtgtgg     120
gatgggcccg cggcctatca gcttgttggt ggggtgatgg cctaccaagg cgacgacggg     180
tagccggcct gagagggtgt ccggccacac tgggactgag atacggccca gactcctacg     240
ggaggcagca gtggggaata ttgcacaatg ggcgcaagcc tgatgcagcg acgccgcgtg     300
ggggatgacg gccttcgggt tgtaaacctc tttcaccatc gacgaaggtc cgggttttct     360
cggattgacg gtaggtggag aagaagcacc ggccaactac gtgccagcag ccgcggtaat     420
acgtagggtg cgagcgttgt ccggaattac tgggcgtaaa gagctcgtag gtggtttgtc     480
gcgttgttcg tgaaa                                                     495
```

<210> SEQ ID NO 20
<211> LENGTH: 495
<212> TYPE: DNA
<213> ORGANISM: Mycobacterium kansasii

<400> SEQUENCE: 20

```
acgggtgagt aacacgtggg caatctgccc tgcacaccgg gataagcctg ggaaactggg      60
tctaataccg gataggacca cttggcgcat gccttgtggt ggaaagcttt tgcggtgtgg     120
gatgggcccg cggcctatca gcttgttggt ggggtgacgg cctaccaagg cgacgacggg     180
tagccggcct gagagggtgt ccggccacac tgggactgag atacggccca gactcctacg     240
ggaggcagca gtggggaata ttgcacaatg ggcgcaagcc tgatgcagcg acgccgcgtg     300
ggggatgacg gccttcgggt tgtaaacctc tttcaccatc gacgaaggtc cgggttctct     360
cggattgacg gtaggtggag aagaagcacc ggccaactac gtgccagcag ccgcggtaat     420
acgtagggtg cgagcgttgt ccggaattac tgggcgtaaa gagctcgtag gtggtttgtc     480
gcgttgttcg tgaaa                                                     495
```

<210> SEQ ID NO 21
<211> LENGTH: 495
<212> TYPE: DNA

<213> ORGANISM: Mycobacterium marinum

<400> SEQUENCE: 21

```
acgggtgagt aacacgtggg cgatctgccc tgcacttcgg gataagcctg ggaaactggg      60
tctaataccg gataggacca cgggattcat gtcctgtggt ggaaagcttt tgcggtgtgg     120
gatgggcccg cggcctatca gcttgttggt ggggtaacgg cctaccaagg cgacgacggg     180
tagccggcct gagagggtgt ccggccacac tgggactgag atacgcccca gactcctacg     240
ggaggcagca gtggggaata ttgcacaatg ggcgcaagcc tgatgcagcg acgccgcgtg     300
ggggatgacg gccttcgggt tgtaaacctc tttcaccatc gacgaaggtt cgggttttct     360
cggattgacg gtaggtggag aagaagcacc ggccaactac gtgccagcag ccgcggtaat     420
acgtagggtg cgagcgttgt ccggaattac tgggcgtaaa gagctcgtag gtggtttgtc     480
gcgttgttcg tgaaa                                                      495
```

<210> SEQ ID NO 22
<211> LENGTH: 492
<212> TYPE: DNA
<213> ORGANISM: Mycobacterium scrofulaceum

<400> SEQUENCE: 22

```
acgggtgagt aacacgtggg caatctgccc tgcacttcgg gataagcctg ggaaactggg      60
tctaataccg gataggacca cttggcgcat gccttgtggt ggaaagcttt tgcggtgtgg     120
gatgggcccg cggcctatca gctagttggt ggggtgatgg cctaccaagg cgacgacggg     180
tagccggcct gagagggtgt ccggccacac tgggactgag atacgcccca gactcctacg     240
ggaggcagca gtggggaata ttgcacaatg ggcgcaagcc tgatgcagcg acgccgcgtg     300
ggggatgacg gccttcgggt tgtaaacctc tttcaccatc gacgaaggct cactttgtgg     360
gttgacggta ggtggagaag aagcaccggc caactacgtg ccagcagccg cggtaatacg     420
tagggtgcga gcgttgtccg gaattactgg gcgtaaagag ctcgtaggtg gtttgtcgcg     480
ttgttcgtga aa                                                         492
```

<210> SEQ ID NO 23
<211> LENGTH: 485
<212> TYPE: DNA
<213> ORGANISM: Mycobacterium smegmatis

<400> SEQUENCE: 23

```
acgggtgagt aacacgtggg tgatctgccc tgcactttgg gataagcctg ggaaactggg      60
tctaataccg aatacaccct gctggtcgca tggcctggta ggggaaagct tttgcggtgt     120
gggatgggcc cgcggcctat cagcttgttg gtggggtgat ggcctaccaa ggcgacgacg     180
ggtagccggc ctgagagggt gaccggccac actgggactg agatacgccc agactcctac     240
cgggaggcag cagtggggaa tattgcacaa tgggcgcaag cctgatgcag cgacgccgcg     300
tgagggatga cggccttcgg gttgtaaacc tctttcagca cagacgaagc gcaagtgacg     360
gtatgtgcag aagaaggacc ggccaactac gtgccagcag ccgcggtaat acgtagggtc     420
cgagcgttgt ccggaattac tgggcgtaaa gagctcgtag gtggtttgtc gcgttgttcg     480
tgaaa                                                                 485
```

<210> SEQ ID NO 24
<211> LENGTH: 497
<212> TYPE: DNA
<213> ORGANISM: Mycobacterium tuberculosis

```
<400> SEQUENCE: 24
acgggtgagt aacacgtggg tgatctgccc tgcacttcgg ataagcctg ggaaactggg     60 tctaataccg gataggacca cgggatgcat gtcttgtggt ggaaagcgct ttagcggtgt    120
gggatgagcc cgcggcctat cagcttgttg gtggggtgac ggcctaccaa ggcgacgacg    180
ggtagccggc ctgagagggt gtccggccac actgggactg agatacgcc cagactccta    240 cgggaggcag cagtggggaa tattgcacaa tgggcgcaag cctgatgcag cgacgccgcg    300
tgggggatga cggccttcgg gttgtaaacc tctttcacca tcgacgaagg tccgggttct    360
ctcggattga cggtaggtgg agaagaagca ccggccaact acgtgccagc agccgcggta    420
atacgtaggg tgcgagcgtt gtccggaatt actgggcgta aagagctcgt aggtggtttg    480
tcgcgttgtt cgtgaaa                                                   497

<210> SEQ ID NO 25
<211> LENGTH: 499
<212> TYPE: DNA
<213> ORGANISM: Mycobacterium xenopi

<400> SEQUENCE: 25
acgggtgagt aacacgtggg tgacctgccc tgcacttcgg ataagcctg ggaaactggg     60 tctaataccg gataggacca ttctgcgcat gtggggtggt ggaaagtgtt tggtagcggt    120
gtgggatggg cccgcggcct atcagcttgt tggtggggtg atggcctacc aaggcgacga    180
cgggtagccg gcctgagagg gtgtccggcc acactgggac tgagatacgg cccagactcc    240
tacgggaggc agcagtgggg aatattgcac aatgggcgca agcctgatgc agcgacgccg    300
cgtgggggat gacggccttc gggttgtaaa ccccttttcag cctcgacgaa gctgcgggtt    360
ttctcgtggt gacggtaggg gcagaagaag caccggccaa ctacgtgcca gcagccgcgg    420
taatacgtag ggtgcaagcg ttgtccggaa ttactgggcg taaagagctc gtaggcggct    480
tgtcgcgttg ttcgtggaa                                                499

<210> SEQ ID NO 26
<211> LENGTH: 492
<212> TYPE: DNA
<213> ORGANISM: Mycobacterium paraffinicum

<400> SEQUENCE: 26
acgggtgagt aacacgtggg caatctgccc tgcacttcgg ataagcctg ggaaactggg     60 tctaataccg gataggacca cttggcgcat gccttgtggt ggaaagcttt tgcggtgtgg    120
gatgggcccg cggcctatca gcttgttggt ggggtgatgg cctaccaagg cgacgacggg    180
tagccggcct gagagggtgt ccggccacac tgggactgag atacgccca gactcctacg    240 gaggcagca gtggggaata ttgcacaatg gcgcaagcc tgatgcagcg acgccgcgtg    300
ggggatgacg gccttcgggt tgtaaacctc tttcaccatc gacgaaggct cacttcgtga    360
gttgacggta ggtggagaag aagcaccggc caactacgtg ccagcagccg cggtaatacg    420
tagggtgcga gcgttgtccg gaattactgg gcgtaaagag ctcgtaggtg gtttgtcgcg    480
ttgttcgtga aa                                                       492

<210> SEQ ID NO 27
<211> LENGTH: 483
<212> TYPE: DNA
<213> ORGANISM: Mycobacterium interjectum
```

-continued

```
<400> SEQUENCE: 27
acgggtgagt aacacgtggg taatctgccc tgcacttcgg gataagcctg ggaaactggg     60
tctaataccg gataggacct cgaggcgcat gccttgtggt ggaaagcttt tgcggtgtgg    120
gatgggcccg cggcctatca gctagttggt ggggtgacgg cctaccaagg cgacgacggg    180
tagccggcct gagagggtgt ccggccacac tgggactgag atacggccca gactcctacg    240
ggaggcagca gtggggaata ttgcacaatg ggcgcaagcc tgatgcagcg acgccgcgtg    300
ggggatgacg gccttcgggt tgtaaacctc tttcagcagg gacgaagcgc aagtgacggt    360
acctgcagaa gaagcaccgg ccaactacgt gccagcagcc gcggtaatac gtagggtgcg    420
agcgttgtcc ggaattactg ggcgtaaaga gctcgtaggt ggtttgtcgc gttgttcgtg    480
aaa                                                                 483

<210> SEQ ID NO 28
<211> LENGTH: 484
<212> TYPE: DNA
<213> ORGANISM: Mycobacterium aurum

<400> SEQUENCE: 28
acgggtgagt aacacgtggg tgatctgccc tgcactttgg gataagcctg ggaaactggg     60
tctaataccg aataggacta cgcgatgcat gtcgtgtggt ggaaagcttt tgcggtgtgg    120
gatgggcccg cggcctatca gcttgttggt gaggttacgg ctcaccaagg cgacgacggg    180
tagccggcct gagagggtga ccggccacac tgggactgag atacggccca gactcctacg    240
ggaggcagca gtggggaata ttgcacaatg ggcgcaagcc tgatgcagcg acgccgcgtg    300
agggatgacg gccttcgggt tgtaaacctc tttcgccagg gacgaagcgc aagtgacggt    360
acctggagaa gaaggaccgg ccaactacgt gccagcagcc gcggtaaata cgtagggtgc    420
gagcgttgtc cggaattact gggcgtaaag agctcgtagg tggtttgtcg cgttgttcgt    480
gaaa                                                                484

<210> SEQ ID NO 29
<211> LENGTH: 1542
<212> TYPE: DNA
<213> ORGANISM: Escherichia coli

<400> SEQUENCE: 29
aaattgaaga gtttgatcat ggctcagatt gaacgctggc ggcaggccta acacatgcaa     60
gtcgaacggt aacaggaaga gcttgcttc tttgctgacg agtggcggac gggtgagtaa    120
tgtctgggaa actgcctgat ggagggggat aactactgga aacggtagct aataccgcat    180
aacgtcgcaa gaccaaagag ggggacctt cgggcctctt gccatcggat gtgcccagat    240
ggattagcta gtaggtgggg taacggctca cctaggcgac gatccctagc tggtctgaga    300
ggatgaccag ccacactgga actgagacac ggtccagact cctacgggag gcagcagtgg    360
ggaatattgc acaatgggcg caagcctgat gcagccatgc cgcgtgtatg aagaaggcct    420
tcgggttgta aagtactttc agcggggagg aagggagtaa agttaatacc tttgctcatt    480
gacgttaccc gcagaagaag caccggctaa ctccgtgcca gcagccgcgg taatacggag    540
ggtgcaagcg ttaatcggaa ttactgggcg taaagcgcac gcaggcggtt tgttaagtca    600
gatgtgaaat cccggggctc aacctgggaa ctgcatctga tactggcaag cttgagtctc    660 gtagagggg gtagaattcc aggtgtagcg gtgaaatgcg tagagatctg gaggaatacc    720
ggtggcgaag gcggccccct ggacgaagac tgacgctcag gtgcgaaagc gtgggagca    780
```

```
aacaggatta gataccctgg tagtccacgc cgtaaacgat gtcgacttgg aggttgtgcc     840
cttgaggcgt ggcttccgga gctaacgcgt taagtcgacc gcctgggag tacggccgca     900 aggttaaaac tcaaatgaat tgacggggc ccgcacaagc ggtggagcat gtggtttaat     960
tcgatgcaac gcgaagaacc ttacctggtc ttgacatcca cggaagtttt cagagatgag    1020
aatgtgcctt cgggaaccgt gagacaggtg ctgcatggct gtcgtcagct cgtgttgtga    1080
aatgttgggt taagtcccgc aacgagcgca acccttatcc tttgttgcca gcggtccggc    1140
cgggaactca aaggagactg ccagtgataa actggaggaa ggtggggatg acgtcaagtc    1200
atcatggccc ttacgaccag ggctacacac gtgctacaat ggcgcataca agagaagcg     1260 acctcgcgag agcaagcgga cctcataaag tgcgtcgtag tccggattgg agtctgcaac    1320
tcgactccat gaagtcggaa tcgctagtaa tcgtggatca gaatgccacg gtgaatacgt    1380
tcccgggcct tgtacacacc gcccgtcaca ccatgggagt gggttgcaaa agaagtaggt    1440
agcttaacct tcgggagggc gcttaccact ttgtgattca tgactggggt gaagtcgtaa    1500
caaggtaacc gtaggggaac ctgcggttgg atcacctcct ta                       1542

<210> SEQ ID NO 30
<211> LENGTH: 340
<212> TYPE: DNA
<213> ORGANISM: Bordetella avium

<400> SEQUENCE: 30
agagtttgat cctggctcag attgaacgct ggcgggatgc tttacacatg caagtcgaac     60
ggcagcacgg acttcggtct ggtggcgagt ggcgaacggg tgagtaatgt atcggaacgt    120
gcctagtagc gggggataac tacgcgaaag cgtagctaat accgcatacg ccctacgggg    180
gaaagcgggg gaccttcggg cctcgcacta ttagagcggc cgatatcgga ttagctagtt    240 ggtgggtaa cggctcacca aggcgacgat ccgtagctgg tttgagagga cgaccagcca    300
cactgggact gagacacggc ccagactcct acgggaggca                          340

<210> SEQ ID NO 31
<211> LENGTH: 339
<212> TYPE: DNA
<213> ORGANISM: Bordetella tremmatum

<400> SEQUENCE: 31
agagtttgat cctggctcag attgaacgct ggcgggatgc tttacacatg caagtcggac     60
ggcagcacgg acttcggtct ggtggcgagt ggcgaacggg tgagtaatgt atcggaacgt    120
gcccagtagc gggggataac tacgcgaaag cgtggctaat accgcatacg ccctacgggg    180
aaagcggggg accttcgggc ctcgcactat tggagcggcc gatatcggat tagctagttg    240
gtggggtaac ggctcaccaa ggcgacgatc cgtagctggt ttgagaggac gaccagccac    300
actgggactg agacacggcc cagactccta cgggaggca                           339

<210> SEQ ID NO 32
<211> LENGTH: 1496
<212> TYPE: DNA
<213> ORGANISM: Bordetella petrii
<220> FEATURE:
<221> NAME/KEY: modified_base
<222> LOCATION: (821)
<223> OTHER INFORMATION: a, c, g, or t

<400> SEQUENCE: 32
```

```
cgctagcggg atgctttaca catgcaagtc gaacggcagc gcggacttcg gtctggcggc    60
gagtggcgaa cgggtgagta atgtatcgga acgtgcccag tagcggggga taactacgcg   120
aaagcttagc taataccgca tacgccctac gggggaaagc gggggacctt cgggcctcgc   180
actattggag cggccgatat cggattagct agttggtggg gtaaaggcct accaaggcga   240
cgatccgtag ctggtttgag aggacgacca gccacactgg gactgagaca cggcccagac   300
tcctacggga ggcagcagtg gggaattttg acaatggggg caaccctga tccagccatc    360 ccgcgtgtgc gatgaaggcc ttcgggttgt aaagcacttt tggcaggaaa gaaacggctc   420
tggctaatac ctggggcaac tgacggtacc tgcagaataa gcaccggcta actacgtgcc   480
agcagccgcg gtaatacgta gggtgcaagc gttaatcgga attactgggc gtaaagcgtg   540
cgcaggcggt tcggaaagaa agatgtgaaa tcccagggct taaccttgga actgcatttt   600
taactaccgg gctagagtgt gtcagaggga ggtggaattc cgcgtgtagc agtgaaatgc   660
gtagatatgc ggaggaacac cgatggcgaa ggcagcctcc tgggataaca ctgacgctca   720
tgcacgaaag cgtggggagc aaacaggatt agataccctg gtagtccacg ccctaaacga   780
tgtcatctag ctgttgggga cttcggtcct tggtagcgca nctaacgcgt gaagttgacc   840
gcctggggag tacggtcgca agattaaaac tcaaaggaat tgacggggac ccgcacaagc   900
ggtggatgat gtggattaat tcgatgcaac gcgaaaaacc ttacctaccc ttgacatgtc   960
tggaatgccg aagagatttg gcagtgctcg caagagaacc ggaacacagg tgctgcatgg  1020
ctgtcgtcag ctcgtgtcgt gagatgttgg gttaagtccc gcaacgagcg caacccttgt  1080
cattagttgc tacgaaaggg cactctaatg agactgccgg tgacaaaccg gaggaaggtg  1140
gggatgacgt caagtcctca tggcccttat gggtagggct tcacacgtca tacaatggtc  1200
gggacagagg gctgccaacc cgcaaggggg agccaatccc agaaaccga tcgtagtccg   1260 gatcgcagtc tgcaactcga ctgcgtgaag tcggaatcgc tagtaatcgc ggatcagcat  1320
gtcgcggtga atacgttccc gggtcttgta cacaccgccc gtcacaccat gggagtgggt  1380
tttaccagaa gtagttagcc taaccgcaag ggggcgatt accacggtag gattcatgac   1440
tggggtgaag tcgtaacaag gtagccgtat cggaaggtgc ggttggatca cctcct        1496
```

<210> SEQ ID NO 33
<211> LENGTH: 363
<212> TYPE: DNA
<213> ORGANISM: Bordetella sp.

<400> SEQUENCE: 33

```
agagtttgat cctggctcag gacgaacgct ggcggcgtgc ctaacacatg caagtcgaac    60
gcgagtgtct tttttcgcaa gagagcagac acttgagtgg cgaacgggtg agtaacacgt   120
gagcgactca ccttccggtg ggggataact gtccgaaagg gcggctaata cctcgtatgc   180
tccctgaccg ccgggtcagt gaggaaagtg ggcttcgtaa gaagctcatg ccagaagaga   240
ggctcgcgcc ccatcagcta gttggcgagg taacggctca ccaaggcaat gacgggtagc   300
tggtctgaga ggatggtcag ccactctggg actgagacac ggcccagact cctacgggag   360
gca                                                                 363
```

<210> SEQ ID NO 34
<211> LENGTH: 363
<212> TYPE: DNA
<213> ORGANISM: Bordetella sp.

<400> SEQUENCE: 34

```
agagtttgat cctggctcag gacgaacgct ggcggcgtgc ctaacacatg caagtcgaac      60
gcgagtgtct tttttcgtaa gaaaggtgac acttgagtgg cgaacgggtg agtaacacgt     120
gagtaactca ccttccggtg ggggataact gtccgaaagg gtggctaata ccccatatgc     180
tccctgaccg ccgggtcagt gagaaaagtg ggcttcgtaa aagctcaca ccagaagaga      240 ggctcgcgcc ccatcagctg gttggcgagg taatggctca ccaaggcaat gacgggtagc     300
tggtctgaga ggatggtcag ccacactggg actgagacac ggcccagact cctacgggag     360
gca                                                                  363
```

<210> SEQ ID NO 35
<211> LENGTH: 343
<212> TYPE: DNA
<213> ORGANISM: Bordetella sp.

<400> SEQUENCE: 35

```
agagtttgat catggctcag gatgaacgct ggcggcgtgc ttaatacatg caagtcgaac      60
ggagggaggt agtaatactt tccttagtgg cgaacgggtg agaaacgcgt tggtgacctg     120
ccccgaagag cgggacaaca gaccgaaagg tttgctaata ccgcatgagc tcttgctggc     180
tagagtggca agaggaaagg ccgaaaggcg ctttgggagg ggcctgcgtc ccatcagcta     240
gttggcgggg taacagccca ccaaggcgat gacgggtagg gacctgaga gggtgacccc     300 ccacaatgga actgaaacac ggtccataca cctacgggtg gca                       343
```

<210> SEQ ID NO 36
<211> LENGTH: 342
<212> TYPE: DNA
<213> ORGANISM: Bordetella sp.

<400> SEQUENCE: 36

```
agagtttgat catggctcag gatgaacgct ggcggcgtgc ctaatacatg caagtcgaac      60
gggagatgta gcgatatgtc tccagtggcg aacgggtgag taacgcgttg gtgacctgcc     120
ccgaagagcg ggataacaga ccgaaaggac tgctaatacc gcatgagctc tcggcagtta     180
gaggggccga gaggaaaggc cgaaaggcgc tttgggaggg gcctgcgtcc catcagctag     240
ttggcgaggt aagagctcac caaggcgatg acgggtaggg gacctgagag ggtgacccccc    300 cacaatggaa ctgaaacacg gtccatacac ctacgggtgg ca                        342
```

<210> SEQ ID NO 37
<211> LENGTH: 342
<212> TYPE: DNA
<213> ORGANISM: Bordetella sp.

<400> SEQUENCE: 37

```
agagtttgat catggctcag attgaacgct ggcggcatgc tttacacatg caagtcgaac      60
ggcagcacgg gcttcggcct ggtggcgagt ggcgaacggg tgagtaatgc atcggaacgt     120
gcccatttgt gggggataac gcggcgaaag tcgcgctaat accgcatacg ccctgagggg     180
gaaagcgggg gattcttcgg agcctcgcgc aattggagcg ccgatgtca gattagctag      240 ttggtagggt aaaggcctac caaggcgacg atctgtagcg ggtctgagag gatgatccgc     300
cacactggga ctgagacacg gcccagactc ctacgggagg ca                        342
```

<210> SEQ ID NO 38
<211> LENGTH: 342
<212> TYPE: DNA

<213> ORGANISM: Bordetella sp.

<400> SEQUENCE: 38

```
agagtttgat catggctcag attgaacgct ggcggcatgc tttgcacatg caagtcgaac      60
ggcagcacgg gcttcggcct ggtggcgagt ggcgaacggg tgagtaatgc atcggaacgt     120
gcccatttgt gggggataac gcggcgaaag tcgcgctaat accgcatacg ccctgagggg     180
gaaagcgggg gattcttcgg aacctcgcgc aattggagcg gccgatgtca gattagctag    240
ttggtagggt aaaggcctac caaggcgacg atctgtagcg ggtctgagag gatgatccgc    300
cacactggga ctgagacacg gcccagactc ctacgggagg ca                       342
```

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39

```
agagtttgat cmtggctcag                                                  20
```

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40

```
aaggaggtga tccakccrca                                                  20
```

<210> SEQ ID NO 41
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41

```
gtaatacgac tcactatagg gacgggtgag taacacgt                              38
```

<210> SEQ ID NO 42
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42

```
atttaggtga cactatagaa tttcacgaac aacgcgacaa                             40
```

<210> SEQ ID NO 43
<211> LENGTH: 418
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 43

```
accatgcctg ctgctccctg cctgccagcg ccctgcacat actttgcaca tggctggggg      60
ccagctgcgg gtccctgggg actcggatgg cacagagggc cccttcctgc caccatcacg     120
gctcagacct cacgttcctg gagagtaggg gtgggtgct gaggggcaga gggaagtgcc      180
gcaaaccccc tggtgggcgc ggtgccagcc ccccaggccg attcccatcc agttgaccga     240
gcttgtgctg gtcaccgcgg tttccgcagg acagagtccc cacagccgct gggcaccccg     300
gtcccattcg cggccacttt cctgtctgaa gaccgcatgt gccgggctg tgcttacggc      360 tcgcgggcgc actctactga caagcggtgg gcggcctcac agactctccc aggcccgc      418
```

<210> SEQ ID NO 44
<211> LENGTH: 269
<212> TYPE: DNA
<213> ORGANISM: Artificial Sequence
<220> FEATURE:
<223> OTHER INFORMATION: Description of Artificial Sequence: Synthetic amplicon sequence

<400> SEQUENCE: 44

```
cgtccacaaa atgattctga attagctgta tcgtcaaggc actcttgcct acgccaccag      60
ctccaactac cacaagttta tattcagtca ttttcagcag gccttataat aaaaataatg     120
aaaatgtgac tatattagaa catgtcacac ataaggttaa tacactatca aatactccac     180
cagtaccttt taatacaaac tcacctttat atgaaaaatt atttcaaaat accttacaaa     240
attcaatcat gaaaattcca gttgactgc                                       269
```

<210> SEQ ID NO 45
<211> LENGTH: 428
<212> TYPE: DNA
<213> ORGANISM: Artificial Sequence
<220> FEATURE:
<223> OTHER INFORMATION: Description of Artificial Sequence: Synthetic amplicon sequence

<400> SEQUENCE: 45

```
gggaacatct tgctgctctc agagccagaa aatgctgaca gcctcatgct ggtggacttc      60
gagtacagca gttataacta taggtgaggc tggaaagatg gcttcccata gatctgttcc     120
cayagggctc ttgaaaacag gccagctgcc cagggcattt ggggactgaa tgtccaccct     180
attctcccag gggctttgac attgggaacc attttgtga gtgggtttat gattatactc      240
acgaggaatg gcctttctac aaagcaaggc ccacagacta ccccactcaa gaacagcagg     300
tatgtgggcc agaggctggg gagcaggacc catcctgtga ggaaggaggg aggtggagtc     360
tggaaggaat ggccggaaag gatgttacct gggaaatact ccacagtctc cccaattcct     420
gactcttg                                                              428
```

<210> SEQ ID NO 46
<211> LENGTH: 429
<212> TYPE: DNA
<213> ORGANISM: Artificial Sequence
<220> FEATURE:
<223> OTHER INFORMATION: Description of Artificial Sequence: Synthetic amplicon sequence

<400> SEQUENCE: 46

```
cccactactc tgccttcctg ttcagtaact cttactttg cctgaagtaa cagcatcttc       60
tacttctcca tctagagatt tttgtgtgtg tgccatcaag gttagcaaac tttatacgta     120
gcctaacact taaaaaatgc actcattatc ttaaacctaa taaattccag agtktattkt     180
```

```
ggttctcctc tgttgccctt cctaaaaaat gagctgaaga tgacagtatt tttctttaca    240
tgcttggtta tgacttttaa agttttattt aaataaatgt tgaagctcaa gtttaaagaa    300
gcgttgcaga ggcccayggt ctcctgggtc ccggccacct gtccatattc cacatttgct    360
gactgtgctc cctgcactcc actcaagttg agagttcaaa tagtcttgaa ggggaatcag    420
cttcaggat                                                            429
```

<210> SEQ ID NO 47
<211> LENGTH: 465
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 47

```
ggaagtggtt ttggaggtga taactcacta tttttaggct agaacacaaa gaacaattag     60
tgaatttaag taagaaagtg gaagttatca actaatgtgc tattaaaaat attattttta    120
gtaagaggca tcctaggagt tacagaatgt ctacattcta cagaaatgtc ttcctctcaa    180
gtcttcagag agcaaaggtc acagctacct aaagtgtttc cacttcaagc acagattgta    240
tgcctgaaga ctacatacct tgcattatca accagttcag caagrrcacc aaacaagaat    300
tcgtgagtgg ttctgaaatg ataaatacta aaagtcagca aaagaattat tgaagttata    360
attcctaata aaaagccatg gttataaaat atttaagttt tttgaaaaaa atcttaaaac    420
caccatttgc attgttttta tactactcaa ggctttccag agctc                    465
```

<210> SEQ ID NO 48
<211> LENGTH: 426
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 48

```
tatgataggg aagatgcggc catcactggg atattttcaa atcccaagga catcagagtg     60
aagtgtcagt tgtcagatga tttttaaaagt tatgtcttca gagaaaaaaa gattcatttt    120 ctcatttttaa rccaattaaa tattctgagt gagactaatc actcatttgc ctacgacctt    180
ttagaaaagt tgttttgttg aaatactgta cgtacgctta atctaaattt gcattgacta    240
tgttttagtg tatttataaa tggtgaactc agtttctgaa attaaacttc ttatttgcaa    300
ttttctagtg ctggcagaca ctggcttttt attttttagga taagaaaaca ggcatattct    360
ttgtggtcca ttatctagag cccatacttg ggcagcattt gaaatttcac cttaacccca    420
gacagg                                                               426
```

<210> SEQ ID NO 49
<211> LENGTH: 533
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 49

```
tgcacagggt ttgatctctg agatgtttta tactctctgg cttggaraar rracagtcct     60
gtagtatcaa gaccagacct tgtgtcccca gcccaaggct gccctgggcc yagggacagt    120
```

```
atttggagac ttygytggca gttttgcgtt ggaatcacct ggtgcctccc tgtacgtcca    180 cccayectgt gcccagakcc ccttcgcaag caccatatgc tgttagatcc tcgagcagcc    240
ttgtgggaca gcmaccctgg ggctggtatc accatttatg taagaaaaaa aaggaagtgc    300
tggcccaggg tcccacagcc agcaagttgg agctgcactg cccaagcagg tcctttagyc    360
agctctctgt tgtcccccaa gcccctcagc cccccaggca gctctaaggg ctcagctgct    420
gcaggattcc ttagagaagc tgaagggttt gggtcctcag ctcctggccg gggcaagtct    480
ggccaagcag catggcagcg atgaagtcca catgatcgaa gggtggatgc tta            533

<210> SEQ ID NO 50
<211> LENGTH: 422
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 50
caaggcttga ctgaaggacc tcatccagag tcactatcag agctcgctcc agcactctcc    60
ttcatggagc cccagggtca gcagtggaga gggtcagagc accccacaa ccccacagc     120 gagatgacct sggctcgtct tgcctctgcc accagagctg tgactgtggg caagatattt    180
tacagcagga ccagtttctt gtccgaaggc agggctatta acaggaccta actcaggata    240
cttgtgtgga taaaatcatg tgtgaagagc ttttagggcc ttgcttctca aagaggggcc    300
ccaggccatc agcacacctg gagtgtgcag ggggaagctc tcagccccac cccagccctc    360
tttacaagac ccccgcgtgg cacctgtggc gtggcacctg tgtgcactcg tgttttcaaa    420
gc                                                                  422

<210> SEQ ID NO 51
<211> LENGTH: 411
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 51
atccctctgt ctctccacca ggaactagaa ttttgtgtat cactgcgctt attttttct    60 tttagtttac cacatgtgta tgtatctata agtaatataa cgatctgttt tgcttctcta    120
tattgtgcca tatgtcgttt ttagcaactt gcttttagct gacgttctgt tttcaagatt    180
catccatgtt gctgcataaa cctaacattc acttactgtt gctggtgwaw aacawwccaw    240
cawgwgagca cagacatttg ggttgtttcc aagacatgta tcaatggcaa aaattaagat    300
gtctgacaaa accaagagtt ggagaggatg tggatggctt ggaattttat ctgctccttt    360
acacccactc tggaaaaact gtacaaacaa ttctgcaagg attttccag a              411

<210> SEQ ID NO 52
<211> LENGTH: 445
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 52
tagtgaaaag ggcacacagc tgtaactcca gacatctccc tattgcatgg atctgcactt    60
```

-continued

```
gactggcagc ctagacagaa ggastgctat ttgtcttttc tggctgacag ctgagcagga    120
ccagcgctgg ctgcaaccaa ggagcattgc ttcgcttgtc atacttctgc ttccaaacag    180
ccctcttttg tttgtgctgt gaagttccca taccgtctgc catctcagca tctcctctgg    240
ctgaacctcc ttcacagttt gtacyctayg ttaaattagc tgttcaattc ctccaggaga    300
aaggactgtg gctattagtt cttagaagcc caaagagcc cagtatgggc ctaggcttgc     360
actaggatcc catgaagcta gctggctggc tgggtgggtg gatcagaccg gcaaaagcac    420
tgtaggagct tgaaacccag cagac                                          445
```

```
<210> SEQ ID NO 53
<211> LENGTH: 425
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 53
```

```
cctctccttc tctgcgtgac cttgggctgg gagccaccca ggaaatgttc tcgagaaatg    60
aggacttcaa ttccgaggtg gggagtgtca tctcctctct catgcctcag tttcccaatt    120
tatagacaag gtgggmggag ccttcttgag gccccttgg gctctgacat ttcatgaacc     180
ggtaacaccc ctcccactca gcatgcacct ggatgcccaa ggcgggtgtc tgggagaaag    240
gtctgctccc acagtgaaga ggccagggtg gcctccagcc tagggctggg gggcagggtc    300
ctcagtgcag agggctgagt gggctcttgt tcagacgggt ggtcagggag aggatgggtc    360
agagacagtg agcacagagg gargrgttca ggtgccttga gtggcacctc atggaaagaa    420
gccct                                                                425
```

```
<210> SEQ ID NO 54
<211> LENGTH: 424
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 54
```

```
aacctcctac gggccttta tgagctgtcg cagactcacc ggggtaatgg catcccccaa     60
agctgtggtg tgaccstggg caatccctgg ggcctctcac tcccatgctg aggtgggtca    120
gacccacagc gcctgacctc aggctccctc tgggctgggc ctggtcccag gtgctgggat    180
ttgcgatggg cctgcgggga acatctagat cagctggtct cttaagggcc gcaacgatga    240
acaggcccca ccctgtctcc tcacactgcc actggcagta cacaaggccc ttgcttattt    300
atatttctga caacctgtaa ctctgggcag gccgactgca gctgacccca gctactgcag    360
aaaatgaagc cagacaaag gagagggcca cactgctccc aagtggtgga gctgttgttc     420
caat                                                                 424
```

```
<210> SEQ ID NO 55
<211> LENGTH: 393
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 55
```

```
agatgcccct gacactgact caaggctcag agaaggcggg cacctgccta aggccacccg    60
gtaggcccaa ggtgtatcaa gactccatcc caggacctct gggccctggg ctgcaggcct   120
gggccctacc cactgattga ttggacctgt gcctccwcca ggtgatggtc aagtggactt   180
tgaggagttt gtgacccttc tgggacccaa actctccacc tcaggatccc agagaagtt    240 ccatggcacc gactttgata ctgtcttctg gaaggtatcc cctggctagt tgggacccag   300
ggctgtgcac actgtggagt tctgttctgg agccagtgaa tggctgggcc cacactgtaa   360 agggggatg accacctcag gcttgtgtcc act                                 393
```

<210> SEQ ID NO 56
<211> LENGTH: 499
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 56

```
gaacccatgt cctccacatc cacaagtctc caaagggttg gggattcctt gtgtgagctc    60
cagatcccaa tcctctggtg gttcatggtg ttgtcaatga cakgtctctc cttgtcaccc   120
cagtatgaaa atgaggagac ttacaggggtg cgaacattcc agataggtac aggggagaaa  180
ctggtgaagg ccctggttcc agcctttctg ggtagaacca tctcctccta tgccacctgt   240
ttgggcccct cctgggactt tatcaccgtg ccagacttca tggaggaact gtttaccagg   300
tgaatgtcca tccctccaa ctcacagtgg tgactgtctc cgactagctg tgtcttgagg    360
atgtcaccga agccctctga gcctgtttgc tcctttgtaa agcagtgaga tgaacctcat   420
agggttctta tgggaactaa atggcctaag gcatggcaag caggtcccaa gtgcctggct   480
ctgtgaaaag gctgctgag                                                499
```

<210> SEQ ID NO 57
<211> LENGTH: 399
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 57

```
ccaggacagc tgaggacatt ccagaccctc scatctcctt cctggagcct cacaggcccc    60
cagagcccct gaaagggcag aaattggtca gctcagcagc cactcacact ggatcttata   120
gaggttgctg gtttccttct tggacagcag ggtggagtgg gcatccttcc ggggatccac   180
tttgtgaaca aagagggagc ggaaccagct gccttcattg tccttggaat agaaactgca   240
ggacagagga gttgaggggg acgcgcggag gttgggggag ccccagcaat tccatccact   300
tggatgtcct gctcccctag accagtgacc cacatttctg gaacagggc cacggagtcc    360 tgtggcagct ccagactgtg aaatgctatt ggagccagc                          399
```

<210> SEQ ID NO 58
<211> LENGTH: 365
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 58

```
ggggtagcag agtagtcccc agaacagggc tgggctgcat cccacatcca gagaggtgtg      60
ctgagtggac actaacatac cttattgttt ttgagcttgt tcatgcagtc catgagggct     120
gggtagccac ctgagaatcg ccacaggtgc actgttgggg gtgagaggta taggtcagtg     180
agctgctggg accccagca gatgacctcc ycaaggttgg ctaagtggtg gggacggggg     240
aggcggggtg gcctggttcc ctgtagcagc aagactccct gagttccctc tgccttggtg     300
gaagaccatg ctggggaggg gatgacccta gacacaagtc taggagacct ggatttgagc     360
tccag                                                                 365

<210> SEQ ID NO 59
<211> LENGTH: 390
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 59
aatgaaccaa gcagagcaca gagcacagga gcacgacgag gatggtgcaa ggcacccgcc      60
aaatcctctg ggctccrtga ctaaagctga gggaggaagt agccatcagg gtcccttttgg   120 tgccgtctgg tctcggcact ccttggagct gatcactctc ttgctccctg cctaggcccc    180
tctccagaag gcccgatgcc cctgggtggg ggcgaggacg aggatgcaga ggaggcagta    240
gagcttcctg aggcctcggc ccccaaggcc gctctggagc ccaaggagtc caggagcccg    300
cagcaggtgg gacccacatg gaggcctgca gaacctgagc tgtgaactgg caaccctggc    360
tctggggccg agtcaccttg cacaaggagg                                      390

<210> SEQ ID NO 60
<211> LENGTH: 396
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 60
cccatgacac tggcttacct tgtgccaggc agatggcagc cacacagtgt ccaccggatg      60
gttgattttg aagcagagtt agcttgtcac ctgcctccct ttcccgggac aacagaagct    120
gacctctttg rtctcttgcg cagatgatga gtctccgggg ctctatgggt ttctgaatgt    180
catcgtccac tcagccactg gatttaagca gagttcaagt aagtactggt ttggggagsa    240
gggttgcagc ggcmgagcca gggtctccac ccaggaagga ctmatcgggc agggtgtggg   300
gaaacaggga ggttgttcag atgaccacgg gacacctttg accctggccg ctgtggagtg    360
tttgtgctgg ttgatgcctt ctgggtgtgg aattgt                               396

<210> SEQ ID NO 61
<211> LENGTH: 368
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 61
cagagagcaa aggtcacagc tacctaaagt gtttccactt caagcacaga ttgtatgcct      60
gaagactaca taccttgcat tatcaaccag ttcagcaagr gcaccaaaca agaattcgtg    120
```

```
agtggttctg aaatgataaa tactaaaagt cagcaaaaga attattgaag ttataattcc    180
taataaaaag ccatggttat aaaatattta agttttttga aaaaaatctt aaaccacca    240 tttgcattgt ttttatacta ctcaaggctt ccagagctc cccaactccc ctcaattgtt     300
aatctttaac aagtcctgcc atctattcag aaatgattat tcttcctatt ttgagttggg    360
aaacccac                                                            368
```

```
<210> SEQ ID NO 62
<211> LENGTH: 451
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 62
gatgtacacc actccctgcc tcccgcttta gaaatgaaga aaccatggct cagaggggtg     60
tggaggctca cacagcatca cagggcccga agtggaggag ctgggatatg acacaggcc    120 cacctgcctt cagaccagac ccctgtgccc ccagccgccc caccacccac agacccaga    180 gggaggacgt caggcgtcca ggctggcacc tttagcttgg gcaggccrcc gcggatggca    240
tctgcaatgg caactgcacc cttggagcgc accaggcagt ccccaaaatt aatcacctcc    300
acctgccgca aggtcttcaa ggtctgtgag ggggaagcaa kggtccagag tgagggtgca    360
gaccacaccc cagccctcag caagccccgg gggccccaca cggtcacatc ccaagccagc    420
caccacacac tgtcctcctc tgcaagtcac c                                  451
```

```
<210> SEQ ID NO 63
<211> LENGTH: 790
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 63
ttagggaaga agggccaaag cactccttgt agcactcacc cctacccttc caagccaccc     60
cagccggtgt aggtacctgt cttcagcagc atcgctctgg actcagcttc cgaggacctg    120
accagatctg gtctgcgtgt atcagctgta tgtgttgggc tctggaagct aagaaacgtc    180
tgaaaagcac tggggtcacg gctgcctggc tagctcggcc gccctcaacc ttaggcgtgg    240
atcgtacact cggtccccaa gttgcccgcc ccatccccag ccatcacttc ccggagctts    300
agttcttcct tcagaaatac gaaacaacgt gtcttggatg tcagacctca caccctctgc    360
agtgctggga gtcccgaggg cctacgggcc gccttcggcc ccgccggggc tcagaaaaag    420
gcagccactg gcttaaggtc accaagaaag agcggagggg cggggctgcg gccaggctcc    480
ggacttccag ccgggtccgg gttcccgccc tgggctcccc aaaaccgcag agccccctcc    540
caccgcactt atcctaccga agcgttcaga cctgccgccg cttctgactc gaatccggta    600
acctgataag tccgaagcgt tccagtgagg gcggggcctc acgaaggcaa cccttcgcgc    660
aacctatcag aatccccct agcaacgctg tgcccygccc atatgggtcc ggcctcccag    720
cctccctaag cccttcccca ytgggctccc gccctgcgtg ctagcgaggc wggcattggc    780
agaacggact                                                          790
```

```
<210> SEQ ID NO 64
<211> LENGTH: 496
```

```
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 64
cttgtgaccc tccaaggaaa ggaaccagca ctcatcaagg tcccactggg caccaggtgc      60
tgggcttggc gtgctgtgtg ttatcccatt tcagcttccc agcaaccctc caagttagct    120
tcagccccca ccccgccccc attttacaga aggaaaacac aaggctcagg aagtcaggtg    180
ccacccaagg aaggtcctac ggctcaggga ggagcccagg tccaggtcct gggacctggg    240 tggtggggc gtgcagagcc tgagctggga cccagtgctg aggttcagcg gggcccgagc    300
tgcagcacca ctgccccagg ctgaccgtac tgggggcccg gctaacctct gcctcctttc    360
cttctacctt cccagggkaa tgatgcggaa gagcctaagg gggtcaccag cgaaggtagt    420
agtccccgcc cctgcccgcc ctctcctttc cccagggctc tggcctcagg gcctaccctc    480
accctctccc cttcct                                                     496

<210> SEQ ID NO 65
<211> LENGTH: 395
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 65
tagaaaggcc attcctcgtg agtataatca taaacccact cacaaaaatg gttcccaatg      60
tcaaagcccc tgggagaata aggtggacat tcagtcccca aatgccctgg gcagctggcc    120
tgttttcaag agccctrtgg gaacagatct atgggaagcc atctttccag cctcacctat    180
agttataact gctgtactcg aagtccacca gcatgaggct gtcagcattt ctggctctg     240 agagcagcaa gatgttccct gggggaatgg ggtgaggttc tgctcactcc agagccctct    300
ggctcttcca tcttgggtta ggagactcag atgccttctc ctaccttcct ggatgtcatt    360
gtggcagaag acgactggcg atggggtaga ctcta                               395

<210> SEQ ID NO 66
<211> LENGTH: 353
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 66
cattccttcc agactccacc tccctccttc ctcacaggat gggtcctgct ccccagcctc      60
tggcccacat acctgctgtt cttgagtggg gtagtctgtg ggccttgctt tgtagaaagg    120
ccattcctcg tgagtataat cataaaccca ctcacaaaaa tggttcccaa tgtcaaagcc    180
cctgggagaa taaggtggac attcagtccc caaatgccct gggcagctgg cctgttttca    240
agagccctrt gggaacagat ctatgggaag ccatctttcc agcctcacct atagttataa    300
ctgctgtact cgaagtccac cagcatgagg ctgtcagcat tttctggctc tga           353

<210> SEQ ID NO 67
<211> LENGTH: 598
<212> TYPE: DNA
<213> ORGANISM: Artificial Sequence
```

```
<220> FEATURE:
<223> OTHER INFORMATION: Description of Artificial Sequence: Synthetic
      amplicon sequence

<400> SEQUENCE: 67
ccatctgagc tatttcccca cctctctcta cggtttaagg gcccagcagg agggagggag      60
caatcagact caagcctggr tgcaaatccc ggctctacca ctgctttcct gtctgatctg    120
aacgagttac ctaacctctc cgagcttatc tacaaaagct gaatgatcct tccctcatag    180
agctattgcg agaataagga gatggrggga ggtcacacca tccccaactt accaagggat    240
cttcctctga cagagactga gcaagatcca gctggtctga gctgtgtgga tctcrcctcc    300
agctgtgcac ctatwtwwta accagacacg tcctccagcc cccaagatat acccaggaat    360
tcgaaaggta aartgaaagt cacaacttcc cagcagctcr caatcaagca cagcaaacac    420
gctgctcccc agcacctcct gcagtccagc cccaccctcc ttgctgctgc gcttagagra    480
gcagcctgag accagacctc caggtctctt tcatccaacc cacctgcctg gcatcctcgg    540
ggttgggggt ctgctatagt cttcaggaag aaagacctgc cactgacata ctgtggga     598

<210> SEQ ID NO 68
<211> LENGTH: 382
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 68
tgagagggac atcctcaagc ccagcagagg gggctgcctg gaggaggygt gcctgccaga     60
gaaaactagc ccggggagat ctgggtggca tcaccggggt gccccaagga ggtaacccca   120
tggaggttac ctgggcaatt cagccacacg cacraatctc ttccaggctt catcgctagt   180
cagcaggatt ttcagatgca ctgggctaac tttcttctgg aagtattcaa tgacttcttc   240
agtgaagcgt ttcttttcta gttggaaaca aaaaggataa gattggaaga aagtttgcta   300
ccacataaat ggcattgagt ataaggtggt tcggtgttaa tcctcctgaa ccagctgtca   360
catggggtat ttttgatgga gg                                             382

<210> SEQ ID NO 69
<211> LENGTH: 398
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 69
cccttctcgc agctgattac ggtcacgtcg atcccgtctt ccagtctccc acgagacgga     60
gcccgggaaa agagtcgacc ccatgctctg ccgcccccgc accccacccc tcgggaatcc   120
ccaccgtctt tcccaatcac cttcttcttc tcaaggcctc ccatcgctcc acgttgagga   180
gccgactagg gccgcgcgta caggsagctc cacttcctcc cgcacgtgcc ctgccaagga   240
ccccgaggac cctcccccacc ccacgctgtc tgtttgwgcg ggctgcccaa tgagatgcct   300
gtayaagtcc agggaaagat ggggatttcc tcctcaagat ttaaaactat agtctgaaaa   360
aaatcactga gaacactctt tccagatctt tcccgctc                            398

<210> SEQ ID NO 70
<211> LENGTH: 398
```

```
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 70
ccactcttgt tcttgggcat cagctggttg cctggctgtg ttagtgaccc agcccacaac      60 agcccctac  tctaccctgg ctacatgcag tgcccatctc tggggtcact gcagagaga     120 cctggctaat gccaccctct cttccggctg cctttcagga agaccatgct caatgacctc    180
ctgcggttcg atgtgaaaga ctgctcctgg tgcaggtggg tggcccccgtg ctccagggcc   240 ctgcctttcc tcctagaaca cagtggcaca gtgctgggtc ccagttgcta gcagagtctc    300
tctcatcatg ggaagctaga aagaagcttc caggaggaga taaccacggc ctcagggatg    360
ccacatccag agccgccctg tcaggctgag gagatcaa                            398

<210> SEQ ID NO 71
<211> LENGTH: 380
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 71
tgaatcctca tctggggaag tttcaagaat aaaagcmgtc ccatctcagc agtctcgagt     60
gtggtgaaat gtgagcgggc cctgtgaggc cggggctgag ctgtcctctc ccctgcagg    120 tggcccagag tggcgagatc cccccatctt gctgcaactt ccccgtggct gtgtgccggg   180
acaagatgtt tgtattctct gggcaaagcg agccaaaat aaccaacaac ctcttccagt    240
ttgaattcaa ggacaagacg tgagtactct ggccagtggg gtggagggag acggtcagt    300 tccctcgaat ccttctgaat atgaagaayg cctcttgcac ctggtggccr tggtaaccat   360
ccttgtgagc tctgcaaaca                                              380

<210> SEQ ID NO 72
<211> LENGTH: 698
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 72
cagaagcatg gaattgctga caagcacaga gcttggcgtg gggttggagg ttgcatcagt     60
ctcctgcggt tgctgtagcg aagggctgca aactgggtgg tttggagcag cagacaggta   120
ctcacagctt tgagggccaa gagtcccatc taaggtgtca gcaagggcag tgccctcaga   180
gcctcagggg tgggtccttc ctgcctcttc caatttctgg tggtgcccag agttccttga   240
agtcccttgg ctcgcagctg tatcactctg ccttggtctt tacctgccgc cttccctcgg   300
catctgtgtc ttcacacggc cctcttgtaa ggacaccagt cattgcgtta gggcccaccc   360
taatcccgta tgacctcctc taaacttatt acctctgcaa agaccctatt tccaaaaaag   420
gtcacattcc cagtgctggc agttaggacc tcagtgtatc tttgcgggga cacagttcaa   480
cctgctaccc atccatcatt ttgtattctg agatcttttt ttctgttttt agctatgtga   540
aaggcatcta ctcttttggc ttgatggaaa ccaacttcta cgaccaggca gaaaaactcg   600
ccaaagaggt aagtgggtcc ttcctaaggt gcctgacccc tcagggagta gcygttggct   660
```
ggaccagggc atatgagggg caccattcgt gtgtgacc    698

<210> SEQ ID NO 73
<211> LENGTH: 698
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 73
gggggttgtc ttttgcatag agaccatgac caggtctggg acagaggaaa gtcaaataaa    60
tcacacatta gagttagaag cagaggctca ggctgagccc aggtttatta tccaaaatca   120
aaatgaaatg cagtgattaa aggacacaag gcctcagtgt gcatcattct cattgtggct   180
ttcaggcggc tgtggaagac agggtgggga tggtggcttc gggaggtgag gtgctctggg   240
acttgggcaa gtcttargca agccattcct gctttctggg cctggctccc atgggccatt   300
agaaatgaaa atgctttgtg gactgctgag gacggtgcaa gggtgaggtt cccagctca   360 ccggatcatg gccagcaccc agggcatcag cttctgcttt atggtggggt ctgcaggtgg   420
gaagtccttg gccttcagaa tgacctcatg ggcctcctgg aagaggtcct cccccactgc   480
tgcctccacg cgctgccgcc atgtggccag cttgggtcgg ccttcgaaga cttggcagcc   540
agcacccacg ggctgtgggg aaaagggtac agactgggga tggatggttg tgagggcagg   600
gatgggcagc atctgatttg gggaccacag atctccagga ggtgtttgca cacacactta   660
agcacagtgc catagcccgg tgtggcagca taagcagg    698

<210> SEQ ID NO 74
<211> LENGTH: 395
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 74
ctcctctgtc cctcctcaga cccctcctcc tcctcccaca cgcccactgt aaagggctcc    60
tgcgtcagga gctgccaggc cgagggccag ggcacccsga ggacagctgc tccrgcagca   120
ctcacccgat gcatgtcttc atacttgaga aaaagcacgt tcgagtccat gcggtgctcc   180
cagaactcct gcacgtgctc aaaccaggag ccgtagccca ctgcggagac aggggacagg   240
gtgagccaca cggctgggca ggagaagcgc acacatgggg ccatccccac cccacagggc   300
tgccctcctg ccacccagca gccgtgatga ggacatcgtg atccctgcgg acaagtctgg   360
caaaggcccc cgaggcactc acgtcttgag ccatc    395

<210> SEQ ID NO 75
<211> LENGTH: 383
<212> TYPE: DNA
<213> ORGANISM: Artificial Sequence
<220> FEATURE:
<223> OTHER INFORMATION: Description of Artificial Sequence: Synthetic
      amplicon sequence
<220> FEATURE:
<221> NAME/KEY: modified_base
<222> LOCATION: (83)..(86)
<223> OTHER INFORMATION: c or not present

<400> SEQUENCE: 75
ctggactgga ggccaaagtc ytgcggggaa cgtgcgggaa gagcagagcg tgcaggcagc    60

```
rgagactaac aagaagccct ggccccagag ggcaggaaca ggtggacgaa caaccagatg      120
agagaacgta ccaggcatgc aagctagacc caggaatcaa cgggctgagg cttagcgtcc      180
cctacggcgt ccaccagcct gaccgcgggc ctgctgggcc cgggggggagg ggccttcctg      240 ctggggtcga gctgcagcgc acgggtgggc attagaggca caatagagca ggttagttag      300
agctcctggg gggacagggc aggggcaggg ccgaggctgg cgatgtaagg gttggcctgc      360
caggacagca caggtagcac caa                                              383
```

<210> SEQ ID NO 76
<211> LENGTH: 385
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 76

```
tgaatagtgc gttgcaggtc catgcacttg tcagtttgtt catttcctgg aggcttctag      60
ccctgggtgt ccatggccct tgcagatact tgctggtcag gaatgagcct tctgaggcaa      120
gactgctgga ttgtccaggc agggctattg atgccagccc cttaacttaa ttctgcccag      180
acaagaagat gtttgaggtg aagcggcggg agcagctgtt ggcactgaag aacctggcac      240
agctgaacga catccaccag cagtacaaga tccttgatgt catgctcaag gggctctttta     300 aggtgtgtgc aggcagggggg cagctcatgg caggtccagt ctttgatcta ggcactgatg      360
ggtaaacagg agttccctaa cgggt                                            385
```

<210> SEQ ID NO 77
<211> LENGTH: 357
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 77

```
acaggagttc cctaacgggt tggtgttcag ggacagggga actgcgcaca cgtaagactt      60
gaagtggggt ttaaataaat ggggatggga gcagtctgtg atgggcactg cgaagccact      120
cagccctggc gggattccct caggtgctgg aggactcccg dacagtgctc accgctgctg      180
atgtgctccc agatgggccc ttcccccagg acgagaagct gaaggatggt atggtctgcc      240
ctgccccgcc ctgtcctccg caccacccga tcttctctag ctgctccttc tctcctgttc      300
ttgtcactct tttttctcc ccggaagtgc cctcttgtgg caccttctaa gtggtcc         357
```

<210> SEQ ID NO 78
<211> LENGTH: 355
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 78

```
gcagagatca gagcatcgaa taatggttgc taaaatatct tggaaaagga aacagtccta      60
tccagatgaa atgtgttcat accgtagaca tgacagagac cagctcttgt tcagtgcccc      120
ctacctgctg gctgcttcct cggctcctcg aacagatcag ccgagcttat ggaggaactt      180
gcygacagcc tctctaggcg ggccctggtc tcatactaga gaagacaagg aaaaggaaat      240
```

```
gttaggctcc aaagaytgtg ggcagttttg caaaaagaat cacygaagag ctgtcatttg      300
aaagtgtttg accccaggc tctttcyttc aacagttac tgaatgccac tgcca            355

<210> SEQ ID NO 79
<211> LENGTH: 399
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 79
ccttagaagc ctggaactct tgttaaatag gtagctattt gtatgaacag gaaactgagt       60
cagcttatta ggaaatgata agattctgca gaagaacata ttgtatagtt ttccgtagaa      120
agaggagagg cttaattcct ttttgttttg aacttagatc aaattactca ttaaacaaga      180
tgatgacctt gaagttcccg cctatgaaga catcttcagg gatgaagagg aggatgaaga      240
gcattcagga aatgacagtg atgggtcaga gccttctgrg aagcgcacac ggttagaaga      300
ggtgagtttg ggtctctcac agctatccca gaggaacttg cactcccaga ggtcggaggt      360
catcctgaag cctgccaggc caaggtgtac tgagggcag                            399

<210> SEQ ID NO 80
<211> LENGTH: 379
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 80
ttccacctcc cttgttgttc tccctgcccc ctgcctggct cccytctgcc tcttagagct       60
tgtaactgtc tttgttgatc cttcttgcag acttgggcat agacctcggg cctggtccct      120
gcaaggagcg ggtgtgaatg ctccacggcc ccttagctac ctgtgacacc ttgtgcccac      180
aggttccgta gtaagatgga agctgctggc ttcactatct cgggagccag tcaccccatc      240
tgccctgtga tgctgggtga tgcccggctg gcctctcgca tggcggatga catgctgaag      300
agaggtaagg gtgctgagac aagggaactg gtggtgggtc ctgagagaag agaaagggaa      360
acccctagac tgtgaccca                                                  379

<210> SEQ ID NO 81
<211> LENGTH: 398
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 81
gccagcatta ataaaagag ccaggaatta aaattttagt gtcctaatgc ctctacataa        60
tttgccgtat tttcctttca tggcttagct ataggaaatt taccctctgg gctctctcat      120
gctcttctcg agccttctta actcgttcta ttctttcttt gatctctcgc tcttcacgtt      180
ttcgctcata ctttctccga tgttctgcaa ttttctgtgc ctagaaaaaa gagccatagc      240
aaaataagct tgctccaaaa gctgaataac atcaacacaa atattctttg tagagagatg      300
tttaattcaa catgcagttc agaaaaatga cagatttgtc ttgtasaaaa agacctaaca      360
caagctaagc ctttaagaaa accaacctca actgcatg                             398
```

<210> SEQ ID NO 82
<211> LENGTH: 371
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 82
tctgctcctt gtcctcatcc ccacccatga gcaggacatg aaccccccaga gcctgccaga       60 gcatgctctg cacagtaagt aagtgtgtgt ccaggcacag aacgcccaag agaaggccca      120
gagggcggcc cattcccgga gagagcttca gtacctgtcc tgaagctgga cacggtggcc      180
ccagttcaag gatttcacgt gattttgaac agcttctgcc atcttcctcc tgtgaagata      240
cgaaacaaaa tgtaaaatcc acaacacagg tgttagctgc agggcctcac ratggactat      300
tagattcaaa tggtacattc atagaaatat caaaaaacaa gagtgctttt aaaggtggca      360
aaacgtgaca t                                                           371

<210> SEQ ID NO 83
<211> LENGTH: 395
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 83
cggactgagc ttttaccccct gggctgtggt tgggcggtgg ggaaaggcca tgtatcaggg       60
cctagcagag gccttgggtg gcatgggcaa ttggaggcct tgccctgggc cagtgtggtc      120
cccgccatgc gtccccattc cgcatcactc ggtctctccc acagggatga cggaacacac      180
caagaacctc ctacgggcct tttatgagct gtcgcagact caccggggta atggcatccc      240
ccaaagctgt ggtgtgaccs tgggcaatcc ctggggcctc tcactcccat gctgaggtgg      300
gtcagaccca cagcgcctga cctcaggctc cctctgggct gggcctggtc ccaggtgctg      360
ggatttgcga tgggcctgcg gggaacatct agatc                                 395

<210> SEQ ID NO 84
<211> LENGTH: 328
<212> TYPE: DNA
<213> ORGANISM: Artificial Sequence
<220> FEATURE:
<223> OTHER INFORMATION: Description of Artificial Sequence: Synthetic
      amplicon sequence

<400> SEQUENCE: 84
atctcacccc tggattttcc caggccaggc tgtgcaccca aaaactgggg ctgcagggaa       60
gggtggtttc cgcacccctg ctcacctggg gtcatcctca aagagatact ggatcccctg      120
gccatggtgc acatcccagt ccacgacgag gatcctgggt acagacagcg ctggtggcaa      180
aggggcaggg cctcccacct ccaggagccc ggccagggat gggaaggtgc tggctgggtt      240
ctctcgcctc ctgcgcygcc ccttgctgtg tggcctgggc ccaccccccct gcagccagcc      300 tggcacacac ctgtgtagcc cgtgtttc                                         328

<210> SEQ ID NO 85
<211> LENGTH: 483
<212> TYPE: DNA
<213> ORGANISM: Mycobacterium chelonae -continued

```
<400> SEQUENCE: 85
acgggtgagt aacacgtggg tgatctgccc tgcactctgg gataagcctg ggaaactggg        60
tctaataccg gataggacca cacacttcat ggtgagtggt gcaaagcttt tgcggtgtgg       120
gatgagcccg cggcctatca gcttgttggt ggggtaatgg cccaccaagg cgacgacggg       180
tagccggcct gagagggtga ccggccacac tgggactgag atacggccca gactcctacg       240
ggaggcagca gtggggaata ttgcacaatg ggcgcaagcc tgatgcagcg acgccgcgtg       300
agggatgacg gccttcgggt tgtaaacctc tttcagtagg gacgaagcga aagtgacggt       360
acctacagaa gaaggaccgg ccaactacgt gccagcagcc gcggtaatac gtagggtccg       420
agcgttgtcc ggaattactg ggcgtaaaga gctcgtaggt ggtttgtcgc gttgttcgtg       480
aaa                                                                     483
```